(12) United States Patent
Burn et al.

(10) Patent No.: US 8,049,066 B2
(45) Date of Patent: Nov. 1, 2011

(54) METHODS AND MEANS FOR MODULATING CELLULOSE BIOSYNTHESIS IN FIBER PRODUCING PLANTS

(75) Inventors: Joanne Elizabeth Burn, Murrumbateman (AU); Richard Edward Williamson, Murrumbateman (AU)

(73) Assignee: Australian National University, Canberra, ACT (AU)

( * ) Notice: Subject to any disclaimer, the term of this patent is extended or adjusted under 35 U.S.C. 154(b) by 1075 days.

(21) Appl. No.: 11/902,478

(22) Filed: Sep. 21, 2007

(65) Prior Publication Data

US 2008/0235825 A1 Sep. 25, 2008

Related U.S. Application Data

(62) Division of application No. 10/733,407, filed on Dec. 12, 2003, now Pat. No. 7,482,508.

(60) Provisional application No. 60/432,674, filed on Dec. 12, 2002.

(51) Int. Cl.
*C12N 15/82* (2006.01)
*A01H 5/00* (2006.01)
*C07H 21/04* (2006.01)
*C12Q 1/68* (2006.01)

(52) U.S. Cl. ........ 800/284; 800/278; 800/285; 800/287; 800/298; 536/23.2; 536/23.6; 536/24.5; 435/6.1

(58) Field of Classification Search .................... None
See application file for complete search history.

(56) References Cited

U.S. PATENT DOCUMENTS 6,316,698 B1   11/2001   Allen et al.

FOREIGN PATENT DOCUMENTS

| JP | 2000-41685 | | 2/2000 |
|---|---|---|---|
| WO | WO 97/24448 | * | 7/1997 |
| WO | WO 98/50568 | | 11/1998 |
| WO | WO 03/098186 | | 11/2003 |

OTHER PUBLICATIONS

Nicol et al., A plasma membrane-bound putative endo-1,4-β-D-glucanase is required for normal wall assembly as cell elongation in *Arabidopsis*, The EMBO Journal, 17:5563-76 (1998).

His et al., "Altered pectin composition in primary cell walls of *korrigan*, a dwarf mutant of *Arabidopsis* deficient in a membrane-bound endo-1,4-β-glucanase," *Planta*, 2001, vol. 212, 348-358, Springer-Verlag.

Lane et al., "Temperature-Sensitive Alleles of RSW2 Link the KORRIGAN Endo-1,4-β-Glucanase to Cellulose Synthesis and Cytokinesis in *Arabidopsis*," *Plant Physiologyl*, May 2001, vol. 126 278-288, American Society of Plant Physiologists.

Monroe et al., Structure, Properties, and Tissue Localization of Apoplastic α-Glucosidase in Crucifers, *Plant Physiology*, Feb. 1999, vol. 199, 385-397, American Society of Plant Physiologists.

Peng et al., "Fractionation of carbohydrates in *Arabidopsis* root cell walls shows that three radial swelling loci are specifically involved in cellulose production," *Planta*, 2000, vol. 211, 406-414, Springer-Verlag.

Zuo et al., "KORRIGAN, an *Arabidopsis* Endo-1,4-β-Glucanase, Localizes to the Cell Plate by Polarized Targeting and Is Essential for Cytokinesis," *The Plant Cell*, Jul. 2000, vol. 12, 1137-1152, American Society of Plant Physiologists.

* cited by examiner

*Primary Examiner* — Cathy Kingdon Worley
(74) *Attorney, Agent, or Firm* — Buchanan Ingersoll & Rooney PC

(57) ABSTRACT

The present invention provides novel genes involved in cellulose biosynthesis and methods using such genes to modulate cellulose biosynthesis in fiber-producing plants such as cotton. The invention also provides methods for identifying and isolating alleles of these genes in a population of fiber-producing plants that correlate with the quality of the produced fibers.

39 Claims, 8 Drawing Sheets

SEQUENCE LISTING

<160> NUMBER OF SEQ ID NOS: 33

<210> SEQ ID NO 1
<211> LENGTH: 2845
<212> TYPE: DNA
<213> ORGANISM: Arabidopsis thaliana

<400> SEQUENCE: 1

```
acatttcttc acttccacac acttttactt ctttctctct tctcttctct tctccagatc      60
tgatcccaaa cctttgattc attgttgttg ttctctgctg ctttatcaga gagcatcatc     120
atgtacggaa gagatccatg gggaggtcca ttggagataa acactgcaga ttccgccacc     180
gacgatgatc gtagtcggaa tttaaacgat ttggatcgtg cggctctttc acgtccacta     240
gatgagacgc agcagagttg gttacttggt ccaacggagc agaagaagaa gaagtacgtc     300
gatctcggtt gtattatcgt tagccgcaag atcttcgtct ggactgttgg tactcttgtt     360
gccgccgcgt tactcgccgg attcattacc ttgatcgtta aaactgtgcc gcgtcatcat     420
cctaagactc cgccgccgga taattatact atagctctac acaaagctct taagttcttc     480
aatgctcaga aatgtaagtg tagaatctac ttagatctga taaaatttag atatagagtt     540
ttagatctaa gtctgatttt gattgttgta gctgggaaat tgccaaagca taataacgtg     600
tcatggagag gtaattctgg gcttcaagat gggaaaggtg aaacaggaag cttctataaa     660
gatttggtgg gaggttatta tgatgctggt gatgctatca agttcaattt ccccatggct     720
tatgctatga ctatgttgag ctggagtgtt attgaatata gtgctaaata cgaagctgct     780
ggtgagctca ctcatgttaa ggagcttatc aaatggggaa ctgattactt tctcaagact     840
ttcaatagta ctgctgattc cattgatgat cttgtgtcac aggtacttgt ttatgacctt     900
cgtaggagat ctttcatatt gagttgtttg ttcactcgtt acatgtttaa tgtaggttgg     960
atcagggaat actgatgatg gaaatacaga tcctaatgac cattactgtt ggatgcgacc    1020
tgaggatatg gactataaaa ggcccgtgac tacttgtaat ggtggatgtt cggatctcgc    1080
tgcagagatg gcagctgctc tggcttcagc atctattgta ttcaaggata acaaggaata    1140
ttctaaaaag cttgtccatg gtgctaaggt ggtgtatcag tttggaagga cgaggagagg    1200
```

```
gagatatagt gcaggcactg cggaatctag caagttctat aattcaagta tgtattggga    1260
tgagttcatt tggggtggtg cttggatgta ttatgctacc ggaaatgtaa cgtatctcaa    1320
tctaatcacc caacctacta tggccaagca tgctggtgcc ttctggggtg gcccttacta    1380
tggtgtattt agctgggaca caagcttgc  tggtgctcag gtcagtccac acataacaac    1440
ctgctgtgtt tatgtttctt aaatattcat gtcttcttga tcatttgcct taaccatact    1500
actcttgact cttttgaatc ccttttgcga ttttagttgc tgttgagccg gttgaggttg    1560
tttctgagtc ctggatatcc atatgaagaa attctaagga ccttccacaa tcagaccagc    1620
atagtcatgt gctcatactt gcctattttc aacaaattta acagaaccaa tggttagtta    1680
ccttccagct ttaatgtctg cctctaataa aactccaact gtggggcttg ttcttgtttc    1740
aaatatctaa aatgaaatct ttggtatgtg caggaggttt aatagagttg aatcatggag    1800
ctccacagcc gctgcaatat tctgtaaatg cagcttttctt agcgactcta tacagtgatt    1860
atctggatgc tgctgatact cctggatggt actgtggacc taatttctat tcgacaagtg    1920
tgctacgtga ctttgctaga tcccaggtat tgcttctttt cctttactct ttacagaaat    1980
ggtaatctca gatatagtaa tggataagat ccaaaaatga cacttttaac caagattgta    2040
cgaagatctt tttaaactcc attttttatt ttgacatcta aattggattt aactcggcct    2100
tgctgtattt tggcagattg attatatact gggtaaaaac cctcggaaaa tgagttatgt    2160
cgttggtttt ggcacaaaat acccaagaca tgtgcatcac agaggagctt cgatacccaa    2220
gaacaaagtc aagtataact gcaaaggagg atggaaatgg agagacagca agaaaccaaa    2280
cccaaacacg attgaaggag ccatggttgc tggtcctgac aagcgcgacg ggtaccgtga    2340
tgtccgtatg aactacaact acactgaacc gactcttgca ggcaatgctg gtctagtcgc    2400
agctcttgtg gcattatcgg gtgaagaaga agccaccggt aagatagaca aaaacactat    2460
tttctcagct gttcctcctt tgttccctac tccaccacct ccaccagcac catggaaacc    2520
ttgagaaagc tagacttgtg tgattctgtc gctgctgcca aaaaaaatga atgaggtaag    2580
aaggatttgg gtgtgagacc agaagattag aagctaaaca caagtcagcc ataaccaaac    2640
tactaaggat ttcatttggc tttactagat acaaacacgg ggtgggttac tttaccacaa    2700
gcattgtctt tcttttcttt tttttgggttg ctgttttgtt cttgtgagat atcatatata    2760
tctatgcgtt ttactctgta tatgtttgat accaaacttg tattctttga taaacaatt    2820 aatgaactgt attaaacttt taact                                          2845
```

<210> SEQ ID NO 2
<211> LENGTH: 2031
<212> TYPE: DNA
<213> ORGANISM: Artificial Sequence
<220> FEATURE:
<223> OTHER INFORMATION: cDNA RSW2 homologue from cotton
<220> FEATURE:
<221> NAME/KEY: misc_feature
<222> LOCATION: (47)..(1906)
<223> OTHER INFORMATION: coding region RSW2 homologue

<400> SEQUENCE: 2

```
ggcacgagcc tgcattttcc gcccactact cttccaaatc ctcatcatgt acggcagaga      60
tccgtgggga ggtcccctgg agataaacgc cactgattct gccactgacg acgacaggag     120
caggaatctg caggacctgg atagggctgc actctctcgc cccttggacg agactcagca     180
aagctggctg cttggccccg gggagcaaaa gaagaagaag aagtacgttg atctcggatg     240
tatcattgtg agccgcaaga tctttgtatg gaccgtgggg accctgctag tctccgccct     300
```

```
cctggccgga ctcatcaccc tcatcgtcaa gactgtccca cgtcatcacc accgccactc    360
tccgcccgat aactacactc tggctcttca caaggcgctc atgttcttta atgctcagcg    420
ttctggaaag ctgcccaagc ataataatgt gtcgtggaga gggaactcgg gcctccaaga    480
tggcaaatcc gatccctccg ttttgatgaa agatctggtc ggcggatatt acgatgctgg    540
agatgctatc aagtttaact ttcctgcatc tttttcaatg actatgttga gctggagtgt    600
catcgaatac agtgctaaat acgaggctgc cggcgagctc aatcatgtta aagagatcat    660
caaatggggt actgattatc ttctgaagac cttcaacaat actgctgata ccattgacag    720
gattgctgcg caggtaggga taggagatac atctggagga agttcagccc caaatgatca    780
ttattgctgg atgcgccctg aggacattga ttaccccccgt cctgtatatg aatgtcatag    840
ttgctccgat cttgctgctg aaatggctgc tgctttggct tctgcttcca tcgttttcaa    900
agacaacaaa gcatactctc aaaagcttgt ccatggtgcc cgaacactct ttatgtttgc    960
tagggatcaa agaggcagat atagtgctgg tggttctgac cctgccctct tttataattc   1020
ctcaagttac tgggatgagt ttgttggg tggagcctgg ttatactatg ccactgggaa    1080
ttcatcctat cttcagttag ctactcatcc taaacttgcc aagcatgctg gtgctttctg   1140
gggtggccca gattatggtg ttcttagctg ggataataag cttgctggtg ctcaggtgct   1200
tctgagccga ttgagattgt ttttgagtcc tgggtatcca tatgaggaaa tattgagtac   1260
gtttcataat caaaccagca taattatgtg ctcattcctt ccggttttca ctagctttaa   1320
tagaacaaaa ggaggtttga ttcagttaaa ccatggaagg cctcagccac tgcaatacgt   1380
agtcaatgca gccttcttag ccgccctata tagtgattat cttgatactg ctgatacacc   1440
tggatggtat tgtggtccca atttctattc aactgatgtc ctgcgtgaat ttgccaaaac   1500
ccagattgat tatatccttg gcaaaaatcc tcgaaaaatg agctatgttg tgggctttgg   1560
taaccattat ccaaagcatg ttcaccatag aggggcatct atccctaaga ataagatcaa   1620
atataactgt aaaggggga tggaaatggag ggatacgtca aaaccaaacc ccaacacact   1680
tgtgggagcc atggtagctg gacctgacaa gcatgatggg tttcgtgatg ttcgcaccaa   1740
ctacaactat acggagccaa ctctagcagg caacgcaggg ttggttgctg cactcgtggc   1800
attgtctggt gacaaggcaa ccgtgattga caagaatacc attttttctg cagttccacc   1860
aatgtttcct acaccaccac cacctccggc accttggaaa ccatgaaaac gttttgatct   1920
ttcttctgtc catgtgtgac ttacagtctg atgattttgg aattagtttt tggtacgtaa   1980
atgaccttgg aagtgtaagt aacgcaaaag gcaagacagg agatgagtga t           2031
```

<210> SEQ ID NO 3
<211> LENGTH: 4500
<212> TYPE: DNA
<213> ORGANISM: Arabidopsis thaliana

<400> SEQUENCE: 3

```
gtgtactgcg agaactgctt attacataca tggcagataa tccgcgtaga agaagggttt     60
aacggagacg aatttgaact ctccgacgaa ataatcgtct tctccggcat catcttcaga    120
aagctattcc aaattagggt tttgactttt gattgaagaa gacaggtcta gaaacttaca    180
tacaccaatt ttaaaatcga gtttgggccg aattatggac cgtactttgg gctatgggcc    240
ttcattttaa taaacaggtc ggatatatcc accggacccg gaatgatcgt cttcctcagt    300
gttgtatttt ggctttcctc attgcttcct caatctaagg atttccatga acaaggaact    360
aaaatgagat ctcttctctt tgtactatca ctcatttgct tttgctctca aacagcactt    420
```

```
tcatggaaga aggaagagtt tcgcagctgt gaccaaactc cattttgtaa acgcgctcga    480
tctcgtactc ccggcgcgtg ttctctaatt gtcggcgatg tttccatcac tgatggagat    540
ctcgtagcga agcttctacc gaaagcgcct aatcaaggcg atggggatca gatcaagccg    600
ttgattcttt ctctctcagt ttacaaggat gggatcgtgc ggcttaaaat cgatgaggac    660
cattcgttga acccgccgaa gaagaggttc caagttcctg atgtggtagt gtctgagttt    720
gaggagaaga agatctggct gcagaaagta gcgacggaga cgatctctgg agacactagt    780
ccgtcttcag tagtttatgt atccgatggt tacgaggcgg tggtgcgaca cgatccgttt    840
gaggtgtatg tgcgtgagaa atcaggtgat cgccgtcgcg ttgtgtcatt gaattctcat    900
ggattatttg attttgagca gttggggagg aaaactgaag agataactg ggaagagaaa     960
tttaggactc atacagattc tagaccatct ggtcctcaat ctattagttt cgatgtttcg    1020
ttttatgatt ccagtttcgt ttatggaatt cctgaacacg ccactagctt cgcgttgaag    1080
cctaccaagg gtcctggagt tgaggaatct gaaccctaca ggcttttaa tctagatgtg     1140
tttgaatacg atcatgaatc accgtttggg ctttacgggt cgattccgtt catggtttcg    1200
catgggaagt ctggtaaaac ttcaggattt ttctggttga atgctgcgga aatgcagatt    1260
gatgtgttgg ctaatggttg ggatgcagag agtggtattt ctttgccttc tagtcacagt    1320
aggatcgaca cattctggat gagcgaggca gggattgtgg atacattctt tttcgttggg    1380
cctgagccaa aggatgttgt aaagcagtat gcaagtgtga caggtacttc agccatgcct    1440
cagttgtttg ccactggtta tcatcaatgt aggtggaact acaaagatga ggaggatgtg    1500
gcacaggtgg actcgaaatt cgatgaacac gatattcctt atgatgttct ctggcttgac    1560
attgagcata cagatgggaa gagatacttt acatgggata gtgtgttgtt tcctcatcca    1620
gaggagatgc aaaagaaatt ggctgcaaag ggtaggaaga tggtgaccat tgtggatcct    1680
catatcaaga gggatgactc atacttctta cacaaagagg ctactcagat gggatactat    1740
gttaaggatt catctggaaa agactttgat ggttggtgct ggcctggttc atcatcttac    1800
attgatatgt tgagcccaga gattagaaaa tggtgggggtg ggaggttctc gtataagaac    1860
tatgttggtt caactccatc attgtacacc tggaatgaca tgaatgagcc ttctgtattc    1920
aatggtcccg aggtataact ttctgtctga atggtctttt tttcttgttc cgttattgtt    1980
tttctgtaat ctgtatagct catttctcat attcatttg ggattgcagt tgaatatagc      2040
aatccattgt ttttctattg cacaattatg gatatgtttg aactctgata gattatacat    2100
cccttatctt gcatactatg acaccttta ttaattattg cactactaaa gcaagtattt      2160
taagatccat tttatgttta tgtggttta cattggatat ttgtttctgt gacttctttta     2220
agagtggagt gtaagctatg gttgcatatc tccacctctg atttgcttat atcgtagaaa    2280
gtttatcata tatgtaaagg tctattactg agatgaagac tggcactttt tctttcttt     2340
tttgttggag taggttacta tgccaagaga tgcattacat gttggggtg ttgaacacag      2400
agaagttcat aacgcatatg gatattactt ccacatggcg acttccgatg acttgttat     2460
gcgtgaagaa ggaaaggata ggccttttgt attgtcaaga gcaatctttc ccggcactca    2520
aagatacgga gcaatttgga ctggagataa cacagccgaa tgggaacacc ttagagtctc    2580
cattccaatg atattgacac ttggtcttac tggaattaca ttctctggta caaacaaatt    2640
tagctgttca aattctgctg gcgttttttt ttcttctc aaatttaatg gaagttttct        2700
tttcttttgc aggagctgat attggtgggt ttttggaaa tcctgaacca gaacttctag       2760
ttaggtggta ccaagtgggt gcttactatc catttttcag gggtcatgct catcacgata    2820
```

| | |
|---|---|
| ccaaaagacg agagccttgg ttgtttgggt aagatgtgat ttagtactta attttttctt | 2880 |
| gtcaagaggt attattttag tatgcggtcc aggtctagtc tatggatatt tgcttgatgg | 2940 |
| atgatcaagc agattgaaat gtagtgatac tggttattga gaaaagaata caattgcgga | 3000 |
| aactaaaacc tggtgttgca ctctagtcag ttgattgtct aaatagttag gccattagtt | 3060 |
| tcatcaagta ggcattgcaa cggttgtcca gaagtctctc tgcctttgtt ttgctggctc | 3120 |
| ataaatgttg cactttctca ttcgaatcaa atcaatgttc tcttgtttca gtgaacggaa | 3180 |
| cacagaactc atgagagatg ccatacacac tcgttacaca ctgctcccat acttctacac | 3240 |
| gttgttcaga gaagcaaacg ttacgggtgt tcctgttgta cgcccattat ggatggaatt | 3300 |
| cccgcaagat gaagctactt ttagcaacga tgaagccttc atggtcggta gtggtctact | 3360 |
| ggttcaagga gtttacacca aggtacttga gcgctaagta caacttccta cttatttata | 3420 |
| ttttggcctt tgtatctctt tacttaatca tatactccag ataaatgatc aaaccctgcc | 3480 |
| acataccctc ttctcgtctt tctgcaaaat tagggaacaa cgcaagcttc cgtgtatttg | 3540 |
| cctggcaaag aatcatggta tgacttgaga acggtaagac ttacgttgg aggcaagact | 3600 |
| cacaagatgg atgctccaga ggagagtatt cctgcgtttc aaaaggcagg aaccatcatc | 3660 |
| ccaaggaagg accggtttag gcgaagttcc tctcaaatgg acaatgatcc ttatactttg | 3720 |
| gtacgtacaa cacttgcatc acactgtttt atcatctgct atcagcacca tgaacaaagt | 3780 |
| aaaaccggtt ggtaaaaaga ttatctctga aagtgaaatc ccaatgataa actatgtgat | 3840 |
| ctaacatcta aaacccttca ggtggtagct ttgaacagtt ctcaagaagc agaaggtgaa | 3900 |
| ctctacatcg atgacggcaa aagctttgaa ttcagacgag gctcttacat ccatcgtcgc | 3960 |
| ttcgtcttct caaagggtgt tcttacatca acgaacttag ctcctccaga agctcgtctc | 4020 |
| tcttcccaat gcttgatcga cagaattatc ctcttgggac acagctcagg tccaaaatct | 4080 |
| gcgttggtgg aaccgttgaa tcaaaaggca gagattgaga tgggacctct gcgaatgggt | 4140 |
| gggcttgtag cttcctcggg tacaaaggtg ttgactatcc gcaaaccggg tgttcgagtg | 4200 |
| gaccaagact ggaccgtaaa gattctgtga ttgaacggtt tgaaccagtt tcactcatgg | 4260 |
| ccgttagagt ggccgaaatc tgcttttccg gcgacggaat atcacacttt ttaatatatg | 4320 |
| tttggagatt tagacttaaa tagttgtaag agctaacagt ttgaaagtca ctttgcattg | 4380 |
| ttgtttatct tcatataaat gagtttagat tttgataatt tcagaattcg tggaatcata | 4440 |
| attaacaatt ttgataggga aaaataattt gttttttta gtcagagggt caaataatct | 4500 |

<210> SEQ ID NO 4
<211> LENGTH: 1773
<212> TYPE: DNA
<213> ORGANISM: Artificial Sequence
<220> FEATURE:
<223> OTHER INFORMATION: cDNA RSW3 homologue from cotton (partial 3'
      end)
<220> FEATURE:
<221> NAME/KEY: misc_feature
<222> LOCATION: (2)..(1576)
<223> OTHER INFORMATION: C-terminal part of the coding region

<400> SEQUENCE: 4

| | |
|---|---|
| atatgatgtt ttgtggcttg atattgagca tactgatgga agagggtatt tcacatggga | 60 |
| taagatgcta ttcccacatc cagaagagat gcaaggaaa ttggctgcca aaggtaggca | 120 |
| tatggtgaca attgtggatc cgcatattaa gagggatgag tcatttcact tgcacaagga | 180 |
| tgcttcccag aggggtatt atgtaaagga tgcaactggc aaggattatg atgggtggtg | 240 |

-continued

```
ctggccaggc tcctcctcct acccagatat gttaaatccc gagattaggt catggtgggc    300
tgagaagttc tcctatgata attatgtcgg ttcaactcct tcattgtaca tttggaatga    360
catgaatgag ccttctgtgt taatggacc tgaggtgaca atgcccagag atgctttaca     420
tgttggtgga gtggaacatc gggagttaca taatgcctat ggatattact ccacatggc     480
aacagctgaa ggccttctaa agcgtggaga tggtaaggac agaccttttg tcttgtccag    540
agcattcttt gctggaagtc aaaggtatgg agcagtctgg actggtgata attcggcaga    600
ttgggatcat ctcagggttt cagtcccaat ggttttgacg cttggtctta ctggaatgac    660
attctctggg gctgatgttg gtggattttt tggcaatcct gagcctgagt tattagtgcg    720
ttggtatcaa cttggtgctt attatccttt ctttagaggt catgctcatc atgacacaaa    780
aagacgagag ccttggttgt ttggtgaacg aaataccgca cttatgagag atgccatacg    840
aattcgttac accttgcttc catacttcta cacattattc agagaagcaa atgttagtgg    900
tgttcctgtt gtacggccat tatggatgga gttcccatct gatgaagcag cttcagcaa     960
tgatgaagcc ttcatggttg ggaacagtct tttagtacaa gggatctata ctgcaagggc   1020
taaacatgca tcagtatatt tgcctgggaa ggaatcgtgg tacgacctta gaacaggaac   1080
tgcatataag ggaggaaagg tccataaact tgaagtttca gaagagagca ttcctgcttt   1140
ccaaagagct ggcacaatag tgccaagaaa agaccggttc cgtagaagct ccacacaaat   1200
ggtgcatgat ccttacacac tggtaatagc tctgaacagt tcccaagcag ctgaaggtga   1260
actctatgtt gatgatggaa aaagctatga cttcaaacat ggggcataca tccatcgccg   1320
ctttgtgttc tcgaatgggc atctaacatc ctctcccgtt ggcaactcta ggttttcgtc   1380
tgactgcatt atcgagcggg ttattcttct tggatttacc cctggggcta aaactgctct   1440
tgtcgaacca ggaaatcaga aggctgaaat cgaacttggt ccacttcggt tcgggggaca   1500
acatgctgct gttgctgtaa ccatccggaa gcctggtgtg agggtggctg aagattggaa   1560
gataaaaatt ttgtaggatg tctatttagt tcggtgaaaa tgtaatgcca agtaaagctc   1620
tcctgctact tcgttattct cgactttta gagtttatga tggagaaaac tggaaagccg    1680
ttgacatttc cttcgttcaa tttactttct acttttaaga atttaaaaaa aaagtcgacg   1740
cggccgcgaa ttccggaccg gtacctgcag gcg                                1773
```

<210> SEQ ID NO 5
<211> LENGTH: 621
<212> TYPE: PRT
<213> ORGANISM: Arabidopsis thaliana

<400> SEQUENCE: 5

```
Met Tyr Gly Arg Asp Pro Trp Gly Gly Pro Leu Glu Ile Asn Thr Ala
1               5                   10                  15

Asp Ser Ala Thr Asp Asp Arg Ser Arg Asn Leu Asn Asp Leu Asp
            20                  25                  30

Arg Ala Ala Leu Ser Arg Pro Leu Asp Glu Thr Gln Gln Ser Trp Leu
        35                  40                  45

Leu Gly Pro Thr Glu Gln Lys Lys Lys Tyr Val Asp Leu Gly Cys
    50                  55                  60

Ile Ile Val Ser Arg Lys Ile Phe Val Trp Thr Val Gly Thr Leu Val
65                  70                  75                  80

Ala Ala Ala Leu Leu Ala Gly Phe Ile Thr Leu Ile Val Lys Thr Val
                85                  90                  95

Pro Arg His His Pro Lys Thr Pro Pro Pro Asp Asn Tyr Thr Ile Ala
            100                 105                 110
```

```
Leu His Lys Ala Leu Lys Phe Phe Asn Ala Gln Lys Ser Gly Lys Leu
            115                 120                 125

Pro Lys His Asn Asn Val Ser Trp Arg Gly Asn Ser Gly Leu Gln Asp
        130                 135                 140

Gly Lys Gly Glu Thr Gly Ser Phe Tyr Lys Asp Leu Val Gly Gly Tyr
145                 150                 155                 160

Tyr Asp Ala Gly Asp Ala Ile Lys Phe Asn Phe Pro Met Ala Tyr Ala
                165                 170                 175

Met Thr Met Leu Ser Trp Ser Val Ile Glu Tyr Ser Ala Lys Tyr Glu
            180                 185                 190

Ala Ala Gly Glu Leu Thr His Val Lys Glu Leu Ile Lys Trp Gly Thr
        195                 200                 205

Asp Tyr Phe Leu Lys Thr Phe Asn Ser Thr Ala Asp Ser Ile Asp Asp
210                 215                 220

Leu Val Ser Gln Val Gly Ser Gly Asn Thr Asp Asp Gly Asn Thr Asp
225                 230                 235                 240

Pro Asn Asp His Tyr Cys Trp Met Arg Pro Glu Asp Met Asp Tyr Lys
                245                 250                 255

Arg Pro Val Thr Thr Cys Asn Gly Gly Cys Ser Asp Leu Ala Ala Glu
            260                 265                 270

Met Ala Ala Ala Leu Ala Ser Ala Ser Ile Val Phe Lys Asp Asn Lys
        275                 280                 285

Glu Tyr Ser Lys Lys Leu Val His Gly Ala Lys Val Val Tyr Gln Phe
        290                 295                 300

Gly Arg Thr Arg Arg Gly Arg Tyr Ser Ala Gly Thr Ala Glu Ser Ser
305                 310                 315                 320

Lys Phe Tyr Asn Ser Ser Met Tyr Trp Asp Glu Phe Ile Trp Gly Gly
                325                 330                 335

Ala Trp Met Tyr Tyr Ala Thr Gly Asn Val Thr Tyr Leu Asn Leu Ile
            340                 345                 350

Thr Gln Pro Thr Met Ala Lys His Ala Gly Ala Phe Trp Gly Gly Pro
        355                 360                 365

Tyr Tyr Gly Val Phe Ser Trp Asp Asn Lys Leu Ala Gly Ala Gln Leu
370                 375                 380

Leu Leu Ser Arg Leu Arg Leu Phe Leu Ser Pro Gly Tyr Pro Tyr Glu
385                 390                 395                 400

Glu Ile Leu Arg Thr Phe His Asn Gln Thr Ser Ile Val Met Cys Ser
                405                 410                 415

Tyr Leu Pro Ile Phe Asn Lys Phe Asn Arg Thr Asn Gly Gly Leu Ile
            420                 425                 430

Glu Leu Asn His Gly Ala Pro Gln Pro Leu Gln Tyr Ser Val Asn Ala
        435                 440                 445

Ala Phe Leu Ala Thr Leu Tyr Ser Asp Tyr Leu Asp Ala Ala Asp Thr
450                 455                 460

Pro Gly Trp Tyr Cys Gly Pro Asn Phe Tyr Ser Thr Ser Val Leu Arg
465                 470                 475                 480

Asp Phe Ala Arg Ser Gln Ile Asp Tyr Ile Leu Gly Lys Asn Pro Arg
                485                 490                 495

Lys Met Ser Tyr Val Val Gly Phe Gly Thr Lys Tyr Pro Arg His Val
            500                 505                 510

His His Arg Gly Ala Ser Ile Pro Lys Asn Lys Val Lys Tyr Asn Cys
        515                 520                 525

Lys Gly Gly Trp Lys Trp Arg Asp Ser Lys Lys Pro Asn Pro Asn Thr
```

```
                    530                 535                 540
Ile Glu Gly Ala Met Val Ala Gly Pro Asp Lys Arg Asp Gly Tyr Arg
545                 550                 555                 560

Asp Val Arg Met Asn Tyr Asn Tyr Thr Glu Pro Thr Leu Ala Gly Asn
                565                 570                 575

Ala Gly Leu Val Ala Ala Leu Val Ala Leu Ser Gly Glu Glu Glu Ala
                580                 585                 590

Thr Gly Lys Ile Asp Lys Asn Thr Ile Phe Ser Ala Val Pro Pro Leu
                595                 600                 605

Phe Pro Thr Pro Pro Pro Pro Ala Pro Trp Lys Pro
610                 615                 620

<210> SEQ ID NO 6
<211> LENGTH: 619
<212> TYPE: PRT
<213> ORGANISM: cotton

<400> SEQUENCE: 6

Met Tyr Gly Arg Asp Pro Trp Gly Gly Pro Leu Glu Ile Asn Ala Thr
1               5                   10                  15

Asp Ser Ala Thr Asp Asp Arg Ser Arg Asn Leu Gln Asp Leu Asp
            20                  25                  30

Arg Ala Ala Leu Ser Arg Pro Leu Asp Glu Thr Gln Gln Ser Trp Leu
            35                  40                  45

Leu Gly Pro Gly Glu Gln Lys Lys Lys Lys Tyr Val Asp Leu Gly
        50                  55                  60

Cys Ile Ile Val Ser Arg Lys Ile Phe Val Trp Thr Val Gly Thr Leu
65                  70                  75                  80

Leu Val Ser Ala Leu Leu Ala Gly Leu Ile Thr Leu Ile Val Lys Thr
                85                  90                  95

Val Pro Arg His His His Arg His Ser Pro Pro Asp Asn Tyr Thr Leu
            100                 105                 110

Ala Leu His Lys Ala Leu Met Phe Phe Asn Ala Gln Arg Ser Gly Lys
            115                 120                 125

Leu Pro Lys His Asn Asn Val Ser Trp Arg Gly Asn Ser Gly Leu Gln
            130                 135                 140

Asp Gly Lys Ser Asp Pro Ser Val Leu Met Lys Asp Leu Val Gly Gly
145                 150                 155                 160

Tyr Tyr Asp Ala Gly Asp Ala Ile Lys Phe Asn Phe Pro Ala Ser Phe
                165                 170                 175

Ser Met Thr Met Leu Ser Trp Ser Val Ile Glu Tyr Ser Ala Lys Tyr
            180                 185                 190

Glu Ala Ala Gly Glu Leu Asn His Val Lys Glu Ile Ile Lys Trp Gly
            195                 200                 205

Thr Asp Tyr Leu Leu Lys Thr Phe Asn Asn Thr Ala Asp Thr Ile Asp
        210                 215                 220

Arg Ile Ala Ala Gln Val Gly Ile Gly Asp Thr Ser Gly Gly Ser Ser
225                 230                 235                 240

Ala Pro Asn Asp His Tyr Cys Trp Met Arg Pro Glu Asp Ile Asp Tyr
                245                 250                 255

Pro Arg Pro Val Tyr Glu Cys His Ser Cys Ser Asp Leu Ala Ala Glu
            260                 265                 270

Met Ala Ala Ala Leu Ala Ser Ala Ser Ile Val Phe Lys Asp Asn Lys
            275                 280                 285

Ala Tyr Ser Gln Lys Leu Val His Gly Ala Arg Thr Leu Phe Met Phe
```

```
                    290                 295                 300
Ala Arg Asp Gln Arg Gly Arg Tyr Ser Ala Gly Gly Ser Asp Pro Ala
305                 310                 315                 320

Leu Phe Tyr Asn Ser Ser Tyr Trp Asp Glu Phe Val Trp Gly Gly
                325                 330                 335

Ala Trp Leu Tyr Tyr Ala Thr Gly Asn Ser Ser Tyr Leu Gln Leu Ala
                340                 345                 350

Thr His Pro Lys Leu Ala Lys His Ala Gly Ala Phe Trp Gly Gly Pro
                355                 360                 365

Asp Tyr Gly Val Leu Ser Trp Asp Asn Lys Leu Ala Gly Ala Gln Val
            370                 375                 380

Leu Leu Ser Arg Leu Arg Leu Phe Leu Ser Pro Gly Tyr Pro Tyr Glu
385                 390                 395                 400

Glu Ile Leu Ser Thr Phe His Asn Gln Thr Ser Ile Ile Met Cys Ser
                    405                 410                 415

Phe Leu Pro Val Phe Thr Ser Phe Asn Arg Thr Lys Gly Gly Leu Ile
                420                 425                 430

Gln Leu Asn His Gly Arg Pro Gln Pro Leu Gln Tyr Val Val Asn Ala
                435                 440                 445

Ala Phe Leu Ala Ala Leu Tyr Ser Asp Tyr Leu Asp Thr Ala Asp Thr
                450                 455                 460

Pro Gly Trp Tyr Cys Gly Pro Asn Phe Tyr Ser Thr Asp Val Leu Arg
465                 470                 475                 480

Glu Phe Ala Lys Thr Gln Ile Asp Tyr Ile Leu Gly Lys Asn Pro Arg
                    485                 490                 495

Lys Met Ser Tyr Val Val Gly Phe Gly Asn His Tyr Pro Lys His Val
                500                 505                 510

His His Arg Gly Ala Ser Ile Pro Lys Asn Lys Ile Lys Tyr Asn Cys
            515                 520                 525

Lys Gly Gly Trp Lys Trp Arg Asp Thr Ser Lys Pro Asn Pro Asn Thr
530                 535                 540

Leu Val Gly Ala Met Val Ala Gly Pro Asp Lys His Asp Gly Phe Arg
545                 550                 555                 560

Asp Val Arg Thr Asn Tyr Asn Tyr Thr Glu Pro Thr Leu Ala Gly Asn
                    565                 570                 575

Ala Gly Leu Val Ala Ala Leu Val Ala Leu Ser Gly Asp Lys Ala Thr
                580                 585                 590

Val Ile Asp Lys Asn Thr Ile Phe Ser Ala Val Pro Pro Met Phe Pro
            595                 600                 605

Thr Pro Pro Pro Pro Pro Ala Pro Trp Lys Pro
    610                 615

<210> SEQ ID NO 7
<211> LENGTH: 921
<212> TYPE: PRT
<213> ORGANISM: Arabidopsis thaliana

<400> SEQUENCE: 7

Met Arg Ser Leu Leu Phe Val Leu Ser Leu Ile Cys Phe Cys Ser Gln
1               5                   10                  15

Thr Ala Leu Ser Trp Lys Lys Glu Glu Phe Arg Ser Cys Asp Gln Thr
                20                  25                  30

Pro Phe Cys Lys Arg Ala Arg Ser Arg Thr Pro Gly Ala Cys Ser Leu
            35                  40                  45

Ile Val Gly Asp Val Ser Ile Thr Asp Gly Asp Leu Val Ala Lys Leu
```

```
            50                  55                  60
Leu Pro Lys Ala Pro Asn Gln Gly Asp Gly Asp Gln Ile Lys Pro Leu
 65                  70                  75                  80

Ile Leu Ser Leu Ser Val Tyr Lys Asp Gly Ile Val Arg Leu Lys Ile
                 85                  90                  95

Asp Glu Asp His Ser Leu Asn Pro Pro Lys Lys Arg Phe Gln Val Pro
                100                 105                 110

Asp Val Val Ser Glu Phe Glu Lys Lys Ile Trp Leu Gln Lys
            115                 120                 125

Val Ala Thr Glu Thr Ile Ser Gly Asp Thr Ser Pro Ser Ser Val Val
130                 135                 140

Tyr Val Ser Asp Gly Tyr Glu Ala Val Val Arg His Asp Pro Phe Glu
145                 150                 155                 160

Val Tyr Val Arg Glu Lys Ser Gly Asp Arg Arg Val Val Ser Leu
                165                 170                 175

Asn Ser His Gly Leu Phe Asp Phe Glu Gln Leu Gly Arg Lys Thr Glu
                180                 185                 190

Gly Asp Asn Trp Glu Glu Lys Phe Arg Thr His Thr Asp Ser Arg Pro
                195                 200                 205

Ser Gly Pro Gln Ser Ile Ser Phe Asp Val Ser Phe Tyr Asp Ser Ser
210                 215                 220

Phe Val Tyr Gly Ile Pro Glu His Ala Thr Ser Phe Ala Leu Lys Pro
225                 230                 235                 240

Thr Lys Gly Pro Gly Val Glu Glu Ser Glu Pro Tyr Arg Leu Phe Asn
                245                 250                 255

Leu Asp Val Phe Glu Tyr Asp His Glu Ser Pro Phe Gly Leu Tyr Gly
                260                 265                 270

Ser Ile Pro Phe Met Val Ser His Gly Lys Ser Gly Lys Thr Ser Gly
                275                 280                 285

Phe Phe Trp Leu Asn Ala Ala Glu Met Gln Ile Asp Val Leu Ala Asn
                290                 295                 300

Gly Trp Asp Ala Glu Ser Gly Ile Ser Leu Pro Ser Ser His Ser Arg
305                 310                 315                 320

Ile Asp Thr Phe Trp Met Ser Glu Ala Gly Ile Val Asp Thr Phe Phe
                325                 330                 335

Phe Val Gly Pro Glu Pro Lys Asp Val Lys Gln Tyr Ala Ser Val
                340                 345                 350

Thr Gly Thr Ser Ala Met Pro Gln Leu Phe Ala Thr Gly Tyr His Gln
                355                 360                 365

Cys Arg Trp Asn Tyr Lys Asp Glu Glu Asp Val Ala Gln Val Asp Ser
370                 375                 380

Lys Phe Asp Glu His Asp Ile Pro Tyr Asp Val Leu Trp Leu Asp Ile
385                 390                 395                 400

Glu His Thr Asp Gly Lys Arg Tyr Phe Thr Trp Asp Ser Val Leu Phe
                405                 410                 415

Pro His Pro Glu Glu Met Gln Lys Lys Leu Ala Ala Lys Gly Arg Lys
                420                 425                 430

Met Val Thr Ile Val Asp Pro His Ile Lys Arg Asp Asp Ser Tyr Phe
                435                 440                 445

Leu His Lys Glu Ala Thr Gln Met Gly Tyr Tyr Val Lys Asp Ser Ser
    450                 455                 460

Gly Lys Asp Phe Asp Gly Trp Cys Trp Pro Gly Ser Ser Tyr Ile
465                 470                 475                 480
```

```
Asp Met Leu Ser Pro Glu Ile Arg Lys Trp Trp Gly Arg Phe Ser
            485                 490                 495

Tyr Lys Asn Tyr Val Gly Ser Thr Pro Ser Leu Tyr Thr Trp Asn Asp
            500                 505                 510

Met Asn Glu Pro Ser Val Phe Asn Gly Pro Glu Val Thr Met Pro Arg
            515                 520                 525

Asp Ala Leu His Val Gly Gly Val Glu His Arg Glu Val His Asn Ala
            530                 535                 540

Tyr Gly Tyr Tyr Phe His Met Ala Thr Ser Asp Gly Leu Val Met Arg
545                 550                 555                 560

Glu Glu Gly Lys Asp Arg Pro Phe Val Leu Ser Arg Ala Ile Phe Pro
                565                 570                 575

Gly Thr Gln Arg Tyr Gly Ala Ile Trp Thr Gly Asp Asn Thr Ala Glu
            580                 585                 590

Trp Glu His Leu Arg Val Ser Ile Pro Met Ile Leu Thr Leu Gly Leu
            595                 600                 605

Thr Gly Ile Thr Phe Ser Gly Ala Asp Ile Gly Gly Phe Phe Gly Asn
            610                 615                 620

Pro Glu Pro Glu Leu Leu Val Arg Trp Tyr Gln Val Gly Ala Tyr Tyr
625                 630                 635                 640

Pro Phe Phe Arg Gly His Ala His His Asp Thr Lys Arg Arg Glu Pro
                645                 650                 655

Trp Leu Phe Gly Glu Arg Asn Thr Glu Leu Met Arg Asp Ala Ile His
            660                 665                 670

Thr Arg Tyr Thr Leu Leu Pro Tyr Phe Tyr Thr Leu Phe Arg Glu Ala
            675                 680                 685

Asn Val Thr Gly Val Pro Val Val Arg Pro Leu Trp Met Glu Phe Pro
690                 695                 700

Gln Asp Glu Ala Thr Phe Ser Asn Asp Glu Ala Phe Met Val Gly Ser
705                 710                 715                 720

Gly Leu Leu Val Gln Gly Val Tyr Thr Lys Gly Thr Thr Gln Ala Ser
                725                 730                 735

Val Tyr Leu Pro Gly Lys Glu Ser Trp Tyr Asp Leu Arg Asn Gly Lys
            740                 745                 750

Thr Tyr Val Gly Gly Lys Thr His Lys Met Asp Ala Pro Glu Glu Ser
            755                 760                 765

Ile Pro Ala Phe Gln Lys Ala Gly Thr Ile Ile Pro Arg Lys Asp Arg
            770                 775                 780

Phe Arg Arg Ser Ser Ser Gln Met Asp Asn Asp Pro Tyr Thr Leu Val
785                 790                 795                 800

Val Ala Leu Asn Ser Ser Gln Glu Ala Glu Gly Glu Leu Tyr Ile Asp
                805                 810                 815

Asp Gly Lys Ser Phe Glu Phe Arg Arg Gly Ser Tyr Ile His Arg Arg
            820                 825                 830

Phe Val Phe Ser Lys Gly Val Leu Thr Ser Thr Asn Leu Ala Pro Pro
            835                 840                 845

Glu Ala Arg Leu Ser Ser Gln Cys Leu Ile Asp Arg Ile Ile Leu Leu
            850                 855                 860

Gly His Ser Ser Gly Pro Lys Ser Ala Leu Val Glu Pro Leu Asn Gln
865                 870                 875                 880

Lys Ala Glu Ile Glu Met Gly Pro Leu Arg Met Gly Gly Leu Val Ala
                885                 890                 895

Ser Ser Gly Thr Lys Val Leu Thr Ile Arg Lys Pro Gly Val Arg Val
            900                 905                 910
```

```
Asp Gln Asp Trp Thr Val Lys Ile Leu
        915                 920

<210> SEQ ID NO 8
<211> LENGTH: 524
<212> TYPE: PRT
<213> ORGANISM: cotton

<400> SEQUENCE: 8

Tyr Asp Val Leu Trp Leu Asp Ile Glu His Thr Asp Gly Lys Arg Tyr
1               5                   10                  15

Phe Thr Trp Asp Lys Met Leu Phe Pro His Pro Glu Glu Met Gln Arg
            20                  25                  30

Lys Leu Ala Ala Lys Gly Arg His Met Val Thr Ile Val Asp Pro His
        35                  40                  45

Ile Lys Arg Asp Glu Ser Phe His Leu His Lys Asp Ala Ser Gln Arg
    50                  55                  60

Gly Tyr Tyr Val Lys Asp Ala Thr Gly Lys Asp Tyr Asp Gly Trp Cys
65                  70                  75                  80

Trp Pro Gly Ser Ser Tyr Pro Asp Met Leu Asn Pro Glu Ile Arg
            85                  90                  95

Ser Trp Trp Ala Glu Lys Phe Ser Tyr Asp Asn Tyr Val Gly Ser Thr
            100                 105                 110

Pro Ser Leu Tyr Ile Trp Asn Asp Met Asn Glu Pro Ser Val Phe Asn
            115                 120                 125

Gly Pro Glu Val Thr Met Pro Arg Asp Ala Leu His Val Gly Gly Val
        130                 135                 140

Glu His Arg Glu Leu His Asn Ala Tyr Gly Tyr Tyr Phe His Met Ala
145                 150                 155                 160

Thr Ala Glu Gly Leu Leu Lys Arg Gly Asp Gly Lys Asp Arg Pro Phe
                165                 170                 175

Val Leu Ser Arg Ala Phe Phe Ala Gly Ser Gln Arg Tyr Gly Ala Val
            180                 185                 190

Trp Thr Gly Asp Asn Ser Ala Asp Trp Asp His Leu Arg Val Ser Val
        195                 200                 205

Pro Met Val Leu Thr Leu Gly Leu Thr Gly Met Thr Phe Ser Gly Ala
    210                 215                 220

Asp Val Gly Gly Phe Gly Asn Pro Glu Pro Glu Leu Leu Val Arg
225                 230                 235                 240

Trp Tyr Gln Leu Gly Ala Tyr Tyr Pro Phe Phe Arg Gly His Ala His
                245                 250                 255

His Asp Thr Lys Arg Arg Glu Pro Trp Leu Phe Gly Glu Arg Asn Thr
            260                 265                 270

Ala Leu Met Arg Asp Ala Ile Arg Ile Arg Tyr Thr Leu Leu Pro Tyr
        275                 280                 285

Phe Tyr Thr Leu Phe Arg Glu Ala Asn Val Ser Gly Val Pro Val Val
    290                 295                 300

Arg Pro Leu Trp Met Glu Phe Pro Ser Asp Glu Ala Ala Phe Ser Asn
305                 310                 315                 320

Asp Glu Ala Phe Met Val Gly Asn Ser Leu Leu Val Gln Gly Ile Tyr
                325                 330                 335

Thr Ala Arg Ala Lys His Ala Ser Val Tyr Leu Pro Gly Lys Glu Ser
            340                 345                 350

Trp Tyr Asp Leu Arg Thr Gly Thr Ala Tyr Lys Gly Gly Lys Val His
        355                 360                 365
```

```
Lys Leu Glu Val Ser Glu Ser Ile Pro Ala Phe Gln Arg Ala Gly
    370                 375                 380

Thr Ile Val Pro Arg Lys Asp Arg Phe Arg Arg Ser Ser Thr Gln Met
385                 390                 395                 400

Val His Asp Pro Tyr Thr Leu Val Ile Ala Leu Asn Ser Ser Gln Ala
                405                 410                 415

Ala Glu Gly Glu Leu Tyr Val Asp Asp Gly Lys Ser Tyr Asp Phe Lys
            420                 425                 430

His Gly Ala Tyr Ile His Arg Arg Phe Val Phe Ser Asn Gly His Leu
        435                 440                 445

Thr Ser Ser Pro Val Gly Asn Ser Arg Phe Ser Ser Asp Cys Ile Ile
    450                 455                 460

Glu Arg Val Ile Leu Leu Gly Phe Thr Pro Gly Ala Lys Thr Ala Leu
465                 470                 475                 480

Val Glu Pro Gly Asn Gln Lys Ala Glu Ile Glu Leu Gly Pro Leu Arg
                485                 490                 495

Phe Gly Gly Gln His Ala Ala Val Ala Val Thr Ile Arg Lys Pro Gly
            500                 505                 510

Val Arg Val Ala Glu Asp Trp Lys Ile Lys Ile Leu
        515                 520

<210> SEQ ID NO 9
<211> LENGTH: 2766
<212> TYPE: DNA
<213> ORGANISM: Arabidopsis thaliana

<400> SEQUENCE: 9
atgagatctc ttctctttgt actatcactc atttgctttt gctctcaaac agcactttca        60
tggaagaagg aagagtttcg cagctgtgac caaactccat tttgtaaacg cgctcgatct       120
cgtactcccg gcgcgtgttc tctaattgtc ggcgatgttt ccatcactga tggagatctc       180
gtagcgaagc ttctaccgaa agcgcctaat caaggcgatg gggatcagat caagccgttg       240
attctttctc tctcagttta caaggatggg atcgtgcggc ttaaaatcga tgaggaccat       300
tcgttgaacc cgccgaagaa gaggttccaa gttcctgatg tggtagtgtc tgagtttgag       360
gagaagaaga tctggctgca gaaagtagcg acggagacga tctctggaga cactagtccg       420
tcttcagtag tttatgtatc cgatggttac gaggcggtgg tgcgacacga tccgtttgag       480
gtgtatgtgc gtgagaaatc aggtgatcgc cgtcgcgttg tgtcattgaa ttctcatgga       540
ttatttgatt ttgagcagtt ggggaggaaa actgaaggag ataactggga agagaaattt       600
aggactcata cagattctag accatctggt cctcaatcta ttagtttcga tgtttcgttt       660
tatgattcca gtttcgttta tggaattcct gaacacgcca ctagcttcgc gttgaagcct       720
accaagggtc ctggagttga ggaatctgaa ccctacaggc tttttaatct agatgtgttt       780
gaatacgatc atgaatcacc gtttgggctt acgggtcga ttccgttcat ggtttcgcat       840
gggaagtctg gtaaaacttc aggatttttc tggttgaatg ctgcggaaat gcagattgat       900
gtgttggcta tggttgggac tgcagagagt ggtatttctt gccttctag tcacagtagg       960 atcgacacat tctggatgag cgaggcaggg attgtggata cattctttt cgttgggcct      1020 gagccaaagg atgttgtaaa gcagtatgca agtgtgacag tacttcagc catgcctcag      1080 ttgtttgcca ctggttatca tcaatgtagg tggaactaca agatgagga ggatgtggca      1140 caggtggact cgaaattcga tgaacacgat attccttatg atgttctctg gcttgacatt      1200
gagcatacag atgggaagag atactttaca tgggatagtg tgttgtttcc tcatccagag      1260
```

```
gagatgcaaa agaaattggc tgcaaagggt aggaagatgg tgaccattgt ggatcctcat    1320
atcaagaggg atgactcata cttcttacac aaagaggcta ctcagatggg atactatgtt    1380
aaggattcat ctggaaaaga ctttgatggt tggtgctggc ctggttcatc atcttacatt    1440
gatatgttga gcccagagat tagaaaatgg tggggtggga ggttctcgta taagaactat    1500
gttggttcaa ctccatcatt gtacacctgg aatgacatga atgagccttc tgtattcaat    1560
ggtcccgagg ttactatgcc aagagatgca ttacatgttg ggggtgttga acacagagaa    1620
gttcataacg catatggata ttacttccac atggcgactt ccgatggact tgttatgcgt    1680
gaagaaggaa aggataggcc ttttgtattg tcaagagcaa tctttcccgg cactcaaaga    1740
tacggagcaa tttggactgg agataacaca gccgaatggg aacaccttag agtctccatt    1800
ccaatgatat tgacacttgg tcttactgga attacattct ctggagctga tattggtggg    1860
ttttttggaa atcctgaacc agaacttcta gttaggtggt accaagtggg tgcttactat    1920
ccatttttca ggggtcatgc tcatcacgat accaaaagac gagagccttg gttgtttggt    1980
gaacggaaca cagaactcat gagagatgcc atacacactc gttacacact gctcccatac    2040
ttctacacgt tgttcagaga agcaaacgtt acgggtgttc ctgttgtacg cccattatgg    2100
atggaattcc cgcaagatga agctactttt agcaacgatg aagccttcat ggtcggtagt    2160
ggtctactgg ttcaaggagt ttacaccaag gaacaacgc aagcttccgt gtatttgcct    2220
ggcaaagaat catggtatga cttgagaaac ggtaagactt acgttggagg caagactcac    2280
aagatggatg ctccagagga gagtattcct gcgtttcaaa aggcaggaac catcatccca    2340
aggaaggacc ggtttaggcg aagttcctct caaatggaca atgatcctta ctttggtg     2400 gtagctttga acagttctca agaagcagaa ggtgaactct acatcgatga cggcaaaagc    2460
tttgaattca gacgaggctc ttacatccat cgtcgcttcg tcttctcaaa gggtgttctt    2520
acatcaacga acttagctcc tccagaagct cgtctctctt cccaatgctt gatcgacaga    2580
attatcctct tgggacacag ctcaggtcca aaatctgcgt tggtggaacc gttgaatcaa    2640
aaggcagaga ttgagatggg acctctgcga atgggtgggc ttgtagcttc ctcgggtaca    2700
aaggtgttga ctatccgcaa accgggtgtt cgagtggacc aagactggac cgtaaagatt    2760
ctgtga                                                               2766
```

<210> SEQ ID NO 10  
<211> LENGTH: 29  
<212> TYPE: DNA  
<213> ORGANISM: Artificial sequence  
<220> FEATURE:  
<223> OTHER INFORMATION: oligonucleotide PCR primer

<400> SEQUENCE: 10
ccgctcgagc gggcattttc cgcccacta                                      29

<210> SEQ ID NO 11  
<211> LENGTH: 29  
<212> TYPE: DNA  
<213> ORGANISM: Artificial Sequence  
<220> FEATURE:  
<223> OTHER INFORMATION: oligonucleotide PCR primer

<400> SEQUENCE: 11
cgggatcccg tcacacatgg acagaagaa                                      29

<210> SEQ ID NO 12  
<211> LENGTH: 19

```
<212> TYPE: DNA
<213> ORGANISM: Artificial Sequence
<220> FEATURE:
<223> OTHER INFORMATION: oligonucleotide PCR primer

<400> SEQUENCE: 12
gacggcgtct agaagattc                                            19

<210> SEQ ID NO 13
<211> LENGTH: 19
<212> TYPE: DNA
<213> ORGANISM: Artificial Sequence
<220> FEATURE:
<223> OTHER INFORMATION: oligonucleotide PCR primer

<400> SEQUENCE: 13
taacttatcg ggcttctgc                                            19

<210> SEQ ID NO 14
<211> LENGTH: 21
<212> TYPE: DNA
<213> ORGANISM: Artificial Sequence
<220> FEATURE:
<223> OTHER INFORMATION: oligonucleotide PCR primer

<400> SEQUENCE: 14
ccctcgcttg gtacaaggta t                                         21

<210> SEQ ID NO 15
<211> LENGTH: 21
<212> TYPE: DNA
<213> ORGANISM: Artificial Sequence
<220> FEATURE:
<223> OTHER INFORMATION: oligonucleotide PCR primer

<400> SEQUENCE: 15
tcctgatcct ctcaccacgt a                                         21

<210> SEQ ID NO 16
<211> LENGTH: 21
<212> TYPE: DNA
<213> ORGANISM: Artificial Sequence
<220> FEATURE:
<223> OTHER INFORMATION: oligonucleotide PCR primer

<400> SEQUENCE: 16
cgtagtggtc tactggttca a                                         21

<210> SEQ ID NO 17
<211> LENGTH: 21
<212> TYPE: DNA
<213> ORGANISM: Artificial Sequence
<220> FEATURE:
<223> OTHER INFORMATION: oligonucleotide PCR primer

<400> SEQUENCE: 17
tgagctgtgt cccaagagga t                                         21

<210> SEQ ID NO 18
<211> LENGTH: 21
<212> TYPE: DNA
<213> ORGANISM: Artificial Sequence
<220> FEATURE:
<223> OTHER INFORMATION: oligonucleotide PCR primer

<400> SEQUENCE: 18
ggtgatgagg ataccagcga t                                         21
```

```
<210> SEQ ID NO 19
<211> LENGTH: 21
<212> TYPE: DNA
<213> ORGANISM: Artificial Sequence
<220> FEATURE:
<223> OTHER INFORMATION: oligonucleotide PCR primer

<400> SEQUENCE: 19
cccactccct aaccggagtt t                                            21

<210> SEQ ID NO 20
<211> LENGTH: 35
<212> TYPE: DNA
<213> ORGANISM: Artificial Sequence
<220> FEATURE:
<223> OTHER INFORMATION: oligonucleotide PCR primer

<400> SEQUENCE: 20
ccgctcgagc ggtttcactc acaactgtgg tctct                             35

<210> SEQ ID NO 21
<211> LENGTH: 34
<212> TYPE: DNA
<213> ORGANISM: Artificial Sequence
<220> FEATURE:
<223> OTHER INFORMATION: oligonucleotide PCR primer

<400> SEQUENCE: 21
ccgctcgagc ggtctcctaa gtcctaaccc cata                              34

<210> SEQ ID NO 22
<211> LENGTH: 21
<212> TYPE: DNA
<213> ORGANISM: Artificial Sequence
<220> FEATURE:
<223> OTHER INFORMATION: oligonucleotide PCR primer

<400> SEQUENCE: 22
cgggatgaag aggatgtaga g                                            21

<210> SEQ ID NO 23
<211> LENGTH: 21
<212> TYPE: DNA
<213> ORGANISM: Artificial Sequence
<220> FEATURE:
<223> OTHER INFORMATION: oligonucleotide PCR primer

<400> SEQUENCE: 23
gaacccctga gatgatccca a                                            21

<210> SEQ ID NO 24
<211> LENGTH: 617
<212> TYPE: PRT
<213> ORGANISM: tomato

<400> SEQUENCE: 24

Met Tyr Gly Arg Asp Pro Trp Gly Gly Pro Leu Glu Ile His Thr Ala
1               5                   10                  15

Asp Ser Ala Thr Asp Asp Arg Ser Arg Asn Leu Gln Asp Phe Asp
            20                  25                  30

Arg Ala Ala Met Ser Arg Ser Leu Asp Glu Thr Gln Gln Ser Trp Leu
        35                  40                  45

Leu Gly Pro Thr Glu Gln Lys Lys Lys Tyr Val Asp Leu Gly Cys
    50                  55                  60
```

```
Ile Ile Val Ser Arg Lys Ile Phe Lys Trp Thr Val Gly Cys Ile Ile
65                  70                  75                  80

Ala Ala Ala Leu Leu Ala Gly Phe Ile Thr Met Ile Val Lys Leu Val
                85                  90                  95

Pro Arg His Lys His His Asn Pro Pro Asp Asn Tyr Thr Leu Ala
            100                 105                 110

Leu Arg Lys Ala Leu Met Phe Phe Asn Ala Gln Lys Ser Gly Lys Leu
                115                 120                 125

Pro Lys His Asn Asn Val Ser Trp Arg Gly Asn Ser Cys Leu Gln Asp
            130                 135                 140

Gly Lys Ser Asp Asp Ser Thr Met Phe Lys Asn Leu Val Gly Gly Tyr
145                 150                 155                 160

Tyr Asp Ala Gly Asp Ala Ile Lys Phe Asn Phe Pro Gln Ser Phe Ala
                165                 170                 175

Leu Thr Met Leu Ser Trp Ser Val Ile Glu Tyr Ser Ala Lys Tyr Glu
                180                 185                 190

Ala Ala Gly Glu Leu Ala His Val Lys Asp Thr Ile Lys Trp Gly Thr
                195                 200                 205

Asp Tyr Leu Leu Lys Thr Phe Asn Ser Ser Ala Asp Thr Ile Asp Arg
210                 215                 220

Ile Ala Ala Gln Val Gly Lys Gly Asp Thr Thr Gly Gly Ala Thr Asp
225                 230                 235                 240

Pro Asn Asp His Tyr Cys Trp Val Arg Pro Glu Asp Ile Asp Tyr Ala
                245                 250                 255

Arg Pro Val Thr Glu Cys His Gly Cys Ser Asp Leu Ala Ala Glu Met
                260                 265                 270

Ala Ala Ala Leu Ala Ser Ala Ser Ile Val Phe Lys Asp Asn Lys Ala
                275                 280                 285

Tyr Ser Gln Lys Leu Val His Gly Ala Arg Thr Leu Phe Lys Phe Ser
290                 295                 300

Arg Asp Gln Arg Gly Arg Tyr Ser Val Gly Asn Glu Ala Glu Thr Phe
305                 310                 315                 320

Tyr Asn Ser Thr Gly Tyr Trp Asp Glu Phe Ile Trp Gly Ala Ala Trp
                325                 330                 335

Leu Tyr Tyr Ala Thr Gly Asn Ser Ser Tyr Leu Gln Leu Ala Thr Thr
                340                 345                 350

Pro Gly Ile Ala Lys His Ala Gly Ala Phe Trp Gly Gly Pro Asp Tyr
                355                 360                 365

Gly Val Leu Ser Trp Asp Asn Lys Leu Thr Gly Ala Gln Val Leu Leu
370                 375                 380

Ser Arg Met Arg Leu Phe Leu Ser Pro Gly Tyr Pro Tyr Glu Glu Ile
385                 390                 395                 400

Leu Arg Thr Phe His Asn Gln Thr Ser Ile Ile Met Cys Ser Tyr Leu
                405                 410                 415

Pro Ile Phe Thr Ser Phe Asn Arg Thr Lys Gly Gly Leu Ile Gln Leu
                420                 425                 430

Asn His Gly Arg Pro Gln Pro Leu Gln Tyr Val Val Asn Ala Ala Phe
                435                 440                 445

Leu Ala Thr Leu Phe Ser Asp Tyr Leu Ala Ala Asp Thr Pro Gly
                450                 455                 460

Trp Tyr Cys Gly Pro Asn Phe Tyr Ser Thr Asp Val Leu Arg Lys Phe
465                 470                 475                 480

Ala Glu Thr Gln Ile Asp Tyr Ile Leu Gly Lys Asn Pro Arg Lys Met
```

-continued

```
                  485                 490                 495
Ser Tyr Val Val Gly Phe Gly Asn His Tyr Pro Lys His Val His
                500                 505                 510

Arg Gly Ala Ser Ile Pro Lys Asn Lys Val Lys Tyr Asn Cys Lys Gly
            515                 520                 525

Gly Trp Lys Tyr Arg Asp Ser Ser Lys Ala Asn Pro Asn Thr Ile Val
        530                 535                 540

Gly Ala Met Val Ala Gly Pro Asp Lys His Asp Gly Phe Arg Asp Val
545                 550                 555                 560

Arg Ser Asn Tyr Asn Tyr Thr Glu Pro Thr Leu Ala Gly Asn Ala Gly
                565                 570                 575

Leu Val Ala Ala Leu Val Ala Leu Ser Gly Asp Arg Asp Val Gly Ile
            580                 585                 590

Asp Lys Asn Thr Leu Phe Ser Ala Val Pro Pro Met Phe Pro Thr Pro
        595                 600                 605

Pro Pro Pro Pro Ala Pro Trp Lys Pro
    610                 615

<210> SEQ ID NO 25
<211> LENGTH: 621
<212> TYPE: PRT
<213> ORGANISM: Brassica

<400> SEQUENCE: 25

Met Tyr Gly Arg Asp Pro Trp Gly Gly Pro Leu Glu Ile His Ala Thr
1               5                   10                  15

Asp Ser Ala Thr Asp Asp Asp Arg Ser Arg Asn Leu Asn Asp Ile Asp
            20                  25                  30

Arg Ala Ala Leu Ser Arg Pro Leu Asp Glu Thr Gln Gln Ser Trp Leu
        35                  40                  45

Leu Gly Pro Thr Glu Gln Lys Lys Lys Tyr Val Asp Leu Gly Cys
    50                  55                  60

Ile Ile Val Ser Arg Lys Ile Phe Val Trp Thr Val Gly Thr Ile Val
65                  70                  75                  80

Ala Ala Ala Leu Leu Ala Gly Phe Ile Thr Leu Ile Val Lys Thr Val
                85                  90                  95

Pro Arg His His Arg Lys Thr Pro Pro Asp Asn Tyr Thr Ile Ala
            100                 105                 110

Leu His Lys Ala Leu Lys Phe Phe Asn Ala Gln Lys Ser Gly Lys Leu
        115                 120                 125

Pro Arg His Asn Asn Val Ser Trp Arg Gly Asn Ser Gly Leu Gln Asp
    130                 135                 140

Gly Lys Gly Asp Ser Gly Ser Phe Tyr Lys Asp Leu Val Gly Gly Tyr
145                 150                 155                 160

Tyr Asp Ala Gly Asp Ala Ile Lys Phe Asn Phe Pro Met Ala Tyr Ala
                165                 170                 175

Met Thr Met Leu Ser Trp Ser Val Ile Glu Tyr Ser Ala Lys Tyr Glu
            180                 185                 190

Ala Ala Gly Glu Leu Val His Val Lys Glu Leu Ile Lys Trp Gly Thr
        195                 200                 205

Asp Tyr Phe Leu Lys Thr Phe Asn Ser Thr Ala Asp Ser Ile Asp Asp
    210                 215                 220

Leu Val Ser Gln Val Gly Ser Gly Asn Thr Asp Asp Gly Ser Thr Asp
225                 230                 235                 240

Pro Asn Asp His Tyr Cys Trp Met Arg Pro Glu Asp Met Asp Tyr Lys
```

```
                        245                 250                 255
Arg Pro Val Thr Thr Cys Asn Gly Gly Cys Ser Asp Leu Ala Ala Glu
            260                 265                 270

Met Ala Ala Ala Leu Ala Ser Ala Ser Ile Val Phe Lys Asp Asn Arg
        275                 280                 285

Glu Tyr Ser Lys Lys Leu Val His Gly Ala Lys Thr Val Tyr Gln Phe
    290                 295                 300

Gly Arg Thr Arg Arg Gly Arg Tyr Ser Ala Gly Thr Ala Glu Ser Ala
305                 310                 315                 320

Lys Phe Tyr Asn Ser Ser Met Tyr Trp Asp Glu Phe Ile Trp Gly Gly
            325                 330                 335

Ala Trp Leu Tyr Tyr Ala Thr Gly Asn Val Thr Tyr Leu Asp Leu Ile
        340                 345                 350

Thr Lys Pro Thr Met Ala Lys His Ala Gly Ala Phe Trp Gly Gly Pro
    355                 360                 365

Tyr Tyr Gly Val Phe Ser Trp Asp Asn Lys Leu Ala Gly Ala Gln Leu
370                 375                 380

Leu Leu Ser Arg Leu Arg Leu Phe Leu Ser Pro Gly Tyr Pro Tyr Glu
385                 390                 395                 400

Glu Ile Val Arg Thr Phe His Asn Gln Thr Ser Ile Val Met Cys Ser
            405                 410                 415

Tyr Leu Pro Tyr Phe Asn Lys Phe Asn Arg Thr Arg Gly Gly Leu Ile
        420                 425                 430

Glu Leu Asn His Gly Asp Pro Gln Pro Leu Gln Tyr Ala Ala Asn Ala
    435                 440                 445

Ala Phe Leu Ala Thr Leu Tyr Ser Asp Tyr Leu Asp Ala Ala Asp Thr
450                 455                 460

Pro Gly Trp Tyr Cys Gly Pro Asn Phe Tyr Ser Thr Asn Val Leu Arg
465                 470                 475                 480

Glu Phe Ala Arg Thr Gln Ile Asp Tyr Ile Leu Gly Lys Asn Pro Arg
            485                 490                 495

Lys Met Ser Tyr Leu Val Gly Phe Gly Thr Lys Tyr Pro Lys His Val
        500                 505                 510

His His Arg Gly Ala Ser Ile Pro Lys Asn Lys Val Lys Tyr Asn Cys
    515                 520                 525

Lys Gly Gly Trp Lys Trp Arg Asp Ser Lys Lys Pro Asn Pro Asn Thr
530                 535                 540

Ile Glu Gly Ala Met Val Ala Gly Pro Asp Lys Arg Asp Gly Phe Arg
545                 550                 555                 560

Asp Val Arg Thr Asn Tyr Asn Tyr Thr Glu Pro Thr Leu Ala Gly Asn
            565                 570                 575

Ala Gly Leu Val Ala Ala Leu Val Ala Leu Ser Gly Glu Glu Glu Ala
        580                 585                 590

Ser Gly Thr Ile Asp Lys Asn Thr Ile Phe Ser Ala Val Pro Pro Leu
    595                 600                 605

Phe Pro Thr Pro Pro Pro Pro Ala Pro Trp Lys Pro
610                 615                 620

<210> SEQ ID NO 26
<211> LENGTH: 921
<212> TYPE: PRT
<213> ORGANISM: Arabidopsis thaliana

<400> SEQUENCE: 26

Met Arg Ser Leu Leu Phe Val Leu Ser Leu Ile Cys Phe Cys Ser Gln
```

-continued

```
1               5              10              15
Thr Ala Leu Ser Trp Lys Lys Glu Glu Phe Arg Ser Cys Asp Gln Thr
            20                  25                  30

Pro Phe Cys Lys Arg Ala Arg Ser Arg Thr Pro Gly Ala Cys Ser Leu
            35                  40                  45

Ile Val Gly Asp Val Ser Ile Thr Asp Gly Asp Leu Val Ala Lys Leu
50                  55                  60

Leu Pro Lys Ala Pro Asn Gln Gly Asp Gln Ile Lys Pro Leu
65                  70                  75                  80

Ile Leu Ser Leu Ser Val Tyr Lys Asp Gly Ile Val Arg Leu Lys Ile
                    85                  90                  95

Asp Glu Asp His Ser Leu Asn Pro Pro Lys Lys Arg Phe Gln Val Pro
                    100                 105                 110

Asp Val Val Ser Glu Phe Glu Glu Lys Lys Ile Trp Leu Gln Lys
                115                 120                 125

Val Ala Thr Glu Thr Ile Ser Gly Asp Thr Ser Pro Ser Ser Val Val
            130                 135                 140

Tyr Val Ser Asp Gly Tyr Glu Ala Val Val Arg His Asp Pro Phe Glu
145                 150                 155                 160

Val Tyr Val Arg Glu Lys Ser Gly Asp Arg Arg Val Val Ser Leu
                    165                 170                 175

Asn Ser His Gly Leu Phe Asp Phe Glu Gln Leu Gly Arg Lys Thr Glu
                180                 185                 190

Gly Asp Asn Trp Glu Glu Lys Phe Arg Thr His Thr Asp Ser Arg Pro
            195                 200                 205

Ser Gly Pro Gln Ser Ile Ser Phe Asp Val Ser Phe Tyr Asp Ser Ser
210                 215                 220

Phe Val Tyr Gly Ile Pro Glu His Ala Thr Ser Phe Ala Leu Lys Pro
225                 230                 235                 240

Thr Lys Gly Pro Gly Val Glu Glu Ser Glu Pro Tyr Arg Leu Phe Asn
                245                 250                 255

Leu Asp Val Phe Glu Tyr Asp His Glu Ser Pro Phe Gly Leu Tyr Gly
            260                 265                 270

Ser Ile Pro Phe Met Val Ser His Gly Lys Ser Gly Lys Thr Ser Gly
        275                 280                 285

Phe Phe Trp Leu Asn Ala Ala Glu Met Gln Ile Asp Val Leu Ala Asn
    290                 295                 300

Gly Trp Asp Ala Glu Ser Gly Ile Ser Leu Pro Ser Ser His Ser Arg
305                 310                 315                 320

Ile Asp Thr Phe Trp Met Ser Glu Ala Gly Ile Val Asp Thr Phe Phe
                325                 330                 335

Phe Val Gly Pro Glu Pro Lys Asp Val Val Lys Gln Tyr Ala Ser Val
            340                 345                 350

Thr Gly Thr Ser Ala Met Pro Gln Leu Phe Ala Thr Gly Tyr His Gln
        355                 360                 365

Cys Arg Trp Asn Tyr Lys Asp Glu Glu Asp Val Ala Gln Val Asp Ser
370                 375                 380

Lys Phe Asp Glu His Asp Ile Pro Tyr Asp Val Leu Trp Leu Asp Ile
385                 390                 395                 400

Glu His Thr Asp Gly Lys Arg Tyr Phe Thr Trp Asp Ser Val Leu Phe
                    405                 410                 415

Pro His Pro Glu Glu Met Gln Lys Leu Ala Ala Lys Gly Arg Lys
                420                 425                 430
```

-continued

```
Met Val Thr Ile Val Asp Pro His Ile Lys Arg Asp Ser Tyr Phe
            435                 440                 445
Leu His Lys Glu Ala Thr Gln Met Gly Tyr Tyr Val Lys Asp Ser Ser
465 450                 455                 460
Gly Lys Asp Phe Asp Gly Trp Cys Trp Pro Gly Ser Ser Ser Tyr Ile
465                 470                 475                 480
Asp Met Leu Ser Pro Glu Ile Arg Lys Trp Trp Gly Arg Phe Ser
                485                 490                 495
Tyr Lys Asn Tyr Val Gly Ser Thr Pro Ser Leu Tyr Thr Trp Asn Asp
                500                 505                 510
Met Asn Glu Pro Ser Val Phe Asn Gly Pro Glu Val Thr Met Pro Arg
            515                 520                 525
Asp Ala Leu His Val Gly Gly Val Glu His Arg Glu Val His Asn Ala
        530                 535                 540
Tyr Gly Tyr Tyr Phe His Met Ala Thr Ser Asp Gly Leu Val Met Arg
545                 550                 555                 560
Glu Glu Gly Lys Asp Arg Pro Phe Val Leu Ser Arg Ala Ile Phe Pro
                565                 570                 575
Gly Thr Gln Arg Tyr Gly Ala Ile Trp Thr Gly Asp Asn Thr Ala Glu
            580                 585                 590
Trp Glu His Leu Arg Val Ser Ile Pro Met Ile Leu Thr Leu Gly Leu
            595                 600                 605
Thr Gly Ile Thr Phe Ser Gly Ala Asp Ile Gly Gly Phe Phe Gly Asn
        610                 615                 620
Pro Glu Pro Glu Leu Leu Val Arg Trp Tyr Gln Val Gly Ala Tyr Tyr
625                 630                 635                 640
Pro Phe Phe Arg Gly His Ala His His Asp Thr Lys Arg Arg Glu Pro
                645                 650                 655
Trp Leu Phe Gly Glu Arg Asn Thr Glu Leu Met Arg Asp Ala Ile His
                660                 665                 670
Thr Arg Tyr Thr Leu Leu Pro Tyr Phe Tyr Thr Leu Phe Arg Glu Ala
            675                 680                 685
Asn Val Thr Gly Val Pro Val Val Arg Pro Leu Trp Met Glu Phe Pro
            690                 695                 700
Gln Asp Glu Ala Thr Phe Ser Asn Asp Glu Ala Phe Met Val Gly Ser
705                 710                 715                 720
Gly Leu Leu Val Gln Gly Val Tyr Thr Lys Gly Thr Thr Gln Ala Ser
                725                 730                 735
Val Tyr Leu Pro Gly Lys Glu Ser Trp Tyr Asp Leu Arg Asn Gly Lys
            740                 745                 750
Thr Tyr Val Gly Gly Lys Thr His Lys Met Asp Ala Pro Glu Glu Ser
            755                 760                 765
Ile Pro Ala Phe Gln Lys Ala Gly Thr Ile Ile Pro Arg Lys Asp Arg
        770                 775                 780
Phe Arg Arg Ser Ser Ser Gln Met Asp Asn Asp Pro Tyr Thr Leu Val
785                 790                 795                 800
Val Ala Leu Asn Ser Ser Gln Glu Ala Glu Gly Glu Leu Tyr Ile Asp
                805                 810                 815
Asp Gly Lys Ser Phe Glu Phe Arg Arg Gly Ser Tyr Ile His Arg Arg
            820                 825                 830
Phe Val Phe Ser Lys Gly Val Leu Thr Ser Thr Asn Leu Ala Pro Pro
        835                 840                 845
Glu Ala Arg Leu Ser Ser Gln Cys Leu Ile Asp Arg Ile Ile Leu Leu
850                 855                 860
```

```
Gly His Ser Ser Gly Pro Lys Ser Ala Leu Val Glu Pro Leu Asn Gln
865                 870                 875                 880

Lys Ala Glu Ile Glu Met Gly Pro Leu Arg Met Gly Leu Val Ala
            885                 890                 895

Ser Ser Gly Thr Lys Val Leu Thr Ile Arg Lys Pro Gly Val Arg Val
            900                 905                 910

Asp Gln Asp Trp Thr Val Lys Ile Leu
            915                 920
```

<210> SEQ ID NO 27
<211> LENGTH: 919
<212> TYPE: PRT
<213> ORGANISM: potato

<400> SEQUENCE: 27

```
Met Arg Ala Pro Leu Leu Tyr Pro Leu Leu Leu Leu Leu Leu Leu Phe
1               5                   10                  15

Val Thr Ser Ala Tyr Ser Trp Lys Lys Glu Glu Phe Arg Asn Cys Asp
                20                  25                  30

Gln Thr Pro Phe Cys Lys Arg Ala Arg Ser Arg Lys Pro Gly Ser Cys
            35                  40                  45

Asn Leu Arg Val Ala Asp Val Ser Ile Ser Asp Gly Asp Leu Ile Ala
50                  55                  60

Lys Leu Val Pro Lys Glu Glu Asn Pro Glu Ser Gln Pro Asn Lys
65                  70                  75                  80

Pro Leu Val Leu Thr Leu Ser Val Tyr Gln Asp Gly Val Met Arg Val
                85                  90                  95

Lys Ile Asp Glu Asp Gln Asn Leu Asn Pro Pro Lys Lys Arg Phe Glu
            100                 105                 110

Val Pro Glu Val Ile Glu Glu Asp Phe Leu Asn Thr Lys Leu Trp Leu
        115                 120                 125

Thr Arg Val Lys Glu Glu Gln Ile Asp Gly Val Ser Ser Phe Ser Ser
    130                 135                 140

Val Phe Tyr Leu Ser Asp Gly Tyr Gly Val Leu Arg His Asp Pro
145                 150                 155                 160

Phe Glu Val Phe Ala Arg Glu Ser Gly Ser Gly Lys Arg Val Leu Ser
                165                 170                 175

Ile Asn Ser Asn Gly Leu Phe Asp Phe Glu Gln Leu Arg Glu Lys Lys
            180                 185                 190

Glu Gly Asp Asp Trp Glu Glu Lys Phe Arg Ser His Thr Asp Thr Arg
        195                 200                 205

Pro Tyr Gly Pro Gln Ser Ile Ser Phe Asp Val Ser Phe Tyr Gly Ala
    210                 215                 220

Asp Phe Val Tyr Gly Ile Pro Glu His Ala Thr Ser Phe Ala Leu Lys
225                 230                 235                 240

Pro Thr Lys Gly Pro Asn Val Glu Glu Tyr Ser Glu Pro Tyr Arg Leu
                245                 250                 255

Phe Asn Leu Asp Val Phe Glu Tyr Leu His Glu Ser Pro Phe Gly Leu
            260                 265                 270

Tyr Gly Ser Ile Pro Phe Met Ile Ser His Gly Lys Ala Arg Gly Ser
        275                 280                 285

Ser Gly Phe Phe Trp Leu Asn Ala Ala Glu Met Gln Ile Asp Val Leu
    290                 295                 300

Gly Ser Gly Trp Asn Ser Asp Glu Ser Ser Lys Ile Met Leu Pro Ser
305                 310                 315                 320
```

```
Asp Lys His Arg Ile Asp Thr Leu Trp Met Ser Glu Ser Gly Val Val
                325                 330                 335

Asp Thr Phe Phe Phe Ile Gly Pro Gly Pro Lys Asp Val Val Arg Gln
                340                 345                 350

Tyr Thr Ser Val Thr Gly Arg Pro Ser Met Pro Gln Leu Phe Ala Thr
                355                 360                 365

Ala Tyr His Gln Cys Arg Trp Asn Tyr Arg Asp Glu Glu Asp Val Tyr
                370                 375                 380

Asn Val Asp Ser Lys Phe Asp Glu His Asp Ile Pro Tyr Asp Val Leu
385                 390                 395                 400

Trp Leu Asp Ile Glu His Thr Asp Gly Lys Lys Tyr Phe Thr Trp Asp
                405                 410                 415

Arg Val Leu Phe Pro Asn Pro Glu Glu Met Gln Lys Lys Leu Ala Ala
                420                 425                 430

Lys Gly Arg His Met Val Thr Ile Val Asp Pro His Ile Lys Arg Asp
                435                 440                 445

Glu Ser Tyr His Ile Pro Lys Glu Ala Leu Glu Lys Gly Tyr Tyr Val
                450                 455                 460

Lys Asp Ala Thr Gly Lys Asp Tyr Asp Gly Trp Cys Trp Pro Gly Ser
465                 470                 475                 480

Ser Ser Tyr Thr Asp Leu Leu Asn Pro Glu Ile Lys Ser Trp Trp Ser
                485                 490                 495

Asp Lys Phe Ser Leu Asp Ser Tyr Val Gly Ser Thr Lys Tyr Leu Tyr
                500                 505                 510

Ile Trp Asn Asp Met Asn Glu Pro Ser Val Phe Asn Gly Pro Glu Val
                515                 520                 525

Thr Met Pro Arg Asp Ala Leu His His Gly Gly Val Glu His Arg Glu
                530                 535                 540

Leu His Asn Ser Tyr Gly Tyr Tyr Phe His Met Gly Thr Ser Asp Gly
545                 550                 555                 560

Leu Leu Lys Arg Gly Asp Gly Lys Asp Arg Pro Phe Val Leu Ala Arg
                565                 570                 575

Ala Phe Phe Ala Gly Ser Gln Arg Tyr Gly Ala Ile Trp Thr Gly Asp
                580                 585                 590

Asn Thr Ala Glu Trp Glu His Leu Arg Val Ser Val Pro Met Val Leu
                595                 600                 605

Thr Leu Ser Ile Ser Gly Ile Val Phe Ser Gly Ala Asp Val Gly Gly
                610                 615                 620

Phe Phe Gly Asn Pro Asp Thr Glu Leu Leu Val Arg Trp Tyr Gln Val
625                 630                 635                 640

Gly Ala Tyr Tyr Pro Phe Phe Arg Gly His Ala His His Asp Thr Lys
                645                 650                 655

Arg Arg Glu Pro Trp Leu Phe Gly Glu Arg Asn Thr Gln Leu Met Arg
                660                 665                 670

Glu Ala Ile His Val Arg Tyr Met Tyr Leu Pro Tyr Phe Tyr Thr Leu
                675                 680                 685

Phe Arg Glu Ala Asn Ser Ser Gly Thr Pro Val Ala Arg Pro Leu Trp
                690                 695                 700

Met Glu Phe Pro Gly Asp Glu Lys Ser Phe Ser Asn Asp Glu Ala Phe
705                 710                 715                 720

Met Val Gly Asn Gly Leu Leu Val Gln Gly Val Tyr Thr Glu Lys Pro
                725                 730                 735

Lys His Val Ser Val Tyr Leu Pro Gly Glu Glu Ser Trp Tyr Asp Leu
```

```
                            740                 745                 750
Arg Ser Ala Ser Ala Tyr Asn Gly Gly His Thr His Lys Tyr Glu Val
            755                 760                 765

Ser Glu Asp Ser Ile Pro Ser Phe Gln Arg Ala Gly Thr Ile Ile Pro
            770                 775                 780

Arg Lys Asp Arg Leu Arg Arg Ser Ser Thr Gln Met Glu Asn Asp Pro
785                 790                 795                 800

Tyr Thr Leu Val Ile Ala Leu Asn Ser Ser Lys Ala Ala Glu Gly Glu
            805                 810                 815

Leu Tyr Ile Asp Asp Gly Lys Ser Tyr Glu Phe Lys Gln Gly Ala Phe
            820                 825                 830

Ile Leu Lys Trp Glu Ala Tyr Ile Phe Gln Met Gln Pro Arg Leu Gln
            835                 840                 845

Leu Ala Val Thr His Phe Pro Ser Glu Cys Thr Val Glu Arg Ile Ile
            850                 855                 860

Leu Leu Gly Leu Ser Pro Gly Ala Lys Thr Ala Leu Ile Glu Pro Gly
865                 870                 875                 880

Asn Lys Lys Val Glu Ile Glu Leu Gly Pro Leu Phe Ile Gln Gly Asn
            885                 890                 895

Arg Gly Ser Val Pro Thr Ile Arg Lys Pro Asn Val Arg Ile Thr Asp
            900                 905                 910

Asp Trp Ser Ile Gln Ile Leu
            915

<210> SEQ ID NO 28
<211> LENGTH: 966
<212> TYPE: PRT
<213> ORGANISM: mouse

<400> SEQUENCE: 28

Met Ala Ala Ile Ala Ala Val Ala Ala Arg Arg Arg Ser Trp Leu
1               5                   10                  15

Ser Leu Val Leu Ala Tyr Leu Gly Val Cys Leu Gly Ile Thr Leu Ala
            20                  25                  30

Val Asp Arg Ser Asn Phe Lys Thr Cys Asp Glu Ser Ser Phe Cys Lys
        35                  40                  45

Arg Gln Arg Ser Ile Arg Pro Gly Leu Ser Pro Tyr Arg Ala Leu Leu
    50                  55                  60

Asp Thr Leu Gln Leu Gly Pro Asp Ala Leu Thr Val His Leu Ile His
65                  70                  75                  80

Glu Val Thr Lys Val Leu Leu Val Leu Glu Leu Gln Gly Leu Gln Lys
                85                  90                  95

Asn Met Thr Arg Ile Arg Ile Asp Glu Leu Glu Pro Arg Arg Pro Arg
            100                 105                 110

Tyr Arg Val Pro Asp Val Leu Val Ala Asp Pro Pro Thr Ala Arg Leu
            115                 120                 125

Ser Val Ser Gly Arg Asp Asp Asn Ser Val Glu Leu Thr Val Ala Glu
    130                 135                 140

Gly Pro Tyr Lys Ile Ile Leu Thr Ala Gln Pro Phe Arg Leu Asp Leu
145                 150                 155                 160

Leu Glu Asp Arg Ser Leu Leu Leu Ser Val Asn Ala Arg Gly Leu Met
                165                 170                 175

Ala Phe Glu His Gln Arg Ala Pro Arg Val Pro Phe Ser Asp Lys Val
            180                 185                 190

Ser Leu Ala Leu Gly Ser Val Trp Asp Lys Ile Lys Asn Leu Phe Ser
```

```
            195                 200                 205
Arg Gln Glu Ser Lys Asp Pro Ala Glu Gly Asn Gly Ala Gln Pro Glu
    210                 215                 220

Ala Thr Pro Gly Asp Gly Asp Lys Pro Glu Glu Thr Gln Glu Lys Ala
225                 230                 235                 240

Glu Lys Asp Glu Pro Gly Ala Trp Glu Glu Thr Phe Lys Thr His Ser
                245                 250                 255

Asp Ser Lys Pro Tyr Gly Pro Thr Ser Val Gly Leu Asp Phe Ser Leu
            260                 265                 270

Pro Gly Met Glu His Val Tyr Gly Ile Pro Glu His Ala Asp Ser Leu
        275                 280                 285

Arg Leu Lys Val Thr Glu Gly Glu Pro Tyr Arg Leu Tyr Asn Leu
    290                 295                 300

Asp Val Phe Gln Tyr Glu Leu Asn Asn Pro Met Ala Leu Tyr Gly Ser
305                 310                 315                 320

Val Pro Val Leu Leu Ala His Ser Phe His Arg Asp Leu Gly Ile Phe
                325                 330                 335

Trp Leu Asn Ala Ala Glu Thr Trp Val Asp Ile Ser Ser Asn Thr Ala
            340                 345                 350

Gly Lys Thr Leu Phe Gly Lys Met Leu Asp Tyr Leu Gln Gly Ser Gly
        355                 360                 365

Glu Thr Pro Gln Thr Asp Ile Arg Trp Met Ser Glu Ser Gly Ile Ile
    370                 375                 380

Asp Val Phe Leu Met Leu Gly Pro Ser Val Phe Asp Val Phe Arg Gln
385                 390                 395                 400

Tyr Ala Ser Leu Thr Gly Thr Gln Ala Leu Pro Pro Leu Phe Ser Leu
                405                 410                 415

Gly Tyr His Gln Ser Arg Trp Asn Tyr Arg Asp Glu Ala Asp Val Leu
            420                 425                 430

Glu Val Asp Gln Gly Phe Asp Asp His Asn Met Pro Cys Asp Val Ile
        435                 440                 445

Trp Leu Asp Ile Glu His Ala Asp Gly Lys Arg Tyr Phe Thr Trp Asp
    450                 455                 460

Pro Thr Arg Phe Pro Gln Pro Leu Asn Met Leu Glu His Leu Ala Ser
465                 470                 475                 480

Lys Arg Arg Lys Leu Val Ala Ile Val Asp Pro His Ile Lys Val Asp
                485                 490                 495

Ser Gly Tyr Arg Val His Glu Glu Leu Arg Asn His Gly Leu Tyr Val
            500                 505                 510

Lys Thr Arg Asp Gly Ser Asp Tyr Glu Gly Trp Cys Trp Pro Gly Ser
        515                 520                 525

Ala Ser Tyr Pro Asp Phe Thr Asn Pro Arg Met Arg Ala Trp Trp Ser
    530                 535                 540

Asn Met Phe Ser Phe Asp Asn Tyr Glu Gly Ser Ala Pro Asn Leu Tyr
545                 550                 555                 560

Val Trp Asn Asp Met Asn Glu Pro Ser Val Phe Asn Gly Pro Glu Val
                565                 570                 575

Thr Met Leu Lys Asp Ala Val His Tyr Gly Gly Trp Glu His Arg Asp
            580                 585                 590

Ile His Asn Ile Tyr Gly Leu Tyr Val His Met Ala Thr Ala Asp Gly
        595                 600                 605

Leu Ile Gln Arg Ser Gly Gly Ile Glu Arg Pro Phe Val Leu Ser Arg
    610                 615                 620
```

```
Ala Phe Phe Ser Gly Ser Gln Arg Phe Gly Ala Val Trp Thr Gly Asp
625                 630                 635                 640

Asn Thr Ala Glu Trp Asp His Leu Lys Ile Ser Ile Pro Met Cys Leu
            645                 650                 655

Ser Leu Ala Leu Val Gly Leu Ser Phe Cys Gly Ala Asp Val Gly Gly
        660                 665                 670

Phe Phe Lys Asn Pro Glu Pro Glu Leu Leu Val Arg Trp Tyr Gln Met
    675                 680                 685

Gly Ala Tyr Gln Pro Phe Phe Arg Ala His Ala His Leu Asp Thr Gly
690                 695                 700

Arg Arg Glu Pro Trp Leu Leu Ala Ser Gln Tyr Gln Asp Ala Ile Arg
705                 710                 715                 720

Asp Ala Leu Phe Gln Arg Tyr Ser Leu Leu Pro Phe Trp Tyr Thr Leu
                725                 730                 735

Phe Tyr Gln Ala His Lys Glu Gly Phe Pro Val Met Arg Pro Leu Trp
            740                 745                 750

Val Gln Tyr Pro Glu Asp Met Ser Thr Phe Ser Ile Glu Asp Gln Phe
        755                 760                 765

Met Leu Gly Asp Ala Leu Leu Ile His Pro Val Ser Asp Ala Gly Ala
    770                 775                 780

His Gly Val Gln Val Tyr Leu Pro Gly Gln Glu Glu Val Trp Tyr Asp
785                 790                 795                 800

Ile Gln Ser Tyr Gln Lys His His Gly Pro Gln Thr Leu Tyr Leu Pro
                805                 810                 815

Val Thr Leu Ser Ser Ile Pro Val Phe Gln Arg Gly Thr Ile Val
            820                 825                 830

Pro Arg Trp Met Arg Val Arg Arg Ser Ser Asp Cys Met Lys Asp Asp
        835                 840                 845

Pro Ile Thr Leu Phe Val Ala Leu Ser Pro Gln Gly Thr Ala Gln Gly
    850                 855                 860

Glu Leu Phe Leu Asp Asp Gly His Thr Phe Asn Tyr Gln Thr Arg His
865                 870                 875                 880

Glu Phe Leu Leu Arg Arg Phe Ser Phe Ser Gly Ser Thr Leu Val Ser
                885                 890                 895

Ser Ser Ala Asp Pro Lys Gly His Leu Glu Thr Pro Ile Trp Ile Glu
            900                 905                 910

Arg Val Val Ile Met Gly Ala Gly Lys Pro Ala Ala Val Val Leu Gln
        915                 920                 925

Thr Lys Gly Ser Pro Glu Ser Arg Leu Ser Phe Gln His Asp Pro Glu
    930                 935                 940

Thr Ser Val Leu Ile Leu Arg Lys Pro Gly Val Ser Val Ala Ser Asp
945                 950                 955                 960

Trp Ser Ile His Leu Arg
                965

<210> SEQ ID NO 29
<211> LENGTH: 923
<212> TYPE: PRT
<213> ORGANISM: yeast

<400> SEQUENCE: 29

Met Arg Tyr His Gly Ile Cys Trp Phe Ile Phe Gln Ala Ala Ile Ile
1               5                   10                  15

Phe Ala Ile Phe Gly Ser Cys Gln Gly Ala Phe Arg His Gln Phe Lys
            20                  25                  30
```

-continued

Thr Ala Glu Gln Asp Gly Phe Ala Arg Arg Asn Arg Asp Leu Ala Lys
                35                  40                  45

Phe Gln Lys Glu Asn Leu Asn Trp Asn Gly Leu Phe Gln Leu Asn Ser
 50                  55                  60

Ile Ser Tyr Asn Ser Gly Val Val Ser Gly Val Phe Glu Gln Gln Ser
 65                  70                  75                  80

Glu Asn Gly Glu Asn Gln His Leu Phe Pro Phe Ser Ile Ser Phe Leu
                 85                  90                  95

Lys Asn Asp Val Val Arg Phe Gln Met Asp Glu Lys Ser Arg Leu Glu
            100                 105                 110

Gly Thr Val Glu Tyr Glu Lys Asn Ile Leu Thr Lys Arg Arg Phe Asp
            115                 120                 125

Ala Ser Thr Glu Leu Gly Phe Asn Glu Arg Ala Glu Val Tyr Gly Lys
        130                 135                 140

Asp Ala His Leu Leu Glu Gln Thr Ser Thr Ser Leu Thr Ile Arg Tyr
145                 150                 155                 160

Gly Ser His Gly Arg Phe Thr Val Ile Val Thr Phe Ser Pro Phe Lys
                165                 170                 175

Val Glu Phe Gln Arg Asp Gly Glu Pro Gln Val Val Leu Asn Glu Arg
            180                 185                 190

His Leu Leu Asn Met Glu Tyr Tyr Arg Pro Lys Ser Ser Arg Thr Pro
        195                 200                 205

Glu Gln Glu Ala Asn Gly Met Trp Asp Glu Thr Phe Asp Asn Phe His
210                 215                 220

Asp Ser Lys Pro Lys Gly Pro Glu Ser Val Gly Leu Asp Ile Lys Phe
225                 230                 235                 240

Val Asp Tyr Gly Asn Val Tyr Gly Val Pro Glu His Thr Ser Ser Leu
                245                 250                 255

Ser Leu Lys Glu Thr Asn Asn Ser Asp Ala Gly Tyr Thr Glu Pro Tyr
            260                 265                 270

Arg Leu Tyr Asn Val Asp Leu Phe Glu Tyr Glu Val Asp Ser Pro Met
        275                 280                 285

Ser Gln Tyr Gly Ala Ile Pro Phe Met Gln Ala His Lys Pro Asn Ser
290                 295                 300

Asp Val Ala Val Phe Trp Ser Asn Ala Ala Thr Trp Ile Asp Val
305                 310                 315                 320

Glu Lys Glu Ser Gly Pro Ser Pro His Ser Gln Ser Thr Ser Thr His
            325                 330                 335

Trp Tyr Ser Glu Ser Gly Thr Leu Asp Leu Phe Ile Phe Leu Gly Pro
        340                 345                 350

Lys Ala Ser Asp Val Tyr Glu Ser Tyr Ser Ala Leu Val Gly Arg Pro
        355                 360                 365

Leu Leu Pro Pro Leu Phe Ser Ile Gly Tyr His Gln Cys Arg Trp Asn
370                 375                 380

Tyr Val Ser Glu Glu Asp Val Leu Asn Val Asp Ala Lys Phe Asp Glu
385                 390                 395                 400

Val Asp Met Pro Tyr Asp Thr Ile Trp Leu Asp Ile Glu Tyr Ala Ser
                405                 410                 415

Lys Arg Arg Tyr Phe Thr Trp Asp Lys Ala Thr Phe Pro Asn Pro Lys
            420                 425                 430

Ala Met Leu Glu Lys Leu Asp Ser Lys Ser Arg Lys Leu Ile Val Ile
        435                 440                 445

Leu Asp Pro His Ile Lys Asn Asp Pro Asn Tyr Phe Val Ser Lys Glu
450                 455                 460

```
Leu Ile Asp Tyr Asn Tyr Ala Val Lys Asp Lys Ser Gly Val Asp Asn
465                 470                 475                 480

Tyr Asn Ala Asp Cys Trp Pro Gly Asn Ser Val Trp Val Asp Phe Phe
                485                 490                 495

Asn Pro Glu Ala Gln Ala Trp Trp Gly Ser Leu Tyr Glu Phe Asp Arg
            500                 505                 510

Phe Glu Ser Asp Lys Asn Leu Trp Ile Trp Asn Asp Met Asn Glu Pro
        515                 520                 525

Ser Val Phe Arg Gly Pro Glu Thr Ser Met His Arg Asp Ala Ile His
    530                 535                 540

Tyr Gly Gly Trp Glu His Arg Asp Ile His Asn Ile Tyr Gly His Lys
545                 550                 555                 560

Cys Ile Asn Gly Thr Tyr Asn Gly Leu Ile Lys Arg Gly Glu Gly Ala
                565                 570                 575

Val Arg Pro Phe Ile Leu Thr Arg Ser Phe Phe Ala Gly Thr Ser Ala
            580                 585                 590

Leu Ala Ala Asn Trp Ile Gly Asp Thr Met Thr Thr Trp Glu His Leu
        595                 600                 605

Arg Gly Ser Ile Pro Thr Val Leu Thr Asn Gly Ile Ser Gly Met Ala
    610                 615                 620

Phe Ser Gly Ala Asp Val Ala Gly Phe Phe Gly Asn Pro Asp Ala Glu
625                 630                 635                 640

Leu Phe Val Arg Trp Tyr Glu Thr Ala Ile Phe Tyr Pro Phe Phe Arg
                645                 650                 655

Ala His Ala His Ile Asp Thr Lys Arg Arg Glu Pro Trp Leu Tyr Gly
            660                 665                 670

Glu Pro Tyr Thr Ser Leu Val Arg Glu Leu Leu Arg Ile Arg Tyr Arg
        675                 680                 685

Leu Leu Pro Thr Trp Tyr Thr Ala Phe Tyr Asn Ser His Thr His Gly
    690                 695                 700

Phe Pro Ile Leu Tyr Pro Gln Phe Leu Met His Pro Glu Asp Glu Glu
705                 710                 715                 720

Gly Phe Ala Ile Asp Asp Gln Phe Tyr Val Gly Asp Ser Gly Leu Leu
                725                 730                 735

Val Lys Pro Val Thr His Pro Ser Ile Asp Lys Ile Thr Ile Tyr Leu
            740                 745                 750

Ala Asp Asp Glu Val Tyr Phe Asp Leu His Asp His Thr Glu Tyr Ala
        755                 760                 765

Gly Lys Gly His Gln Val Val Pro Ala Pro Leu Gly Arg Val Pro Val
    770                 775                 780

Leu Leu Arg Gly Gly Asn Ile Leu Ile Thr Arg Glu Arg Ile Arg Arg
785                 790                 795                 800

Ala Ala Glu Leu Thr Arg Asn Asp Pro Phe Thr Leu Thr Ile Ala Val
                805                 810                 815

Ser Lys Ile Gly Lys Asn Ala Ser Gly Phe Leu Tyr Leu Asp Asp Gly
            820                 825                 830

Val Thr Phe Asn Tyr Lys Lys Gly Glu Tyr Leu Ile Arg His Phe Ser
        835                 840                 845

Tyr Glu Asn Gly Ile Leu Thr Met Lys Asp Ser His Ser Asn Pro Pro
    850                 855                 860

Val Ser Pro Lys Tyr Ser Ser Gln Lys His Leu Lys Val Glu Arg
865                 870                 875                 880

Ile Asn Ile Tyr Gly Glu Gln Thr Arg Lys Ser Ile Lys Ile Arg Lys
```

```
                        885                 890                 895
Ile Ile Asp Ser Glu Val Thr Glu Trp Asp Val Ser Asp Asp Ser
                    900                 905                 910

Gly Cys Ile Arg Asn Pro Gln Leu Phe Leu Val
            915                 920

<210> SEQ ID NO 30
<211> LENGTH: 647
<212> TYPE: PRT
<213> ORGANISM: Arabidopsis thaliana

<400> SEQUENCE: 30

Met Arg Val Val Val Ile Ser Ser Phe Val Ser Val Ser Leu Gln Leu
1               5                   10                  15

Ser Phe Leu Leu Leu Leu Ala Ser Ala Ile Arg Ser Ser Ser Ser Pro
            20                  25                  30

Pro Asn Asp Pro Phe Leu Gly Ile Ser Pro Gln Asp Glu Lys Tyr Tyr
        35                  40                  45

Lys Ser Ser Ser Glu Ile Lys Cys Lys Asp Gly Ser Lys Lys Phe Thr
    50                  55                  60

Lys Ala Gln Leu Asn Asp Asp Phe Cys Asp Cys Ser Asp Gly Thr Asp
65                  70                  75                  80

Glu Pro Gly Thr Ser Ala Cys Pro Thr Gly Lys Phe Tyr Cys Arg Asn
                85                  90                  95

Ala Gly His Ser Pro Val Ile Leu Phe Ser Ser Arg Val Asn Asp Gly
            100                 105                 110

Ile Cys Asp Cys Cys Asp Gly Ser Asp Glu Tyr Asp Gly His Val Ser
        115                 120                 125

Cys Gln Asn Thr Cys Trp Glu Ala Gly Lys Ala Ala Arg Glu Asn Leu
    130                 135                 140

Lys Lys Lys Ile Glu Thr Tyr Asn Gln Gly Leu Val Ile Arg Arg Gln
145                 150                 155                 160

Glu Ile Glu Gln Ala Lys Val Gly Leu Glu Lys Asp Ala Ala Glu Leu
                165                 170                 175

Lys Lys Leu Lys Ser Glu Gln Lys Ile Leu Lys Gly Leu Val Asp Gln
            180                 185                 190

Leu Lys Asp Arg Lys Glu Gln Ile Glu Lys Val Glu Glu Lys Glu Arg
        195                 200                 205

Leu Gln Lys Glu Lys Glu Glu Lys Glu Lys Glu Ala Glu Leu Ala
    210                 215                 220

Ala Gln Gln Gly Lys Gly Asp Ala Glu Glu Lys Thr Asp Asp Ser Glu
225                 230                 235                 240

Lys Val Glu Glu Ser Ser His Asp Glu Gly Thr Pro Ala Val Ser Gln
                245                 250                 255

His Asp Glu Thr Thr His His Asp Glu Ile Gly Asn Tyr Lys Asp Tyr
            260                 265                 270

Pro Ser Asp Glu Glu Pro Ala Ala Gly Glu Pro Thr Ser Ile Leu
        275                 280                 285

Asp Glu Ala Thr His Thr Asn Pro Ala Asp Glu His Val Val Glu Arg
    290                 295                 300

Lys Glu Glu Ser Thr Ser Ser Glu Asp Ser Ser Pro Thr Asp Glu
305                 310                 315                 320

Ser Gln Asn Asp Gly Ser Ala Glu Lys Glu Glu Ser Asp Glu Val Lys
                325                 330                 335

Lys Val Glu Asp Phe Val Thr Glu Lys Lys Glu Glu Leu Ser Lys Glu
```

```
            340                 345                 350
Glu Leu Gly Arg Leu Val Ala Ser Arg Trp Thr Gly Glu Lys Ser Asp
                355                 360                 365

Lys Pro Thr Glu Ala Asp Asp Ile Pro Lys Ala Asp Asp Gln Glu Asn
            370                 375                 380

His Glu His Thr Pro Ile Thr Ala His Glu Ala Asp Glu Asp Asp Gly
385                 390                 395                 400

Phe Val Ser Asp Gly Asp Glu Asp Thr Ser Asp Gly Lys Tyr Ser
                405                 410                 415

Asp His Glu Pro Glu Asp Ser Tyr Glu Glu Glu Tyr Arg His Asp
            420                 425                 430

Ser Ser Ser Ser Tyr Lys Ser Asp Ala Asp Asp Val Asp Phe Ser
                435                 440                 445

Glu Thr Thr Ser Asn Pro Thr Trp Leu Glu Lys Ile Gln Lys Thr Val
            450                 455                 460

Lys Asn Ile Leu Leu Ala Val Asn Leu Phe Gln Thr Thr Pro Val Asp
465                 470                 475                 480

Lys Ser Glu Ala Asp Arg Val Arg Lys Glu Tyr Asp Glu Ser Ser Ser
                485                 490                 495

Lys Leu Asn Lys Ile Gln Ser Arg Ile Ser Ser Leu Glu Lys Lys Leu
            500                 505                 510

Lys Gln Asp Phe Gly Pro Glu Lys Glu Phe Tyr Ser Phe His Gly Arg
            515                 520                 525

Cys Phe Glu Ser Lys Gln Gly Lys Tyr Thr Tyr Lys Val Cys Ala Tyr
            530                 535                 540

Lys Glu Ala Thr Gln Glu Gly Tyr Ser Lys Thr Arg Leu Gly Glu
545                 550                 555                 560

Trp Asp Lys Phe Glu Asn Ser Tyr Gln Phe Met Ser Tyr Thr Asn Gly
                565                 570                 575

Glu Lys Cys Trp Asn Gly Pro Asp Arg Ser Leu Lys Val Lys Leu Arg
            580                 585                 590

Cys Gly Leu Lys Asn Glu Leu Met Asp Val Asp Glu Pro Ser Arg Cys
            595                 600                 605

Glu Tyr Ala Ala Ile Leu Ser Thr Pro Ala Arg Cys Leu Glu Asp Lys
            610                 615                 620

Leu Lys Glu Leu Gln Gln Lys Leu Glu Lys Leu Met Asn Gln Asp Lys
625                 630                 635                 640

Pro Gln Asn His Asp Glu Leu
                645

<210> SEQ ID NO 31
<211> LENGTH: 613
<212> TYPE: PRT
<213> ORGANISM: rice

<400> SEQUENCE: 31

Met Gly Leu His Ala Ile Leu Leu Leu Leu Leu Arg Ile Ser Ala
1               5                   10                  15

Ser Ala Ala Ala Ser Arg Pro Pro Leu Asp Thr Leu Gly Ile Pro Pro
                20                  25                  30

Gln Asp Glu Ala Tyr Phe Arg Gly Gly Val Ile Arg Cys Arg Asp Gly
            35                  40                  45

Ser Gly Arg Phe Ala Arg Asp Lys Leu Asn Asp Asp Phe Cys Asp Cys
        50                  55                  60

Pro Asp Gly Thr Asp Glu Pro Gly Thr Ser Ala Cys Pro Glu Gly Lys
```

```
                65                  70                  75                  80
            Phe Tyr Cys Gln Asn Ala Gly His Ser Pro Ile Thr Ile Phe Ser Ser
                            85                  90                  95
            Arg Val Asn Asp Gly Ile Cys Asp Cys Cys Asp Gly Ser Asp Glu Tyr
                        100                 105                 110
            Asp Ser Asn Val Thr Cys Lys Asn Thr Cys Trp Glu Ala Gly Lys Ala
                        115                 120                 125
            Ala Arg Asp Lys Leu Lys Lys Val Ala Thr Tyr Lys Ser Gly Val
                    130                 135                 140
            Val Ile Arg Asn Gln Glu Ile Gln Lys Ala Lys Val Ala Phe Ala Lys
            145                 150                 155                 160
            Asp Glu Ala Glu Leu Ala Lys Leu Lys Gly Glu Lys Ile Leu Gln
                        165                 170                 175
            Gly Leu Val Asp Lys Leu Thr Glu Gln Lys Lys Leu Ile Glu Lys Ala
                        180                 185                 190
            Glu Glu Glu Glu Arg Leu Arg Lys Glu Lys Glu Lys Arg Met Lys
                    195                 200                 205
            Glu Glu Ala Glu Lys Gln Ala Ala Asp Glu Lys Lys Ala Ser Asp Ala
                    210                 215                 220
            Ser Gln Glu Val Asp Ser Gln Glu Asn His Glu Thr Val Gln Glu Asp
            225                 230                 235                 240
            Glu Ser Lys Val Ala Glu His His Asp Gly His Ala Thr Ser His Asp
                        245                 250                 255
            Asn His Thr Pro Glu Ser Glu Ser Ser Val Glu Gln His Asp Pro Glu
                        260                 265                 270
            Ser Gln Asp Asp Ile Ser Ile Lys Ala Ala Pro Ala Asp Glu Ser Pro
                    275                 280                 285
            Pro Glu Glu Thr Ser Ala Ala Pro Thr Lys Glu Gln Glu Ser Thr Pro
                    290                 295                 300
            Ala Asp Ser Glu Gly Leu Ser Arg Glu Glu Leu Gly Arg Leu Val Ala
            305                 310                 315                 320
            Ser Arg Trp Thr Gly Glu Lys Val Asp Glu Val Ser Lys Asp Lys
                        325                 330                 335
            Asn Glu His Glu Ala Glu His Asp Met Pro Glu His Ser Glu Glu Thr
                        340                 345                 350
            His Glu Asp Glu Ser Asp Val Pro Glu Ser Ala Glu Asp Ser Tyr Ala
                    355                 360                 365
            Gly Tyr His Ser Glu Val Glu Asp Asp Arg His Lys Tyr Asp Asp Glu
                    370                 375                 380
            Asp Phe Ser His Glu Ser Asp Asp Glu Tyr Val Asp His Asp Glu
            385                 390                 395                 400
            His Val Ala Ser Tyr Lys Ser Asp Asp Gln Lys Gly Asp Asp His
                        405                 410                 415
            Ser Asp Phe Thr Ala Ser Gly Gln Ala Ser Trp Leu Asp Lys Ile Gln
                        420                 425                 430
            Gln Thr Val Gln Asn Val Leu Arg Thr Phe Asn Phe Lys Thr Pro
                    435                 440                 445
            Val Asp Leu Ser Glu Ala Ser Arg Val Arg Lys Glu Tyr Asp Asp Ala
                    450                 455                 460
            Ser Ser Lys Leu Ser Lys Ile Gln Ser Arg Ile Ser Thr Leu Thr Asp
            465                 470                 475                 480
            Lys Leu Lys His Asp Phe Gly Lys Glu Lys Glu Phe Tyr Tyr Phe Tyr
                        485                 490                 495
```

```
Asp Gln Cys Phe Glu Ser Lys Glu Gly Lys Tyr Val Tyr Lys Val Cys
            500                 505                 510
Pro Phe Lys Ala Ser Gln Val Glu Gly His Ser Thr Thr Ser Leu
        515                 520                 525
Gly Arg Trp Asp Lys Phe Glu Glu Ser Tyr Arg Val Met Gln Phe Ser
    530                 535                 540
Asn Gly Asp Arg Cys Trp Asn Gly Pro Asp Arg Ser Leu Lys Val Arg
545                 550                 555                 560
Leu Arg Cys Gly Leu Asn Asn Glu Leu Asn Gly Val Asp Glu Pro Ser
                565                 570                 575
Arg Cys Glu Tyr Val Ala Val Leu Ser Thr Pro Ala Leu Cys Asp Glu
            580                 585                 590
Gln Lys Leu Lys Glu Leu Glu Gln Lys Leu Lys Ala Ser Ser Asn Gln
        595                 600                 605
Arg His Asp Glu Leu
        610

<210> SEQ ID NO 32
<211> LENGTH: 521
<212> TYPE: PRT
<213> ORGANISM: mouse

<400> SEQUENCE: 32

Met Leu Leu Leu Leu Leu Leu Leu Pro Leu Cys Trp Ala Val Glu
1               5                   10                  15
Val Lys Arg Pro Arg Gly Val Ser Leu Ser Asn His His Phe Tyr Glu
            20                  25                  30
Glu Ser Lys Pro Phe Thr Cys Leu Asp Gly Thr Ala Thr Ile Pro Phe
        35                  40                  45
Asp Gln Val Asn Asp Asp Tyr Cys Asp Cys Lys Asp Gly Ser Asp Glu
    50                  55                  60
Pro Gly Thr Ala Ala Cys Pro Asn Gly Ser Phe His Cys Thr Asn Thr
65                  70                  75                  80
Gly Tyr Lys Pro Leu Tyr Ile Leu Ser Ser Arg Val Asn Asp Gly Val
                85                  90                  95
Cys Asp Cys Cys Asp Gly Thr Asp Glu Tyr Asn Ser Gly Thr Val Cys
            100                 105                 110
Glu Asn Thr Cys Arg Glu Lys Gly Arg Lys Glu Lys Glu Ser Leu Gln
        115                 120                 125
Gln Leu Ala Glu Val Thr Arg Glu Gly Phe Arg Leu Lys Lys Ile Leu
    130                 135                 140
Ile Glu Glu Trp Lys Thr Ala Arg Glu Lys Gln Ser Lys Leu Leu
145                 150                 155                 160
Glu Leu Gln Ala Gly Lys Lys Ser Leu Glu Asp Gln Val Glu Thr Leu
                165                 170                 175
Arg Ala Ala Lys Glu Glu Ala Glu Arg Pro Lys Glu Ala Lys Asp
            180                 185                 190
Gln His Arg Lys Leu Trp Glu Glu Gln Ala Ala Lys Ala Arg
        195                 200                 205
Arg Glu Gln Glu Arg Ala Ala Ser Ala Phe Gln Glu Leu Asp Asp Asn
    210                 215                 220
Met Asp Gly Met Val Ser Leu Ala Glu Leu Gln Thr His Pro Glu Leu
225                 230                 235                 240
Asp Thr Asp Gly Asp Gly Ala Leu Ser Glu Glu Glu Ala Gln Ala Leu
                245                 250                 255
```

```
Leu Ser Gly Asp Thr Gln Thr Asp Thr Thr Ser Phe Tyr Asp Arg Val
            260                 265                 270

Trp Ala Ala Ile Arg Asp Lys Tyr Arg Ser Glu Val Pro Thr Asp
        275                 280                 285

Ile Pro Val Pro Glu Glu Thr Glu Pro Lys Glu Lys Pro Pro Val
290                 295                 300

Leu Pro Pro Thr Glu Glu Glu Glu Glu Glu Glu Glu Pro Glu Glu
305                 310                 315                 320

Glu Glu Glu Glu Glu Glu Glu Glu Glu Ala Pro Pro Leu Gln
                325                 330                 335

Pro Pro Gln Pro Ser Pro Thr Glu Asp Glu Lys Met Pro Pro Tyr
            340                 345                 350

Asp Glu Glu Thr Gln Ala Ile Ile Asp Ala Ala Gln Glu Ala Arg Ser
            355                 360                 365

Lys Phe Glu Glu Val Glu Arg Ser Leu Lys Glu Met Glu Glu Ser Ile
            370                 375                 380

Arg Ser Leu Glu Gln Glu Ile Ser Phe Asp Phe Gly Pro Ser Gly Glu
385                 390                 395                 400

Phe Ala Tyr Leu Tyr Ser Gln Cys Tyr Glu Leu Thr Thr Asn Glu Tyr
                405                 410                 415

Val Tyr Arg Leu Cys Pro Phe Lys Leu Val Ser Gln Lys Pro Lys His
            420                 425                 430

Gly Gly Ser Pro Thr Ser Leu Gly Thr Trp Gly Ser Trp Ala Gly Pro
            435                 440                 445

Asp His Asp Lys Phe Ser Ala Met Lys Tyr Glu Gln Gly Thr Gly Cys
            450                 455                 460

Trp Gln Gly Pro Asn Arg Ser Thr Thr Val Arg Leu Leu Cys Gly Lys
465                 470                 475                 480

Glu Thr Val Val Thr Ser Thr Thr Glu Pro Ser Arg Cys Glu Tyr Leu
                485                 490                 495

Met Glu Leu Met Thr Pro Ala Ala Cys Pro Glu Pro Pro Glu Ala
            500                 505                 510

Pro Ser Asp Gly Asp His Asp Glu Leu
            515                 520

<210> SEQ ID NO 33
<211> LENGTH: 506
<212> TYPE: PRT
<213> ORGANISM: yeast

<400> SEQUENCE: 33

Met Lys Phe Ser Gln Trp Tyr Thr Leu Thr Ala Pro Leu Leu Ile Ser
1               5                   10                  15

Ser Leu Tyr Thr Val Asn Ala Ala Asn Asp Leu Arg Gly Val Ala Ser
                20                  25                  30

Asp Lys Ser Asp Leu Tyr Lys Pro Asp Ala Lys Gly Asn Trp Lys Cys
            35                  40                  45

Leu Gly Ser Asp Lys Leu Ile Ser Phe Asn Gln Val Asn Asp Asp Tyr
        50                  55                  60

Cys Asp Cys Pro Asp Gly Ser Asp Glu Pro Gly Thr Ser Ala Cys His
65                  70                  75                  80

Asn Gly Lys Phe Phe Cys Lys Asn Thr Gly Tyr Ile Ser Ser Tyr Ile
                85                  90                  95

Pro Ser Asn Arg Val Asp Asp Thr Val Cys Asp Cys Cys Asp Gly Ala
            100                 105                 110
```

-continued

Asp Glu Ser Leu Ile Thr Cys Pro Asn Thr Cys Ala Gln Lys Ala Arg
            115                 120                 125

Glu Tyr Leu Ala Thr Leu Glu Glu His Asn Arg Leu Val Lys Asn Gly
130                 135                 140

Leu Lys Ile Arg Glu Gln Trp Ala Leu Glu Ser Ala Lys Lys Thr Asp
145                 150                 155                 160

Glu Val Lys Ala Arg Tyr Lys Glu Ile Ser Asp Ser Leu Val Ala Val
                165                 170                 175

Ser Ala Glu Lys Thr Gln Phe Ser Glu Lys Val Glu Lys Met Lys Arg
            180                 185                 190

Ser Thr Asp Leu Gly Ala Glu Ala Val Leu Pro Ser Asp Phe Gln Asp
            195                 200                 205

Leu Arg Val Ala Leu Leu Ser Leu Val Asp Glu Arg Asn Glu Met Gln
210                 215                 220

Glu Arg Leu Asp Ile Leu Thr Asn Leu Leu Asp Glu Leu Thr Leu Leu
225                 230                 235                 240

Tyr Glu Thr Asp Lys Phe Asp Glu Thr Met Lys Glu Ala Ile Leu Ser
                245                 250                 255

Phe Glu Asp Leu Lys Glu Gln Glu Ile Arg Arg Lys Val Ser Ser Asp
            260                 265                 270

Asp Val His Asn Tyr Leu Glu Ser Cys Asn Asn His Leu Ser Met Leu
            275                 280                 285

Thr Gly Pro Ser Glu Asp Ile Thr Phe Ser Ser Leu Ile Lys Asp Ile
            290                 295                 300

Lys Lys Ile Leu Asn Ser Leu Val Trp Asn Ile Lys Leu Ser Leu Ile
305                 310                 315                 320

Asn Phe Gly Ile Leu Ser Pro Ser Ala Ser Ser Thr Pro Leu Thr Asp
                325                 330                 335

Ser Glu Ser Tyr Arg Arg Phe Glu Ala Ala Gln Arg Asp Leu Asp Ala
            340                 345                 350

Ala Glu Glu Asn Glu Lys Ser Leu Glu Lys Glu His Thr Lys Leu Met
            355                 360                 365

His Glu Leu Glu Tyr His His Gly Trp Asp Leu Tyr Arg Ala Ile Lys
            370                 375                 380

Gly Met Glu Thr Lys Arg Glu Ile Gly Gly Tyr Thr Tyr Lys Val Val
385                 390                 395                 400

Phe Tyr Glu Asn Val Phe Gln Asp Ser Ile Leu Leu Gly Asn Phe Ala
                405                 410                 415

Ser Gln Glu Gly Asn Val Leu Lys Tyr Glu Asn Gly Gln Ser Cys Trp
            420                 425                 430

Asn Gly Pro His Arg Ser Ala Ile Val Thr Val Glu Cys Gly Val Glu
            435                 440                 445

Asn Glu Ile Val Ser Val Leu Glu Ala Gln Lys Cys Glu Tyr Leu Ile
            450                 455                 460

Lys Met Lys Ser Pro Ala Ala Cys Ser Pro Asn Gln Leu Lys Gln Ser
465                 470                 475                 480

Leu Leu Asn Thr Gln Asn Ser Ala Tyr Glu Asp Ala Val Asn Gly Met
                485                 490                 495

Glu Asp Lys Glu Ser Ser Val Asp Glu Leu
            500                 505

METHODS AND MEANS FOR MODULATING CELLULOSE BIOSYNTHESIS IN FIBER PRODUCING PLANTS

FIELD OF THE INVENTION

The invention relates to the field of agricultural biotechnology. More specifically, the invention provides novel genes involved in cellulose biosynthesis and methods using such genes to modulate cellulose biosynthesis in fiber-producing plants such as cotton. The invention also provides methods for identifying and isolating alleles of these genes in a population of fiber producing plants that correlate with the quality of the produced fibers.

BACKGROUND

Cellulose is the major structural polysaccharide of higher plant cell walls. Chains of β-1,4-linked glucosyl residues assemble soon after synthesis to form rigid, chemically resistant microfibrils. Their mechanical properties together with their orientation in the wall influence the relative expansion of cells in different directions and determine many of the final mechanical properties of mature cells and organs. These mechanical properties are of great importance for wood, paper, textile and chemical industries.

Much of the high quality fiber for the textile industry is provided for by cotton. About 90% of cotton grown worldwide is *Gossypium hirsutum* L., whereas *Gossypium barbadense* accounts for about 8%.

Several genes involved in cellulose biosynthesis have already been identified by mutational analysis in a number of plants. Mutants of *Arabidopsis thaliana* show that in vivo cellulose synthesis requires the activity of members of the AtCesA gene family encoding glycosyltransferases (Arioli et al., 1998; Taylor et al., 1999; Fagard et al., 2000; Taylor et al., 2000; Scheible et al., 2001; Burn et al., 2002a; Desprez et al., 2002), of the AtKOR1 gene (At5g49720) encoding a membrane-associated endo-1,4-β-D-glucanase (Nicol et al., 1998; Zuo et al., 2000; Lane et al., 2001; Sato et al., 2001), of KOBITO1 encoding a plasma membrane protein of unknown function (Pagant et al., 2002) and of genes encoding enzymes in the N-glycosylation/quality control pathway in the ER (Lukowitz et al., 2001; Burn et al., 2002b; Gillmor et al., 2002).

The function of an endo-1,4-β-D-glucanase in cellulose synthesis remains to be determined but the lack of activity against crystalline cellulose of BnCel16, a related *Brassica napus* enzyme (Mølhøj et al., 2001), suggests that the enzyme probably cleaves a non-crystalline glucan chain such as a lipid-linked primer or glucan donor (Williamson et al., 2001; Peng et al., 2002). Tomato Cel3 (LeCel3) was the first such membrane-associated endo-1,4-β-D-glucanase identified (Brummell et al., 1997) and antibodies to LeCel3 detected a cotton fiber protein upregulated during herbicide inhibition of cellulose synthesis (Peng et al., 2001). A cotton fiber membrane fraction required $Ca^{2+}$ for in vitro cellulose synthesis activity and, because an exogenous, $Ca^{2+}$-independent endo-1,4-β-D-glucanase restored cellulose synthesis activity, a cotton orthologue of KOR (GhKOR) was proposed as the endogenous $Ca^{2+}$-dependent factor (Peng et al., 2002). A truncated form of BnCel16 showed $Ca^{2+}$-dependence in vitro (Mølhøj et al., 2001).

Further genetic data point to cellulose synthesis responding to defects in enzymes on the N-glycosylation/quality control pathway. These steps occur in the ER rather than at the plasma membrane and so probably act only indirectly on synthesis through the supply of key glycoproteins to the plasma membrane. N-glycosylation begins when the mannose-rich oligosaccharide Glc3Man9GlcNac2 is assembled on dolichol in the ER membrane and transferred to the Asn residue of a newly synthesized protein containing an Asn-X-Ser or Asn-X-Thr motif (where X is any amino acid except Pro).

With further processing of the glycoprotein by glucosidases I and II, N-glycosylation intersects with the quality control pathway responsible for ensuring proper folding of newly synthesized proteins (Helenius and Aebi, 2001; Vitale, 2001). Glucosidase I removes the terminal α-1,2-linked glucosyl residue to generate Glc2Man9GlcNac2 and glucosidase II removes the next α-1,3-glucosyl residue. Polypeptides carrying the resultant GlcMan9GlcNac2 specifically bind chaperones (calnexin and calreticulin) and probably other proteins that promote proper folding of newly synthesized proteins. The glycoprotein releases the chaperones when glucosidase II trims of the final Glc residue which is required for chaperone binding. Glycoprotein glucosyltransferase then reattaches one Glc residue to the Man9GlcNAc2 of improperly folded glycoproteins so that they again bind chaperones and have a further opportunity to fold properly. Properly folded proteins, however, cannot be reglucosylated by that enzyme and progress though the secretory pathway for further processing and delivery.

Defects at several points in this pathway affect cellulose synthesis. Sequence analysis suggests that the potato MAL1 gene encodes a glucosidase II and antisense suppression reduces glucosidase II activity (Taylor et al, 2000a). M4LJ antisense plants accumulate less cellulose than controls when grown under field conditions although there is no visible phenotype in glasshouse conditions. The embryo lethal knopf mutant is deficient in glucosidase I and severely deficient in cellulose (Gillmor et al., 2002). Finally the embryo lethal cyt1 mutant is cellulose-deficient from a defect in mannose-1-phosphate guanylyltransferase, the enzyme generating the UDP-Man required to (amongst other things) assemble the high mannose oligosaccharide that is transferred from dolichol to the nascent protein (Lukowitz et al, 2001). The mutations that affect cellulose synthesis concentrate towards those early steps where the N-glycosylation pathway intersects with the quality control pathway. Quality control, rather than production of mature glycans on critical proteins, seems particularly important since there is no detectable phenotype from a defect in N-acetyl glucosaminyl transferase I that blocks the steps in the Golgi that build mature, N-linked glycans (von Schaewen et al, 1993).

Baskin et al. 1992 described *Arabidopsis* mutants which show root radial swelling, named rsw1, rsw2 and rsw3. These mutant lines where shown to exhibit a selective reduction in cellulose production (Peng et al. 2000).

WO98/00549 relates generally to isolated genes which encode polypeptides involved in cellulose biosynthesis in plants and transgenic plants expressing same in sense or antisense orientation, or as ribozymes, co-suppression or gene-targeting molecules. More particularly, this disclosure is directed to a nucleic acid molecule isolated from *Arabidopsis thaliana, Oryza sativa*, wheat, barley, maize, *Brassica* spp. *Gossypium hirsutum* and *Eucalyptus* spp, which encode an enzyme which is important in cellulose biosynthesis, in particular the cellulose synthase enzyme and homologues, analogues and derivatives thereof and uses of same in the production of transgenic plants expressing altered cellulose biosynthetic properties.

WO 98/50568 discloses the use of a nucleotide sequence coding for an endo-1,4-β-glucanase to inhibit cell growth in a plant. The nucleotide sequence corresponds wholly or partially to the *Arabidopsis* KOR protein sequence, or to a protein sequence the N-terminal end of which has at least 40% identity with the first 107 amino acids of said KOR, or at least 70% identity with the first 107 amino acids of said KOR.

WO 97/24448 describes recombinant and isolated nucleic acids encoding a plant α-glucosidase enzyme. An antisense nucleotide was also provided as well as the use of both the isolated or recombinant sequences and the antisense sequences. Uses of the invention include enhancing and reducing expression of alpha-glucosidases and the provision of novel starches.

WO 00/08175 relates to nucleic acid molecules coding for a protein with the activity of an alpha-glucosidase from a potato. The invention also relates to methods for the production of transgenic plant cells and plants synthesizing modified starch. The invention further relates to vectors and host cells containing the nucleic acid molecules, plant cells and plants obtained according to the methods, starch synthesized by the described plant cells and methods for the production of such starch.

WO 98/39455 discloses a gene and enzyme participating in the synthesis of cellulose by microorganisms. A specific gene encoding a cellulase, cellulose synthase complex and alpha-glucosidase are described.

WO9818949 and U.S. Pat. No. 6,271,443 provide two plant cDNA clones that are homologs of the bacterial CelA genes that encode the catalytic subunit of cellulose synthase, derived from cotton (*Gossypium hirsutum*). Also provided are genomic promoter regions to these encoding regions to cellulose synthase. Methods for using cellulose synthase in cotton fiber and wood quality modification are also provided.

The prior art remains however deficient in providing alternatives to the known genes involved in cellulose biosynthesis and does not disclose the nucleotide sequence of the wild type gene involved in cellulose biosynthesis and mutated in the rsw3 mutant Arabidopsis line. Also, the prior art does not disclose the cotton homologues genes of RSW2 or RSW3 involved in cellulose biosynthesis from cotton.

These and other problems have been solved as set forth hereinafter in the different embodiments and claims of the invention.

SUMMARY OF THE INVENTION

It is one object of the invention to provide a method for increasing cellulose biosynthesis e.g. in lint fiber, in fiber-producing plants, such as cotton plants, comprising the steps of (a) providing cells of said fiber-producing plant with a chimeric gene comprising the following operably linked DNA fragments
  i) a promoter expressible in said cell of said plant, such as a constitutive promoter, a fiber specific promoter or an expansion promoter;
  ii) a DNA region coding for the protein comprising the amino acid sequence of SEQ ID No. 5 or SEQ ID No 6 or SEQ ID No 7 or SEQ ID No 8 (or a variant of that protein having the same enzymatic activity), such as the nucleotide sequence of SEQ ID No 1 from the nucleotide at position to the nucleotide at position 1986 or SEQ ID No. 2 from the nucleotide position 47 to the nucleotide at position 1906 or SEQ ID No 3 or SEQ ID No 4 from the nucleotide position 2 to the nucleotide at position 1576 or SEQ ID No. 9;
  iii) a 3' region involved in transcription termination and polyadenylation.

It is another object of the invention to provide a method for decreasing cellulose biosynthesis in fiber-producing plants, for example in cotton plants, e.g. in fuzz fiber, comprising the step of providing cells of said fiber-producing plant with a chimeric gene capable of reducing the expression of a gene endogenous to said fiber-producing plant, wherein said endogenous gene codes for a protein comprising the amino acid sequence of SEQ ID No. 5 or SEQ ID No 6 or SEQ ID No 7 or SEQ ID No 8 or a variant thereof, said variant having the same enzymatic activity. The introduced chimeric gene may comprise a nucleotide sequence of 21 contiguous nucleotides selected from a nucleotide sequence which codes for a protein comprising the amino acid sequence of SEQ ID No. 5 or SEQ ID No 6 or SEQ ID No 7 or SEQ ID No 8, such as the nucleotide sequence of SEQ ID No 1 or SEQ ID No. 2 or SEQ ID No 3 or SEQ ID No 4 or SEQ ID No. 9, or the complement thereof, operably linked to a plant expressible promoter, such as a constitutive promoter or a fuzz fiber specific promoter and a 3' region involved in transcription termination and polyadenylation. The chimeric gene may also comprise a first nucleotide sequence of 21 contiguous nucleotides selected from a nucleotide sequence which codes for a protein comprising the amino acid sequence of SEQ ID No. 5 or SEQ ID No 6 or SEQ ID No 7 or SEQ ID No 8, such as the nucleotide sequence of SEQ ID No. 1, SEQ ID No. 2, SEQ ID No. 3 and SEQ ID No. 4 or SEQ ID No. 9, and a second nucleotide sequence complementary to the first nucleotide sequence, operably linked to a plant expressible promoter and a 3' region involved in transcription termination and polyadenylation such that upon transcription of said chimeric gene, a RNA is formed which can form a double stranded RNA region between said first and said second nucleotide sequence.

The invention further relates to a chimeric gene for increasing cellulose biosynthesis in fiber-producing plants, e.g. in cotton plants, comprising the following operably linked DNA fragments: a promoter expressible in said cell of said plant such as a constitutive promoter, a (lint)-fiber specific promoter or an expansion promoter; a DNA region coding for the protein comprising the amino acid sequence of SEQ ID No 6 or SEQ ID No 7 or SEQ ID No 8 or a variant thereof, said variant having the same enzymatic activity, such as the nucleotide sequence of SEQ ID No. 1 from the nucleotide at position 121 to the nucleotide at position 1986 or SEQ ID No 2 from the nucleotide at position 47 to the nucleotide at position 1906 or SEQ ID No 3 or SEQ ID No 4 from the nucleotide at position 2 to the nucleotide at position 1576 or SEQ ID No. 9; and a 3' end region involved in transcription termination and polyadenylation.

The invention also relates to a chimeric gene for decreasing cellulose biosynthesis in fiber-producing plants, e.g. in cotton plants, comprising a nucleotide sequence of 21 contiguous nucleotides selected from a nucleotide sequence which codes for a protein comprising the amino acid sequence of SEQ ID No 6 or SEQ ID No 7 or SEQ ID No 8, such as the nucleotide sequence of SEQ ID No. 2, SEQ ID No. 3 or SEQ ID No. 4 or SEQ ID No. 9, or the complement thereof, operably linked to a plant expressible promoter and a 3' region involved in transcription termination and polyadenylation.

The invention further relates to a chimeric gene for decreasing cellulose biosynthesis in fiber-producing plants, e.g. in cotton plants, comprising a first nucleotide sequence of 21 contiguous nucleotides selected from a nucleotide sequence which codes for a protein comprising the amino acid sequence of SEQ ID No 6 or SEQ ID No 7 or SEQ ID No 8, and a second nucleotide sequence complementary to said first nucleotide sequence, operably linked to a plant expressible promoter and a 3' region involved in transcription termination and polyadenylation such that upon transcription of said chimeric gene, a RNA is formed which can form a double stranded RNA region between said first and said second nucleotide sequence.

It is yet another object of the invention to provide plant cells and plants comprising the chimeric genes of the invention as well as seeds of such plants comprising the chimeric genes of the invention.

The invention thus relates to the use of a chimeric gene according to the invention to modulate cellulose biosynthesis and fiber quality in a fiber producing plant, such as cotton.

It is also an object of the invention to provide a method for identifying allelic variations of the genes encoding proteins involved in cellulose biosynthesis in a population of different genotypes or varieties of a particular plant species, for example a fiber-producing plant species, which are correlated either alone or in combination with the quantity and/or quality of cellulose production, and fiber production comprising the steps of:

a) providing a population of different varieties or genotypes of a particular plant species or interbreeding plant species comprising different allelic forms of the nucleotide sequences encoding proteins comprising the amino acid sequences of SEQ ID No 5, 6, 7 or 8;
b) determining parameters related to fiber production and/or cellulose biosynthesis for each individual of the population;
c) determining the presence (or absence) of a particular allelic form of the nucleotide sequences encoding proteins comprising the amino acid sequences of SEQ ID No 5, 6, 7 or 8 for each individual of the population; and
d) correlating the occurrence of particular fiber or cellulose parameters with the presence of a particular allelic form of the mentioned nucleotide sequence or a particular combination of such allelic forms.

BRIEF DESCRIPTION OF THE FIGURES

FIG. 4. Alignment of the Aglu-3/RSW3 sequence (Genbank NP_201189; SEQ ID NO:26) with the sequences of ER-resident glucosidase II enzymes from potato (Accession number T07391; SEQ ID NO:27), mouse (NP_032086; SEQ ID NO:28) and fission yeast (CAB65603; SEQ ID NO:29). The clade 2 of Monroe et al. (1999) are shown to demonstrate the high conservation. They include several residues implicated in catalysis (Asp 512 and Asp 617; *). The site of the rsw3-1 mutation(Ser599●) is close to these consensus sequences and is conserved in these and other glucosidase II sequences. Predicted N-terminal signal sequences are boxed. No HDEL ER-retention sequences occur at the C-terminus.

FIG. 5. Alignments of the proposed β-subunits of Arabidopsis (At5g56360; SEQ ID NO:30) and rice (our amendment of BAA88186; SEQ ID NO:31) with the β-subunits of glucosidase II from mouse (AAC53183; SEQ ID NO:32) and fission yeast (BAA13906; SEQ ID NO:33). Note the predicted N-terminal signal sequences (boxed), C-terminal H/VDEL ER-retention signals and the mannose-receptor homology region (MHR) near the N-terminus. The 6 cysteines within the MHR (four only in yeast) are numbered and the R and Y residues implicated in substrate-binding (●) and the substrate recognition loop between cysteines 5 and 6 are marked. Elsewhere in the sequence, note the relatively high level of similarity in the N- and C-terminal domains and the much lower similarity and plant-specific inserts in the central region.

(f) Detail of the ringed area in (e) showing the very complex arrangement of the minute leaves, many of which carry trichomes of approximately normal size and morphology. Scale bar=200 μm.
(g) Scanning electron micrograph of the surface of a wild type leaf on a plant grown for 10 d at 30° C. Note the clearly defined cell boundaries, stomata and trichomes.
(h) The surface of an rsw3 leaf showing much less clear outlines to the pavement cells, an apparently collapsed trichome (CT) on top of its ring of subsidiary cells and many stomata with their guard cells protruding above the leaf surface. Scale bar for (g) and (h)=100 μm.

Figure 8:
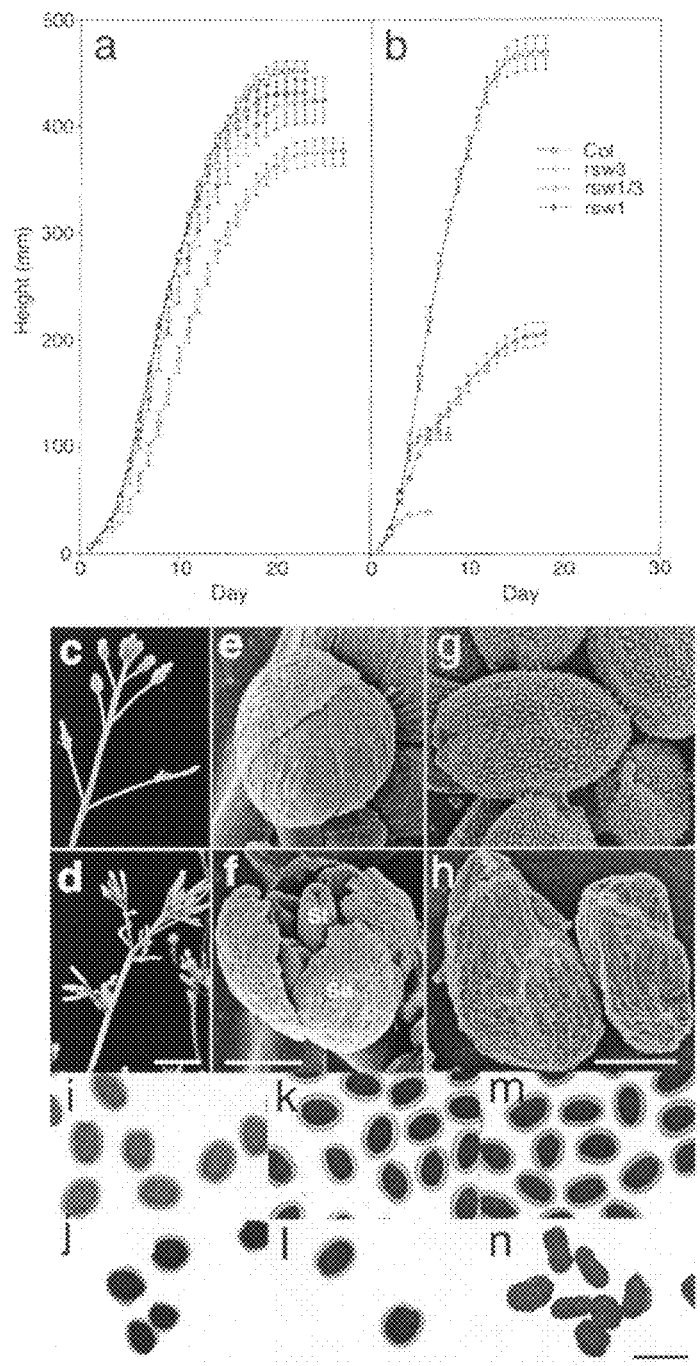

FIG. 8. Growth of the stem and reproductive development in rsw3.
(a and b) Kinetics of secondary stem elongation in Columbia wild type, rsw3, rsw1 and the rsw1rsw3 double mutant at 21° C. (a) and 30° C. (b). All plants were grown at 21° C. until stems began to emerge. These were cut off and re-growth of secondary bolts followed at the indicated temperature. Single mutants show very little difference from wild type at 21° C. although the double mutant elongates more slowly and reaches a significantly shorter final height. The final heights reached at 30° C. differ widely as do the trajectories by which they are reached. rsw1 elongates more slowly but elongation continues for at least as long as it does in wild type. rsw3 elongates almost as rapidly as wild type for 4 d but then ceases elongation by about day 6. The rsw1rsw3 double mutant elongates less rapidly and ceases elongation at about day 5.
(c and d). Light micrographs showing well spaced flowers in wild type (c) and the clustered flowers on rsw3 (d) with its early cessation of elongation.
(e and f) Cryoscanning electron micrographs showing flower buds of wild type (e) and rsw3 (f) that are of similar sizes but open prematurely in rsw3. Note the immature state of the stigma (St) and the irregular shapes of the cells on the sepals (Se) in rsw3. Bar for (e) and (f)=200 μm.
(g and h) Cryo-scanning electron micrographs showing imbibed seed of rsw3 that developed on plants held at 21° C. (g) and 30° C. (h). The 30° C. seed is shrunken and lacks the clear cellular pattern of the 21° C. seed.
(i-n) Light micrographs of imbibed seed stained with ruthenium red to show a surface coat of mucilage. Wild type (i,j), rsw1 (k,l), rsw3 (m,n). Seed in i, k, m developed on plants at 21° C., seed in j, l, n developed on plants at 30° C. Mucilage is secreted normally by rsw1 (l) and wild type (j) at 30° C. but not by rsw3(n).

DETAILED DESCRIPTION

The invention is based on the identification of the wild type gene which has been mutated in *Arabidopsis* mutant rsw3, and elucidation of its function. The inventors have also identified the cotton genes corresponding to the genes mutated in rsw2 and rsw3 *Arabidopsis* mutants. These cotton genes are implicated in cellulose production.

In one embodiment the invention thus relates to a method for increasing the production of cellulose in a plant comprising the steps of providing cells of the plant with a chimeric gene comprising a plant-expressible promoter operably linked to a DNA region coding for a protein comprising the amino acid sequence of SEQ ID No 5, SEQ ID No. 6, SEQ ID No 7 or SEQ ID No 8 or a variant thereof having similar activity as the mentioned proteins, and a 3' region involved in transcription termination and polyadenylation. The plants may be fiber-producing plants such as cotton, and the increased cellulose production may result in a larger production of cotton fibers, e.g. cotton lint fibers, or in cotton fibers with altered or increased length, or altered quality such as improved tensile strength.

As used herein, "chimeric gene" or "chimeric nucleic acid" refers to any gene or any nucleic acid, which is not normally found in a particular eukaryotic species or, alternatively, any gene in which the promoter is not associated in nature with part or all of the transcribed DNA region or with at least one other regulatory region of the gene.

As used herein, the term "promoter" denotes any DNA which is recognized and bound (directly or indirectly) by a DNA-dependent RNA-polymerase during initiation of transcription. A promoter includes the transcription initiation site, and binding sites for transcription initiation factors and RNA polymerase, and can comprise various other sites (e.g., enhancers), at which gene expression regulatory proteins may bind. The term "regulatory region", as used herein, means any DNA, that is involved in driving transcription and controlling (i.e., regulating) the timing and level of transcription of a given DNA sequence, such as a DNA coding for a protein or polypeptide. For example, a 5' regulatory region (or "promoter region") is a DNA sequence located upstream (i.e., 5') of a coding sequence and which comprises the promoter and the 5'-untranslated leader sequence. A 3' regulatory region is a DNA sequence located downstream (i.e., 3') of the coding sequence and which comprises suitable transcription termination (and/or regulation) signals, including one or more polyadenylation signals.

In one embodiment of the invention the promoter is a constitutive promoter. In another embodiment of the invention, the promoter activity is enhanced by external or internal stimuli (inducible promoter), such as but not limited to hormones, chemical compounds, mechanical impulses, abiotic or biotic stress conditions. The activity of the promoter may also be regulated in a temporal or spatial manner (tissue-specific promoters; developmentally regulated promoters).

In a particular embodiment of the invention, the promoter is a plant-expressible promoter. As used herein, the term "plant-expressible promoter" means a DNA sequence which is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S (Hapster et al., 1988), the subterranean clover virus promoter No 4 or No 7 (WO9606932), or T-DNA gene promoters but also tissue-specific or organ-specific promoters including but not limited to seed-specific promoters (e.g., WO89/03887), organ-primordia specific promoters (An et al., 1996), stem-specific promoters (Keller et al., 1988), leaf specific promoters (Hudspeth et al., 1989), mesophyl-specific promoters (such as the light-inducible Rubisco promoters), root-specific promoters (Keller et al., 1989), tuber-specific promoters (Keil et al., 1989), vascular tissue specific promoters (Peleman et al., 1989), stamen-selective promoters (WO 89/10396, WO 92/13956), and the like.

Suitable plant-expressible promoters include the fiber specific and/or secondary cell wall specific promoters which can be isolated according to the teaching of WO 98/18949, WO98/00549 or U.S. Pat. No. 5,932,713. Also suitable are the promoters disclosed in WO98/18949 or U.S. Pat. No. 6,271,443. Cotton lint-fiber specific promoters are also suitable.

In one embodiment of the above mentioned methods, the DNA region coding for a protein comprising the amino acid sequence of SEQ ID No 5, SEQ ID No 6, SEQ ID No 7 or SEQ ID No 8 comprises the nucleotide sequence of SEQ ID No 1 from nucleotide 121 to nucleotide 1986, SEQ ID No 2 from nucleotide 47 to nucleotide 1906, SEQ ID No. 3 or SEQ ID No. 4 from nucleotide 2 to nucleotide 1576 or SEQ ID No. 9.

In another embodiment of the above mentioned methods, the DNA region codes for a variant of the proteins comprising the amino acid sequence of SEQ ID No. 5, SEQ ID No. 6, SEQ ID No. 7 or SEQ ID No. 8. As used herein, "variant" proteins refer to proteins wherein one or more amino acids are different from the corresponding position in the proteins having the amino acid sequence of SEQ ID No. 5, SEQ ID No. 6, SEQ ID No. 7 or SEQ ID No. 8, by substitution, deletion, insertion; and which have at least one of the functions of the proteins encoded by SEQ ID No. 5, SEQ ID No. 6, SEQ ID No. 7 or SEQ ID No. 8 such as e.g. the same enzymatic or catalytic activity. Methods to derive variants such as site-specific mutagenesis methods are well known in the art, as well as assays to identify the enzymatic activity encoded by the variant sequences. Suitable substitutions include, but are not limited to, so-called conservative substitutions in which one amino acid residue in a polypeptide is replaced with another naturally occurring amino acid of similar chemical character, for example Gly⇔Ala, Val⇔Ile⇔Leu, Asp⇔Glu, Lys⇔Arg, Asn⇔Gln or Phe⇔Trp⇔Tyr.

Allelic forms of the nucleotide sequences which may encode variant proteins, according to the specification may be identified by hybridization of libraries, under stringent conditions, such as cDNA or genomic libraries of a different varieties or plant lines, e.g. cotton varieties and plant lines. Nucleotide sequences which hybridize under stringent conditions to nucleotide sequences encoding the amino acid sequence of SEQ ID 5, 6, 7 or 8 or to the nucleotide sequence of SEQ ID 1, 2, 3, 4 or 9, or a sufficiently large part thereof (e.g., at least about 25 contiguous nucleotides, at least about 50 contiguous nucleotides, or at least about 100 contiguous nucleotides) and which encode a functional protein that can complement at least one function, and may complement all of the affected functions, in the rsw2 or rsw3 mutant line in *Arabidopsis* are functional equivalents of the above mentioned coding regions. Such nucleotides may also be identified and isolated using e.g. polymerase chain reaction amplification using an appropriate pair of oligonucleotides having at least about 25 contiguous nucleotides, at least about 50 contiguous nucleotides, or at least about 100 contiguous nucleotides of the nucleotide of SEQ ID No 1, SEQ ID No 2, SEQ ID No. 3, SEQ ID No 4 or SEQ ID No. 9.

"Stringent hybridization conditions" as used herein mean that hybridization will generally occur if there is at least 95%, or at least 97%, sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5× Denhardt's solution, 10% dextran sulfate, and 20 µg/ml denatured, sheared carrier DNA such as salmon sperm DNA, followed by washing the hybridization support in 0.1×SSC at approximately 65° C. Other hybridization and wash conditions are well known and are exemplified in Sambrook et al, Molecular Cloning: A Laboratory Manual, Second Edition, Cold Spring Harbor, N.Y. (1989), particularly chapter 11.

As another aspect of the invention, the identified genes may be used to decrease cellulose biosynthesis in plants such as fiber-producing plants, e.g. cotton. Thus, in another embodiment of the invention, a method is provided to decrease cellulose biosynthesis in plants such as fiber-producing plants, e.g. in cotton plants, comprising the step of providing cells of said fiber-producing plant with a chimeric gene capable of reducing the expression of a gene endogenous to said fiber-producing plant, wherein said endogenous gene codes for a protein comprising the amino acid sequence of SEQ ID No. 5 or SEQ ID No 6 or SEQ ID No 7 or SEQ ID No 8 or a variant thereof, said variant having the same functional or enzymatic activity.

In one embodiment of this method of the invention, a chimeric gene is provided to cells of the plant, wherein the chimeric gene comprises a nucleotide sequence of 21 contiguous nucleotides selected from a nucleotide sequence which codes for a protein comprising the amino acid sequence of SEQ ID No. 5 or SEQ ID No 6 or SEQ ID No 7 or SEQ ID No 8, such as a nucleotide sequence of 21 contiguous nucleotides selected from the nucleotide sequences of SEQ ID No. 1 or SEQ ID No 2 or SEQ ID No 3 or SEQ ID No 4 or SEQ ID No. 9 operably linked to a plant expressible promoter and a 3' region involved in transcription termination and polyadenylation (so-called "sense" RNA mediated gene silencing). In another embodiment of this method of the invention, a chimeric gene is provided to cells of the plant, wherein the chimeric gene comprises a nucleotide sequence of 21 contiguous nucleotides selected from the complement of a nucleotide sequence which codes for a protein comprising the amino acid sequence of SEQ ID No. 5 or SEQ ID No 6 or SEQ ID No 7 or SEQ ID No 8, such as a nucleotide sequence of 21 contiguous nucleotides selected from the complement of the nucleotide sequences of SEQ ID No. 1 or SEQ ID No 2 or SEQ ID No 3 or SEQ ID No 4 or SEQ ID No. 9 operably linked to a plant expressible promoter and a 3' region involved in transcription termination and polyadenylation (so-called "antisense" RNA mediated gene silencing).

The length of the antisense or sense nucleotide sequence may vary from about 21 nucleotides (nt), up to a length equaling the length (in nucleotides) of the target nucleic acid. The total length of the antisense or sense nucleotide sequence may be at least about 50 nt, 100 nt, 150 nt, 200 nt, or 500 nt long. It is expected that there is no upper limit to the total length of the antisense nucleotide or sense nucleotide sequence, other than the total length of the target nucleic acid. However for practical reason (such as, e.g., stability of the chimeric genes) the length of the antisense or sense nucleotide sequence may be limited to 5000 nt, to 2500 nt, or even to about 1000 nt.

It will be appreciated that the longer the total length of the antisense or sense nucleotide sequence is, the less stringent the requirements for sequence identity between the total antisense or sense nucleotide sequence and the corresponding sequence in the target gene or the complement thereof become. In one embodiment, the total antisense nucleotide sequence will have a sequence identity of at least about 75% with the complement corresponding target sequence; alternatively, at least about 80%, at least about 85%, about 90%, about 95%, about 100%, or is identical to complement of the corresponding part of the target nucleic acid. In one embodiment, the antisense or sense nucleotide sequence will include a sequence of about 20-21 nt with 100% sequence identity to the corresponding part of the target nucleic acid or the complement thereof. For calculating the sequence identity and designing the corresponding antisense or sense sequence, the number of gaps may be minimized, particularly for the shorter antisense or sense sequences.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The alignment of the two sequences may be performed by the Needleman and Wunsch algorithm (Needleman and Wunsch, 1970) Computer-assisted sequence alignment, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

Another embodiment of the invention, relates to a method for reducing the expression of endogenous genes of said fiber-producing plant, wherein said endogenous gene codes for a protein comprising the amino acid sequence of SEQ ID No. 5 or SEQ ID No 6 or SEQ ID No 7 or SEQ ID No 8 or a variant thereof using DNA regions, under the control of a plant-expressible promoter, which when transcribed result in so-called double stranded RNA molecules, comprising both sense and antisense sequences which are capable of forming a double stranded RNA molecule as described in WO 99/53050 (herein entirely incorporated by reference).

Thus, in one embodiment of the invention, a chimeric gene may be provided to a plant cell comprising a plant expressible promoter operably linked to a DNA region, whereby that DNA region comprises a part of coding region comprising at least 20 or 21 consecutive nucleotides from the coding region of a nucleic acid encoding a protein with the amino acid sequence of SEQ ID Nos 5, 6, 7 or 8 (the so-called sense part) as well as a DNA sequence that comprises at least the complementary DNA sequence of at least 20 or 21 nucleotides of the sense part, but which may be completely complementary to the sense part (the so-called antisense part). The chimeric gene may comprise additional regions, such as a transcription termination and polyadenylation region functional in plants. When transcribed an RNA can be produced which may form a double stranded RNA stem between the complementary parts of the sense and antisense region. A spacer region may be present between the sense and antisense nucleotide sequence. The chimeric gene may further comprise an intron sequence, which may be located in the spacer region.

In yet another embodiment of the invention, the chimeric gene used to reduce the expression of a gene endogenous to said fiber-producing plant, wherein said endogenous gene codes for a protein comprising the amino acid sequence of SEQ ID No. 5 or SEQ ID No 6 or SEQ ID No 7 or SEQ ID No 8 or a variant thereof, said variant having the same functional or enzymatic activity, encodes a ribozyme which recognizes and cleaves RNA having the nucleotide sequence of an RNA coding for a protein comprising the amino acid sequence of SEQ ID No. 5 or SEQ ID No 6 or SEQ ID No 7 or SEQ ID No 8 or a variant thereof. In another embodiment, the ribozyme recognizes and cleaves RNA having the nucleotide sequence of an RNA comprising the nucleotide sequence of SEQ ID 1, 2, 3 or 4. Methods for designing and using ribozymes have been described by Haseloff and Gerlach (1988) and are contained i.a. in WO 89/05852.

It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application. In yet another embodiment of the invention, nucleic acids (either DNA or RNA molecules) are provided which can be used to alter cellulose biosynthesis in plants. Thus the invention provides chimeric genes (DNA molecule) which comprise the following operably linked DNA fragments i) a promoter expressible in said cell of said plant;
ii) a DNA region comprising a nucleotide sequence of at least 21 nucleotides selected from a nucleotide sequence coding for the protein comprising the amino acid sequence of SEQ ID No 6 or SEQ ID No 7 or SEQ ID No 8 (or a variant of that protein having the same enzymatic activity), such as the nucleotide sequence of SEQ ID Nos 1, 2, 3, 4 or 9; and/or
iii) a DNA region and comprising a nucleotide sequence of at least 21 nucleotides selected from the complement of a nucleotide sequence coding for the protein comprising the amino acid sequence of SEQ ID No 6 or SEQ ID No 7 or SEQ ID No 8 or a variant thereof, said variant having the same enzymatic activity, such as the nucleotide sequence of SEQ ID Nos 1, 2, 3, 4 or 9; and
iv) a 3'end region involved in transcription termination and polyadenylation.

Also provided are RNA molecules that can be obtained from the chimeric genes according to the invention. Such RNA molecules can be produced by in vivo or in vitro transcription of the chimeric genes. They can also be obtained through in vitro transcription of chimeric genes, wherein the transcribed region is under control of a promoter recognized by single subunit RNA polymerases from bacteriophages such as SP6, T3 or T7. Alternatively, the RNA molecules may be synthesized in vitro using procedures well known in the art. Also chemical modifications in the RNA ribonucleoside backbone to make the chimeric RNA molecules more stable are well known in the art.

Different embodiments for chimeric genes or RNA molecules have been described above in relation to the provided methods for altering cellulose biosynthesis and can be applied *mutatis mutandis* to the embodiments relating to substances.

Chimeric genes or RNA may be provided to plant cells in a stable way, or transiently. Conveniently, stable provision of chimeric genes or RNA molecules may be achieved by integration of the chimeric genes into the genome of the cells of a plant. Methods for the introduction of chimeric genes into plants are well known in the art and include *Agrobacterium*-mediated transformation, particle gun delivery, microinjection, electroporation of intact cells, polyethylene glycol-mediated protoplast transformation, electroporation of protoplasts, liposome-mediated transformation, silicon-whiskers mediated transformation etc. The transformed cells obtained in this way may then be regenerated into mature fertile plants.

In another embodiment, the chimeric genes or chimeric RNA molecules of the invention may be provided on a DNA or RNA molecule capable of autonomously replicating in the cells of the plant, such as e.g. viral vectors. The chimeric gene or the RNA molecules of the invention may also be provided transiently to the cells of the plant.

It is also an object of the invention to provide plant cells and plants containing the chimeric genes or the RNA molecules according to the invention. Gametes, seeds, embryos, either zygotic or somatic, progeny or hybrids of plants comprising the chimeric genes of the present invention, which are produced by traditional breeding methods, are also included within the scope of the present invention.

The methods and means of the invention are suited for use in cotton plants, (both *Gossypium hirsutum* and *Gossypium barbadense*) including, but not limited to, plants such as Coker 312, Coker310, Coker 5 Acala SJ-5, GSC25110, Fiber-Max® 819, FiberMax® 832, FiberMax® 966, FiberMax® 958, FiberMax® 989, FiberMax® 5024 (and transgenic FiberMax® varieties exhibiting herbicide or insect-resistant traits) Siokra 1-3, T25, GSA75, Acala SJ2, Acala SJ4, Acala SJ5, Acala SJ-C1, Acala B1644, Acala B1654-26, Acala B1654-43, Acala B3991, Acala GC356, Acala GC510, Acala GAM1, Acala C1, Acala Royale, Acala Maxxa, Acala Prema, Acala B638, Acala B 1810, Acala B2724, Acala B4894, Acala B5002, non Acala "picker" Siokra, "stripper" variety FC2017, Coker 315, STONEVILLE 506, STONEVILLE 825, DP50, DP61, DP90, DP77, DESI 19, McN235, HBX87, HBX191, HBX107, FC 3027, CHEMBRED A1, CHEMBRED A2, CHEMBRED.A3, CHEMBRED A4, CHEMBRED B1, CHEMBRED B2, CHEMBRED B3, CHEMBRED C1, CHEMBRED C2, CHEMBRED C3, CHEMBRED C4, PAYMASTER 145, HS26, HS46, SICALA, PIMA S6 and ORO BLANCO PIMA.

The methods and means described herein may also be employed for other plant species such as hemp, jute, flax and woody plants, including but not limited to *Pinus* spp., *Populus* spp., *Picea* spp., *Eucalyptus* spp., etc.

In another embodiment, a method for identifying allelic variations of the genes encoding proteins involved in cellulose biosynthesis in a population of different genotypes or varieties of a particular plant species, for example a fiber-producing plant species, which are correlated either alone or in combination with the quantity and/or quality of cellulose production, and fiber production is provided. This method comprises the following steps:

a) providing a population of different varieties or genotypes of a particular plant species or interbreeding plant species comprising different allelic forms of the nucleotide sequences encoding proteins comprising the amino acid sequences of SEQ ID No 5, 6, 7 or 8. The different allelic forms may be identified using the methods described elsewhere in this application. For example, a segregating population may be provided, wherein different combinations of the allelic variations of the genes encoding proteins involved in cellulose biosynthesis are present. Methods to produce segregating populations are well known in the art of plant breeding.

b) Determining parameters related to fiber production and/or cellulose biosynthesis for each individual of the population;

c) determining the presence of a particular allelic form of the nucleotide sequences encoding proteins comprising the amino acid sequences of SEQ ID No 5, 6, 7 or 8 for each individual of the population; and d) correlating the occurrence of particular fiber or cellulose parameters with the presence of a particular allelic form of the mentioned nucleotide sequence or a particular combination of such allelic forms.

The resulting information will allow selecting those alleles which have the desired effect on cellulose biosynthesis or fiber production. The resulting information may be used to accelerate breeding programs, to isolate or create varieties with particular fiber or cellulose characteristics, or to accelerate backcross programs, by determining the presence or absence of allelic forms, using conventional molecular biology techniques. Methods for determining allelic forms in polyploid plants are known in the art and include e.g. Denaturing High-Performance Liquid Chromatography (DHPLC; Underhill et al. (1997) *Genome Research* 7:996-1005). It will be clear that not only the sequences of the alleles themselves can be used to determine their presence or absence during breeding or backcross programs, but also of the nucleotide sequences adjacent (e.g., immediately adjacent) and contiguous with the desired alleles, and which can only be separated from the allele by recombination during meiosis at low frequencies during meiosis.

As used herein "an interbreeding plant species" is a species which can be crossed with the fiber producing plant such as cotton (including using techniques such as hybridization etc.) and can produce progeny plants. Interbreeding plant species may include wild relatives of the fiber producing plants. Conventionally, for cotton plants reference is made to interbreeding for crosses between *G. barbadense* and *G. hirsutum* and to intrabreeding for crosses between two *G. barbadense* or two *G. hirsutum* parents.

The following non-limiting Examples describe method and means for modulating cellulose biosynthesis in fiber-producing plants. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, NY and in Volumes 1 and 2 of Ausubel et al. (1994) *Current Protocols in Molecular Biology*, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) *Molecular Cloning: A Laboratory Manual*, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) *PCR Primer: A Laboratory Manual*, Cold Spring Harbor Laboratory Press, and in McPherson at al. (2000) *PCR—Basics: From Background to Bench*, First Edition, Springer Verlag, Germany.

Throughout the description and Examples, reference is made to the following sequences:

SEQ ID No.1: *Arabidopsis* nucleotide sequence rsw2 (genomic; Accession number At5g4970).

SEQ ID No. 2: cotton nucleotide sequence rsw2 (cDNA)

SEQ ID No. 3: *Arabidopsis* nucleotide sequence rsw3 (genomic)

SEQ ID No. 4: cotton nucleotide sequence rsw3 (corresponding to the 3' end; cDNA)

SEQ ID No. 5: *Arabidopsis* amino acid sequence rsw2

SEQ ID No. 6: cotton amino acid sequence rsw2

SEQ ID No. 7: *Arabidopsis* amino acid sequence rsw3

SEQ ID No. 8: cotton amino acid sequence rsw3 (partial)

SEQ ID No. 9: *Arabidopsis* nucleotide sequence rsw2 (cDNA)

SEQ ID No. 10: oligonucleotide PCR primer (forward rsw2 cotton)

SEQ ID No. 11: oligonucleotide PCR primer (reverse rsw2 cotton)

SEQ ID No. 12: oligonucleotide PCR primer (forward LFY3)

SEQ ID No. 13: oligonucleotide PCR primer (reverse LFY3)

SEQ ID No. 14: oligonucleotide PCR primer (forward MBK5/α)

SEQ ID No. 15: oligonucleotide PCR primer (reverse MBK5/α)

SEQ ID No. 16: oligonucleotide PCR primer (At glucosidase II α forward)

SEQ ID No. 17: oligonucleotide PCR primer (At glucosidase II α reverse) 10

SEQ ID No. 18: oligonucleotide PCR primer (At glucosidase II β forward)

SEQ ID No. 19: oligonucleotide PCR primer (At glucosidase II β reverse)

SEQ ID No. 20: oligonucleotide PCR primer (forward primer to isolate genomic copy RSW3)
SEQ ID No. 21: oligonucleotide PCR primer (reverse primer to isolate genomic copy RSW3)
SEQ ID No. 22: oligonucleotide PCR primer (forward RWS3 homologue cotton)
SEQ ID No. 23: oligonucleotide PCR primer (reverse RSW3 homologue cotton).

EXAMPLE 1

Isolation of a Full Length cDNA of the GhKOR Gene (Cotton Gene Corresponding to the rsw2 Mutation in *Arabidopsis*)

Figure 1:
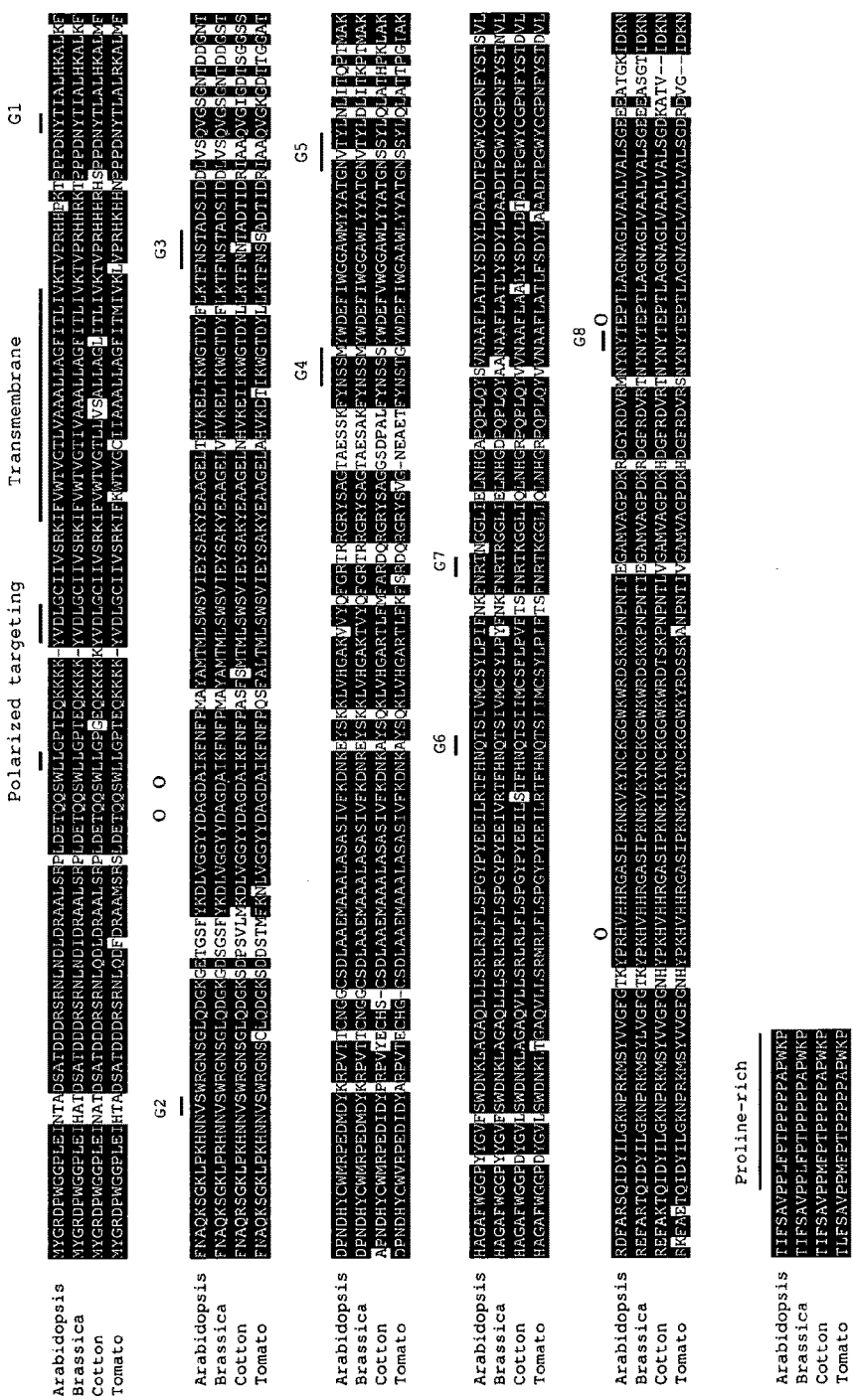
FIG. 1. ClustalW alignment of proteins GhKOR (SEQ ID NO:6), and LeCel3 (Accession number T07612; SEQ ID NO:24) and AtKOR1 (Accession number At5g49720; SEQ ID NO:5) and BnCel16 (Accession number CAB51903; SEQ ID NO:25). Features highlighted are: polarized targeting motifs implicated in targeting to the cell plate (Zuo et al., 2000); a putative transmembrane region near the N-terminus (transmembrane); four of the conserved residues potentially involved in catalysis (Asp-198, Asp-201, His-516 and E-555; labeled o) and representing part of the strong similarity to family 9 glycoside hydrolases; a C-terminal region rich in Pro and characteristic of membrane-bound members of the endo-1,4-β-glucanase family; 8 putative N-glycosylation sites (Asn-X-Ser/Thr; labelled G1 to G8).

The NCBI EST database has 7 ESTs from a *Gossypium arboreum* 7-10 dpa (days post anthesis) fiber library which show similarities to the sequence of AtKOR1. The sequences of five of the seven ESTs were identical. Alignment of the three different cotton ESTs against the AtKOR1 cDNA showed that cotton clone AW726657 contained the ATG start codon, and 47 bp of 5' untranslated region. Clone BE052640 spanned the middle region of the KOR gene and overlapped clone AW668085 which contained a TGA stop codon in the same position as that in AtKOR1 and 126 bp of 3' untranslated sequence. Translation of the ORF showed >80% amino acid sequence identity to regions of AtKOR1 protein. Primers designed to the 5' and 3' untranslated regions of the *G. arboreum* ESTs were used to amplify a 1.9 kb PCR product from an 18 dpa fiber cDNA library from the *G. hirsutum* cultivar Siokra 1-4. The forward primer was 5'-CCGCTC-GAGCGGGCATTTTCCGCCCACTA-3' (SEQ ID No. 10) and the reverse primer 5'-CGGGATCCCGTCACACATG-GACAGAAGAA-3' (SEQ ID No 11). A full length cDNA of the cotton KOR gene was generated by the PCR of a cotton cDNA library from 18 dpa fibers of *Gossypium hirsutum* and the products of several amplifications sequenced (SEQ ID No. 2). The cDNA encoded a protein (GhKOR) of 619 amino acids (SEQ ID No. 6) that was highly similar to LeCel3 (86% amino acid identity), AtKOR1 (82% amino acid identity) and BnCel16 (82% identity) (FIG. 1). All proteins shared: polarized targeting motifs involved in targeting AtKOR1 to the cell plate (Zuo et al., 2000); a putative transmembrane region near the N-terminus; four of the conserved residues potentially involved in catalysis (Asp-198, Asp-201, His-516 and E-555; Nicol et al., 1998) as part of the strong similarity to family 9 glycoside hydrolases; a C-terminal region rich in Pro and characteristic of membrane-bound members of the endo-1,4-β-D-glucanase family; 8 putative N-glycosylation sites (Asn-X-Ser/Thr) in the N-terminal domain predicted to be in the ER lumen during glycosylation. (An additional site present only in GhKOR (residues 14-16) would face the cytosol).

EXAMPLE 2

Complementation of the Arabidopsis rsw2-1 Mutant with GhKOR

The cotton PCR product encoding GhKOR was cloned behind the CaMV 35S promoter in the following way: the forward primer incorporated a XhoI site (underlined), and the reverse primer a BamHI site (underlined) which allowed the amplified 1.9 kb fragment to be ligated into the appropriate sites in vector pART7 (Gleave, 1992). This placed the cDNA in the sense orientation behind the cauliflower mosaic virus 35S promoter. The complete expression cassette was removed by digestion with NotI and cloned into the corresponding site in the binary vector pART27. The amplified product was sequenced to confirm its identity. This construct was introduced into *Agrobacteriurn tumefaciens* strain AGL1 and used to transform the rsw2-1 mutant and wild-type Columbia by floral dipping (Clough and Bent, 1998).

Kanamycin resistant transformants were selected on Hoagland's plates containing kanamycin (50 μg/ml) and timentin (100 μg/ml), transferred to vertical Hoagland's plates without selection agents and screened for root swelling after 2 days at 29° C. T2 seed was collected from ten individual T1 plants showing a wild-type phenotype and checked for inheritance of the complemented phenotype in the T2 generation. Photographs were taken of roots of T3 seedlings that were homozygous for kanamycin resistance and had been exposed to 29° C. for 2 d. Other plants grown in pots at 21° C. until the bolt was initiated had the bolt cut off before transfer to 29° C. and the regenerated secondary bolts were photographed when mature. rsw2-1 has a single nucleotide change from Columbia in At5g49720 that replaces Gly-429 with Arg in AtKOR1 and provides a temperature-sensitive phenotype (Baskin et al., 1992; Lane et al., 2001). Plants were grown either in pots (1:1:1 mix of peat:compost:sand), or aseptically in Petri dishes (MS or Hoagland's medium with agar) (Burn et al., 2002a). Growth cabinets provided 100 μmol $m^{-2}s^{-1}$ of continuous light at 21° C. unless otherwise stated. Roots of the rsw2 mutant show temperature-sensitive radial swelling (Baskin et al., 1992) and stems show temperature-sensitive inhibition of elongation (Lane et al., 2001).

Figure 2:
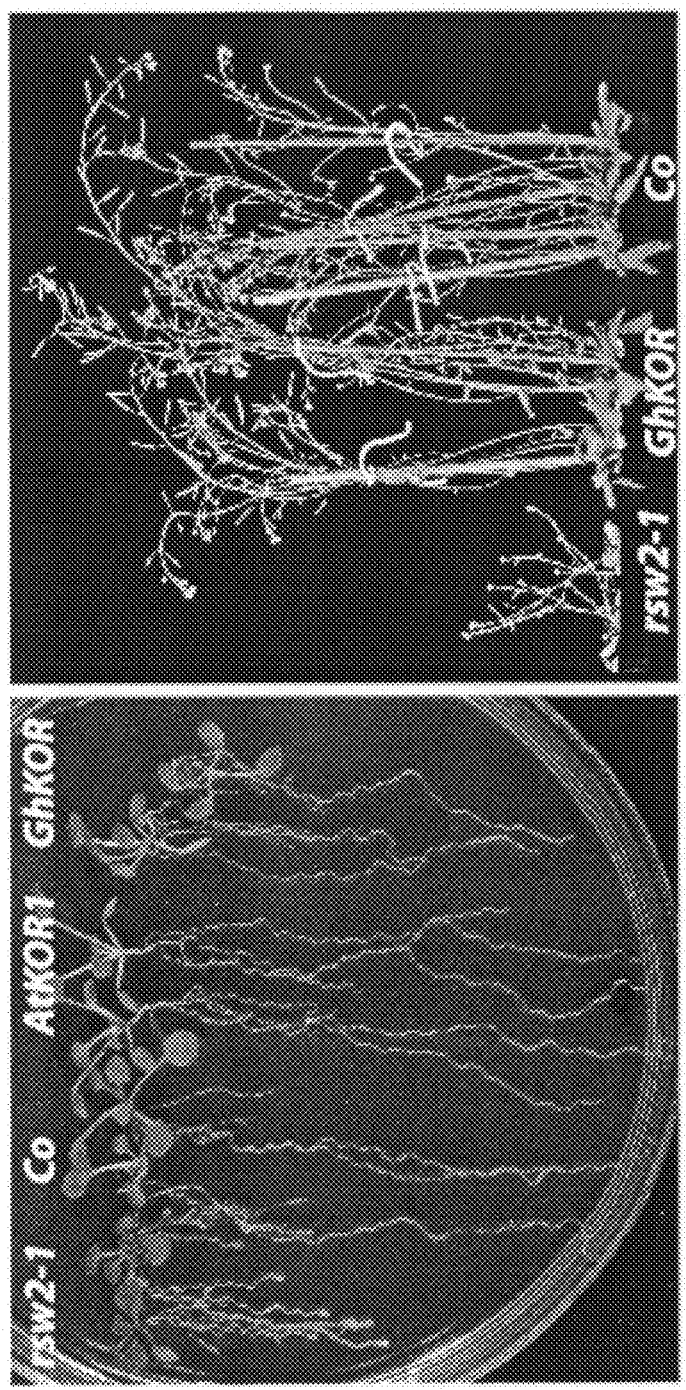
FIG. 2. Complementation of rsw2-1 by transformation with GhKOR1 cDNA (SEQ ID No 2), operably linked to the CaMV35 S promoter. (A) Roots of rsw2 -1 swell after exposure to 29° C. for 2 d but wild type (Co) and complemented plants containing either AtKOR1 or GhKOR do not. (B) Mature stems of two plants each of rsw2-1 (left), wild type and rsw2 -1 expressing GhKOR. Photograph of plants grown in pots at 21° C., until bolting began, at which time bolts were cut off and plants transferred to 29° C. for bolts to regrow.

The roots of 63 out of 75 of the kanamycin-resistant T1 seedlings did not swell after 2 d at 29° C. The wild type phenotype was stably inherited into the T3 generation and roots (FIG. 2A) and stems (FIG. 2B) elongated normally at the restrictive temperature. Stem growth in T3 plants homozygous for kanamycin resistance was quantitatively indistinguishable from wild type. A gene was thus identified encoding a cotton homologue of AtKOR1 and it was shown that it can functionally replace the Arabidopsis gene in the rsw2-1 cellulose synthesis mutant.

This will involve GhKOR correcting defects in cytokinesis and cell elongation in *Arabidopsis* (Nicol et al., 1998; Zuo et al., 2000; Lane et al., 2001; Sato et al., 2001) as well as proper interaction with other elements of the cellulose synthesis machinery and/or products. Previous studies identified a cotton fiber protein immunologically related to LeCel3 (Peng et al., 2001) and indirect evidence implicated it in cellulose synthesis in vitro by cotton fiber membranes (Peng et al., 2002). The similarities to LeCel3, BnCel16 and AtKOR1 includes all major features of known functional significance and those, such as the Pro-rich C-terminus, which have no currently known function. The role of an endo-1,4-β-D-glucanase in cellulose synthesis is not clearly established but could involve severing a yet-to-crystallize glucan from a lipid-linked primer or donor (Williamson et al., 2001; Peng et al., 2002).

EXAMPLE 3

Identification and Isolation of the Gene that has Been Mutated in rsw3 Mutant of *Arabidopsis thaliana*

The rsw3 allele behaves as a single Mendelian recessive locus (Baskin et al, 1992) and was identified by a map based strategy. The F2 progeny from crossing rsw3 with the visual marker line W9 linked RSW3 with yi on the lower arm of chromosome 5. An F2 population from crossing rsw3 (Columbia background) with the Landsberg erecta ecotype was screened to give plants showing a root swelling phenotype.

DNA was prepared from 2-3 rosette leaves per plant using the FastDNA kit (BIO 101, Carlsbad, Calif.) and mapping carried out using LFY3 (forward primer 5'-GACGGCGTCTAGAA-GATTC-3' (SEQ ID No. 12), reverse 5'-TAACT-TATCGGGCTTCTGC-3'; SEQ ID No. 13; cleavage with RsaI) and MBK5/α (forward 5'-CCCTCGCTTGGTA-CAAGGTAT-3' (SEQ ID No. 14) and reverse 5'-TCCT-GATCCTCTCACCACGTA-3'(SEQ ID No. 15). Using the F2 from a cross to the Landsberg erecta ecotype, RSW3 was mapped at 6 cM from the LFY3 locus (4 out of 70 chromosomes showing a cross over event) so positioning RSW3 between yi and LFY3. Analysis of a further 372 chromosomes identified one recombination event between MBK5/α and rsw3, a notional map distance of 0.27 cM. Several candidate genes in this region were sequenced in rsw3. One (At5g63840) on the P1 clone mgi19 (AB007646) encoded a putative catalytic subunit of glucosidase II and the rsw3 allele showed a T to C substitution predicted to replace Ser599 with Phe in the protein (nucleotide sequence of the wild type RSW3 gene is represented in SEQ ID No. 3, amino acid sequence of the encoded protein is represented in SEQ ID No. 7).

Figure 4:
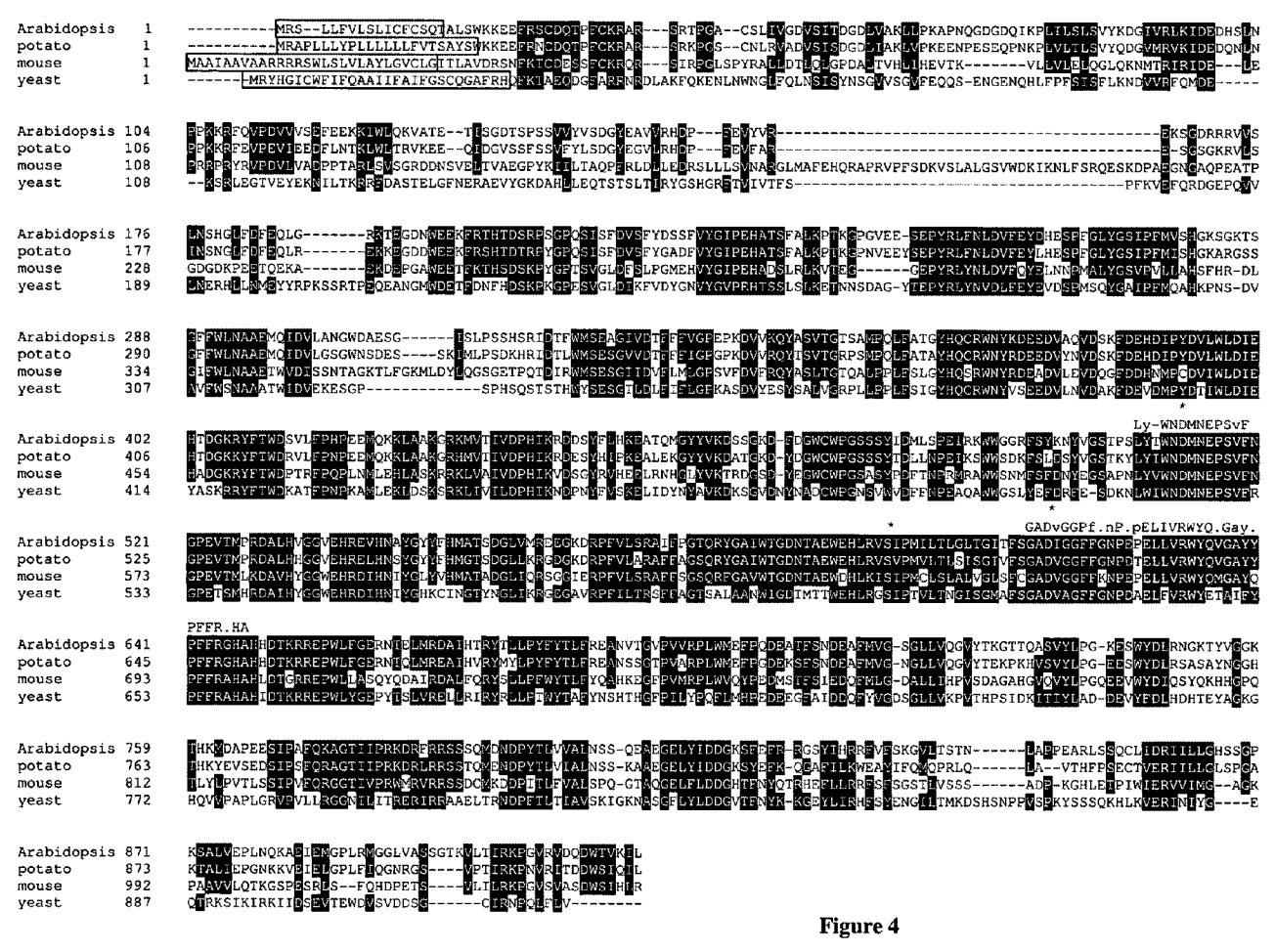

The RSW3 sequence is highly similar from about residue 150 onwards to sequences in the glucoside hydrolase family 31 (Henrissat, 1991; Henrissat and Bairoch, 1993). Monroe et al identified the RSW3 glucosidase II gene through a search of *Arabidopsis* ESTs with homology to α-glucosidases and named it Aglu-3 (Monroe et al., 1999). Its protein product formed a clade with several glucosidase II enzymes whose catalytic activities were independently known. They all separated from apoplastic α-glycosidases of *Arabidopsis* with which Aglu-3/RSW3 shares only 8% sequence identity. FIG. 4 shows the two signature motifs for the clade containing Aglu3/RSW3, which are believed to include catalytic and substrate binding residues. Aglu3/RSW3 contains all of the conserved residues within these motifs, as well as the proposed catalytic residues Asp512 and Asp617 (Frandsen and Svensson, 1998). Ser599, which is mutated in rsw3, is likely to be functionally significant since it is conserved in the homologous gene product from mouse (NP 032086), human (NP 055425), pig (AAB49757), slime mold (AAB18921), potato (P07391) and cotton (see below), and in the more distantly related apoplastic α-glucosidases encoded by the *Arabidopsis* genes Aglu-1 and Aglu-2 (Monroe et al., 1999). The *Arabidopsis* Aglu-3/RSW3 gene appears to be a single copy, spans 3.84 kb with 5 introns and encodes a predicted transcript of 2766 bp giving a predicted translation product of 104 kDa.

Figure 5:
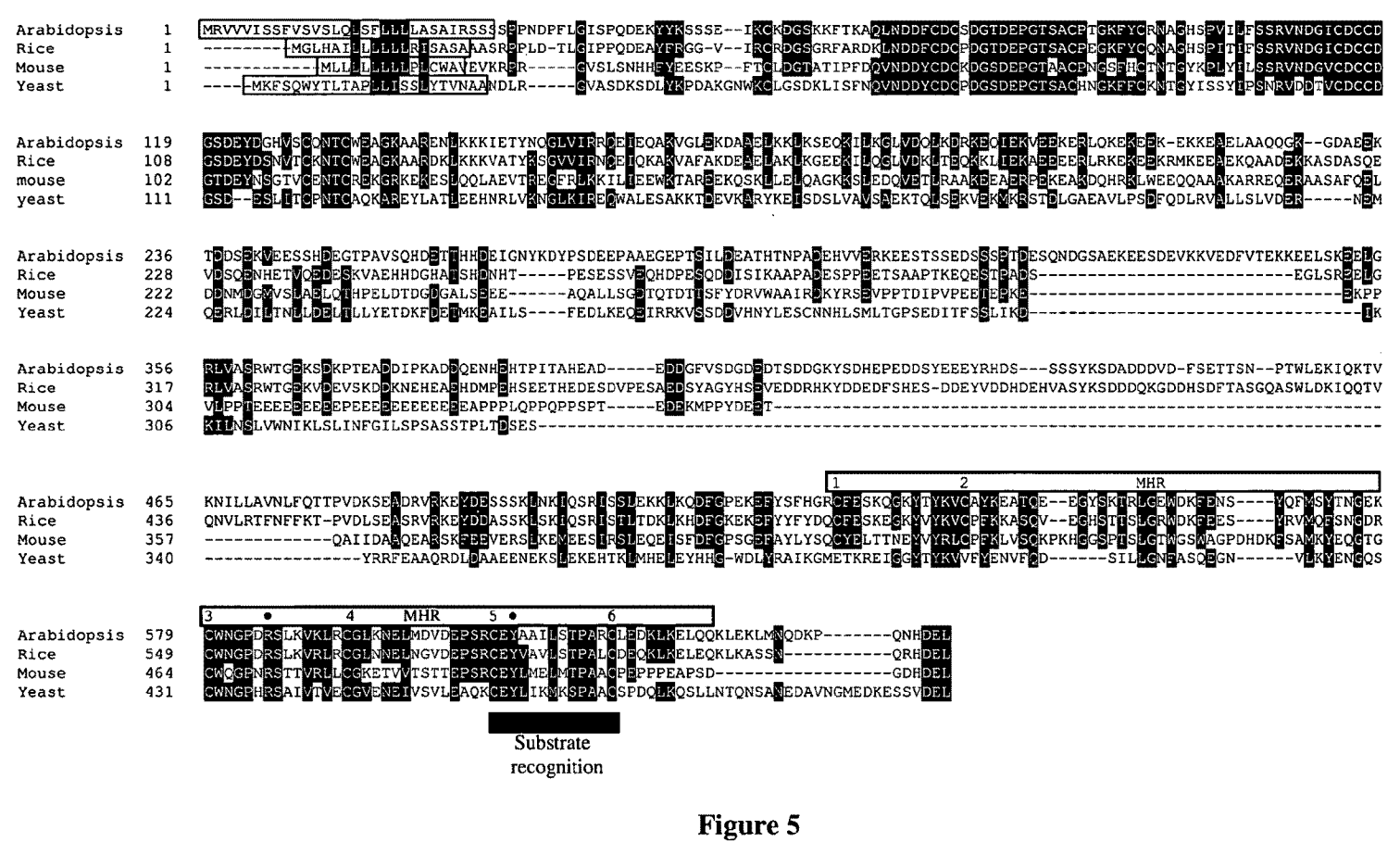

Recent biochemical (Trombetta et al, 1996) and genetic studies (D'Alessio et al, 1999; Pelletier et al., 2000) suggest that native glucosidase II of mammals and yeast consists of a catalytic α-chain (to which Aglu-3/RSW3 is homologous) and a smaller non-catalytic β-chain which retains the heterodimer in the ER. To determine if *Arabidopsis* contained an ortholog of the β-subunit, a BLAST search of the NCBI database was carried out with the mouse β-subunit. Unknown protein At5g56360 (protein MCD7.9 on the P1 clone MCD7 (AB009049) from chromosome 5) had 27% amino acid identity and 42% similarity to the mouse β-subunit. A closely related sequence (GenbankBAA88186) exists on chromosome 1 in rice but is annotated with a stop codon that truncates it after 496 residues. The conceptual translation of the adjacent 3' sequence on the PAC clone P0038F12 (AP000836) and reconsideration of proposed splice sites indicate the potential to encode a full length β-subunit that is very similar to the *Arabidopsis* gene product. The proposed sequence of the gene product is supported by an EST (AU030896) matching the proposed exons. FIG. 5 therefore includes our suggestion for the full length rice protein. The *Arabidopsis*, rice, mouse and *Schizosaccharomyces pombe* sequences share: HDEL ER-retention signals at the C-termini; predicted leader sequences at their N-termini; a cysteine-rich N-terminal region; a MHR (mannose-receptor homology region) (Munro, 2001) preceding the HDEL sequence at the C-terminus; a central region rich in acidic residues and flanked by regions giving high scores in programs ("Coils" and "Paircoil") predicting the likelihood of sequences forming coiled coils (Berger et al., 1995; Lupas et al, 1991).

Munro (2001) links the MRH domain to carbohydrate recognition. It comprises a region of similarity to the cation-dependent mannose 6-phosphate receptor whose crystal structure is known. Critical conserved features (FIG. 5) include the 6 Cys residues forming 3 disulphide bonds (although the *S. pombe* protein lacks cysteines 1 and 2), the substrate recognition loop between the cysteines 5 and 6 and the Y and R residues implicated in ligand binding (Roberts et al., 1998). Interaction between mouse α and β subunits was mapped to the N-terminal 118 residues of the β-subunit, which are reasonably well conserved in all sequences, and to residues 273-400 (Arendt and Ostergaard, 2000) which are not. FIG. 5 shows, however, that all sequences show a high percentage of acidic residues.

Expression of the genes encoding the α and β-subunits was analyzed using RT-PCR in the following way. RNA (Parcy et al. 1994) was treated with RQ1 RNase-free DNase (Promega, Madison, Wis.) following the manufacturer's instructions. PCR primers were designed to the 3' end of the coding region of the α and β-subunits of *Arabidopsis* glucosidase II:

```
α-forward
5'-CGTAGTGGTCTACTGGTTCAA-3',      (SEQ ID No 16)

α-reverse
5'-TGAGCTGTGTCCCAAGAGGAT-3',      (SEQ ID No. 17)

β-forward
5'-GGTGATGAGGATACCAGCGAT-3',      (SEQ ID No. 18)

β-reverse
5'-CCCACTCCCTAACCGGAGTTT-3'.      (SEQ ID No. 19)
```

Figure 6:
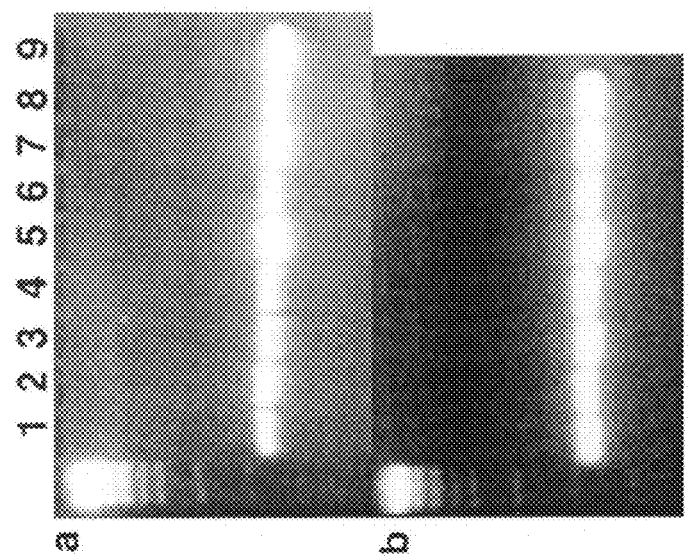
FIG. 6. mRNA for both the α-subunit (a) and the β-subunit (b) occurs in all *Arabidopsis* tissues tested. RT-PCR using mRNA from root (lane 1), whole rosette leaves (2), leaf blades (3), mature stem tissue (4), cauline leaves (5), flower buds (6), flowers (7), siliques (8), dark grown hypocotyls (9). (The presence of the β-subunit in dark grown hypocotyls was demonstrated in another experiment).

Each primer spanned an intron so differentiating RT-PCR products from genomic DNA and mRNA (724 bp versus 452 bp for the α-subunit, 996 versus 474 for the β-subunit). RT-PCR was carried out using the Gibco BRL Superscript one step RT-PCR kit, following the manufacturer's instructions and an RT-PCR cycle of 48° C. 0.45 min, 94° C. 2 min, (94° C./30 sec, 54° C./1 min, 68° C./2 min)×45, 72° C.-7 min. RT-PCR detected expression of the genes encoding the α and β-subunits in all tested tissues of *Arabidopsis* (FIG. 6) but, under the conditions used, will not clearly indicate relative expression levels. The low numbers of ESTs in *Arabidopsis* (13 for the α-subunit, 4 for the β-subunit), suggest neither gene is highly expressed. (For comparison, AtCesA1/RSW1, a glycosyltransferase implicated in cellulose synthesis, detects 40 ESTs in a similar search.)

EXAMPLE 4

Figure 3:
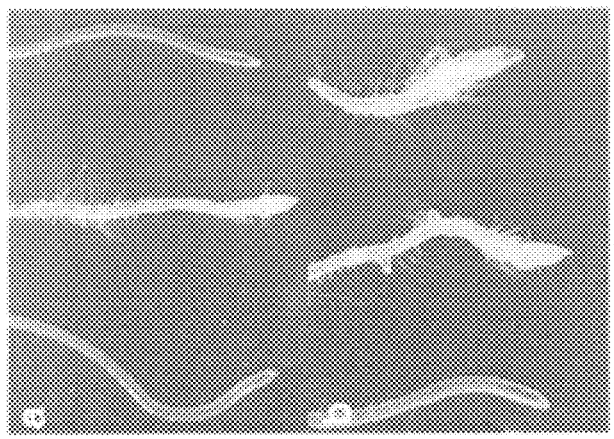
FIG. 3. Mutations in the gene encoding glucosidase II cause radial swelling. (a) Complementation of root radial swelling in rsw3 transformed with the 5.8 kB fragment amplified from the wild-type genome. Columbia wild type (left), rsw3 (center) and a kanamycin-resistant T1 seedling of rsw3 transformed with a genomic copy of the glucosidase II gene (right). The wild type gene suppresses radial swelling. All plants were transferred to 30° C. for 2 d prior to photographing. (b) The rsw3 mutation is allelic to the insertional mutant 5 GT5691 which contains a Ds element in the first exon of the glucosidase II gene. Columbia wild type (left), rsw3 (center) and a heterozygous F1 plant from crossing 5 GT5691 with rsw3. The F1 heterozygote and the rsw3 homozygote show temperature-induced radial swelling. All plants were transferred to 30° C. for 2 d prior to photographing.

Complementation of the rsw3 Mutation by a Genomic Copy of the *Arabidopsis* Gene A genomic copy of the glucosidase II α-subunit including 830 bp of the promoter region was generated by PCR amplification of BAC F20A11 using the forward primer 5'-CCGCTCGAGCGGTTTCACTCACAACT-GTGGTCTCT-3' (SEQ ID No. 20) and the reverse primer 5'-CCGCTCGAGCGGTCTCCTAAGTCCTAACCCCATA-3'(SEQ ID No. 21). Both primers included a XhoI site (underlined) which allowed the amplified 5.8 kb fragment to be ligated into the SalI site in the binary vector pBin19. The amplified product showed a single base pair change (C to T) from the genomic sequence. This substituted Leu for Ser 142, a residue that is conserved in potato but not in other species (FIG. 4) and did not impair the ability of the fragment to complement rsw3. The construct was introduced into *Agrobacterium tumefaciens* strain AGL1 and used to transform the rsw3 mutant by floral dipping (Clough and Bent, 1998). Kanamycin-resistant transformants were selected at 21° C. on Hoaglands's plates containing kanamycin (50 µg ml$^{-1}$) and timentin (100 µg ml$^{-1}$). Healthy seedlings were transferred to vertical Hoagland's plates and placed at 30° C. for 2 days to screen for root swelling. Kanamycin resistant T1 progeny had wild-type roots when grown for 5 days at 21° C. followed by 2 days at 30° C. (FIG. 3a). The inflorescence phenotype (see later) was also complemented.

A second line of evidence was provided by crosses between rsw3 and the tagged mutant SGT5691 (Parinov et al., 1999), which contains a Ds element in the first exon of the gene encoding the putative glycosidase II enzyme. It presumably represents a null allele and the mutation is homozygous lethal so hemizygous plants, which appear wild type, were used for crossing. The NPTII gene present on the Ds element confers kanamycin resistance to F1 plants receiving the tagged allele from SGT5691. Roots of all kanamycin-resistant F1 seedlings (containing a null allele and a temperature-sensitive allele) appeared wild-type at 21° C. but swelled at 30° C. (FIG. 3b). This confirms that the Ds insertion mutant and the EMS generated mutant rsw3 are allelic and that glucosidase II defects cause radial swelling.

EXAMPLE 5

Figure 7:
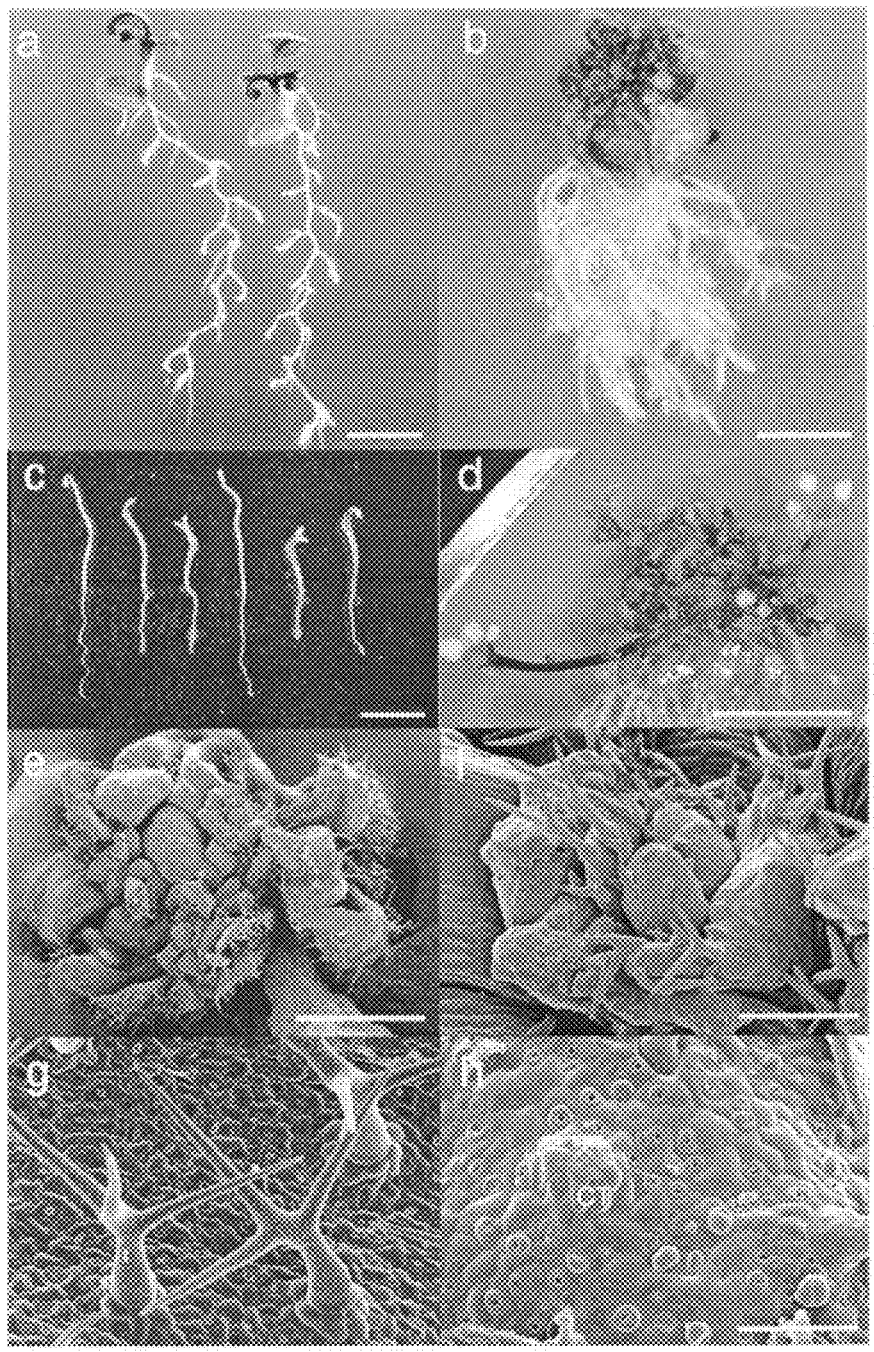
FIG. 7. Morphology of rsw3.
(a) Root system of a seedling showing that lateral roots extend some distance before swelling and stopping elongation. Plants grown 5 d at 21° C. and 6 d at 30° C. Scale bar=2 mm.
(b) Continued root growth gives a dense, highly branched root system and a dense mass of very small leaves on a plant grown for 21 d at 30° C. Scale bar=5 mm.
(c) Hypocotyls grown in the dark for 3 d at 21° C. and 3 d at 30° C. From the left: wildtype, rsw1-1, rsw2-1, rsw3, rsw1-1rsw2-1, rsw1-1rsw3. The rsw3 effect on the hypocotyl is weak compared to that of the other single mutants and rsw1-1rsw3 is weaker than rsw1-1rsw2-1. Scale bar=5 mm.
(d) Light micrograph of rsw3 grown on agar for 35 d at 30° C. Tiny inflorescences with flower buds of near normal size (top right and bottom left) emerge from several of the rosettes. Scale bar=5 mm.
(e) Scanning electron micrograph of rsw3 plant grown for 21 d at 30° C. and showing the presence of multiple rosettes. Scale bar=1 mm.

Observations on Other Phenotypes Associated With the rsw3 Mutation in *Arabidopsis* rsw3 grows like wild type at its permissive temperature of 21° C. and the seedling root swells when transferred to 30° C. The bulging cells on the root (Baskin et al., 1992) are often at the base of root hairs suggesting a role for RSW3 in the early stages of root-hair development. The swollen primary root only resumes elongation if returned to the permissive temperature within 48 h but the root continues to generate laterals (FIG. 7a). The laterals—whose primordia were not visible when the transfer to 31° C. was made—elongate for several mm before they in turn swell and stop growing. The root system of mature vegetative plants is consequently short and very highly branched (FIG. 7b). The double cellulose-defective mutant rsw1-rsw3 showed only a slightly swollen root tip after 24 h at the restrictive temperature but since any longer period at the high temperature led to death, swelling was probably already curtailed after 24 hours at the restrictive temperature.

The phenotype in dark-grown hypocotyls is much weaker in rsw3 than in rsw1-1 and rsw2-1 and the phenotype in rsw1-1rsw3 is weaker than rsw1-1rsw2-1 (FIG. 7c). Rosette growth of rsw3 in the light is strongly suppressed and many minute leaves are packed in a dense mat in which regular phyllotaxis cannot be recognized (FIG. 7d-f). The complex pavement cell shape in wild-type leaves (FIG. 7g) is simplified in rsw3, stomata protrude from the leaf surface and some trichomes appear to burst (FIG. 5h). Several of the crowded rosettes initiated minute inflorescences (FIG. 7d) although these appear much later than wild-type inflorescences (28.6±0.5 days versus 15.5±0.17 days for agar grown plants; mean±SE, n=98 for rsw3, n=45 for wild type). The few flowers on the minute rsw3 inflorescences were essentially full-sized although anther filaments, gynoecium and sepals were slightly shortened and buds opened prematurely before the stigma was receptive (similar to the buds from soil grown rsw3 plants shown in FIG. 8e, f which are discussed below).

To investigate the direct effects of the mutation on stem growth, wild-type and rsw3 were grown at 21° C. on soil so that subsequent inflorescence development would not be limited by a small rosette supplying little photosynthate. Rosettes of rsw3 were very similar to wild type under these conditions and reproductive growth began at the normal time.

Primary bolts were cut off and regrowth of secondary bolts followed at either 21° C. or 30° C. (FIGS. 6a, b). Regrowth followed a slightly S-shaped curve with rsw3 and rsw1-1 at 21° C. showing statistically insignificant reductions in growth rate and final height relative to wild type. Rsw1-1rsw3 showed a clear reduction in rate and final height. At 30° C., however, the rsw3 growth rate was similar to wild type for a few days but elongation stopped by about day 5 whereas it continued in wild type until day 16 and even longer in rsw1-1 (FIG. 8b). rsw1-1rsw2 (Lane et al., 2001) failed to regenerate secondary bolts at 30° C. and rsw1-1rsw3 only grew to about 35 mm (FIG. 8b) and produced few flowers and no seed.

Measurements of daily stem growth increments and the lengths of epidermal cells, which had left the elongation zone when the bolts were about half grown (Table 1), were made. This allowed estimation of cell flux (the number of cells leaving the elongation zone day$^{-1}$) at that time since daily growth increment=cell length×cell flux. There was no significant reduction in either cell flux or cell length of rsw3 growing at 21° C. The rsw1-1rsw3 constitutive phenotype at 21° C. was entirely due to a reduction in cell length. At 30° C., rsw1-1 showed a 57% reduction in cell length and a 35% reduction in cell flux relative to wild type.

Analyses of this type require that the plant is in a near steady state with respect to growth rate, length of the elongation zone etc. Conditions, however, are far from steady state when elongation is rapidly slowing in rsw3 and rsw1-1rsw3 so that accurate deductions of cell flux for those genotypes are precluded. To get at least an idea of how cell length was behaving when growth was slowing, we measured cell lengths at a height of about 80 mm on the rsw3 stem. (FIG. 8b shows that when these cells left the elongation zone, the stem would have been near the end of its growth phase since total plant height at that time would have exceeded 80 mm by the length of the growth zone at that time; 40 mm in wild type according to Fukaki et al., 1996). The cells in rsw3 were, even then, only slightly shorter than wild type (Table 1) suggesting that falling cell production rates were probably more important than reduced cell expansion in slowing stem elongation. In contrast, when we sampled the rsw1-1rsw3 stem at 30 mm for cells maturing when its elongation was slowing (FIG. 8b), cell length was reduced by 57% (Table 1). This is consistent with the presence of rsw1-1 in the double mutant tilting the balance strongly towards reduced cell length.

These conclusions regarding cell division and cell expansion were checked in a simpler system by using cryo-scanning electron microscopy to examine stamen filaments in flowers showing receptive stigmas (Table 2). The results were similar: rsw3 plants again showed a greater percentage reduction in cell number than in cell length and the double mutant rsw1-1rsw3 showed a further reduction in cell length without an additional reduction in cell number. Rsw1-1 showed a much greater reduction in cell length than in cell number (Table 2). Stems of both wild type and rsw3 regenerating at 30° C. reached approximately the same height before initiating their first flower even though their final heights would be very different (FIG. 8b). Wild-type stems generated about 27 well spaced flowers before elongation ceased but rsw3 produced only about 6 closely spaced flowers before elongation ended leaving a cluster of flowers (FIGS. 8c, d). rsw3 flower buds opened precociously before the stigma was receptive (FIGS. 8e, f).

Few flowers and no seed formed on the minute bolts of rsw3 plants grown continuously at their restrictive temperature (FIG. 7d). Even flowers on the much larger bolts formed at 31° C. on plants which had completed vegetative growth at 21° C. (FIGS. 8d, f) also set very little seed. That seed (FIGS. 8g, h) was shrunken (probably because of reduced accumulation of seed storage proteins; Boisson et al., 2001), its surface lacked the regular cellular structure of wild type grown at 30° C. or of rsw3 grown at 21° C. and it showed very little secreted mucilage after imbibition (FIG. 8i-n). Reduced mucilage secretion was not typical of cellulose-deficient mutants: rsw1-1 (defective in the CesA1 glycosyltransferase; FIGS. 8 k, l), and rsw2-1 (defective in the KOR endo-1,4 β glucanase) had normal mucilage coats.

To isolate effects on the haploid stages of pollen and ovule development from effects on the diploid stages, we examined seed set in the hemizygous Ds-mutant SGT5691 (a presumed null allele in the glucosidase II catalytic subunit). Seed set by self-fertilization segregates 147 kanamycin-resistant individuals to 153 sensitive individuals. A ratio less than the 2:1 expected for a dominant, homozygous lethal allele shows that the null allele affects post-meiotic development of pollen and/or ovules. We separated the effects on the male and female pathways by reciprocal crosses between the hemizygous tagged mutant and Landsberg erecta (the appropriate wild type for this mutant). Kanamycin-resistant and sensitive plants will segregate 1:1 if pollen or ovule development is unaffected with lower ratios if the null allele reduces pollen or ovule fertility. Pollen from the Ds-tagged mutant gave a segregation ratio of 1:16 (6 resistant: 94 sensitive individuals) indicating a 94% reduction (relative to wild type) in the ability of Ds-tagged pollen to set viable seed. This compared with a 41% reduction when Ds-tagged ovules were crossed to wild type pollen (ratio of 1:1.7, 37:63 individuals). The null allele of glucosidase II therefore affects the haploid stages of pollen development much more severely than it affects post-meiotic ovules.

Roots of 7 day old seedlings of rsw3 grown at 31° C. contain only 51% of the wild-type cellulose (expressed mg-i tissue dry weight), a comparable figure to that resulting from single amino acid substitutions in the CesA1 glycosyltransferase (rsw1-1) and the KOR endo-1,4-β-glucanase (rsw2-1) (Peng et al., 2000). The morphological changes indicate that all three genes are needed to make cellulose in primary cell walls.

Production of Golgi-derived non-cellulosic polysaccharides changes little in rsw3 seedlings (Peng et al., 2000). The selectivity for cellulose production is comparable to that seen with a defect in glucosidase I (Gillmor et al., 2002), the enzyme generating the initial substrate for glucosidase II processing. It exceeds the selectivity seen in the embryo-lethal cyt1 mutants of Arabidopsis (defective in mannose-1-phosphate guanylyltransferase) (Lukowitz et al., 2001) and in potatoes with MAL1 (encoding a glucosidase II α-subunit) down-regulated by antisense (Taylor et al., 2000a) where complex changes occur in non-cellulosic polysaccharides and lignin. We therefore conclude that cellulose synthesis is often much more sensitive to N-glycan processing defects than is the synthesis of non-cellulosic polysaccharides in the Golgi.

Secretion of Golgi-derived seed mucilage is strongly reduced in rsw3 but not in rsw1-1 or rsw2-1. Mucilage could be produced but retained intracellularly (perhaps because of structural changes resulting from cellulose deficiency), or mucilage production itself could be reduced. Many developmental blocks reduce mucilage production (Western et al., 2001; Western et al., 2000) but we cannot yet exclude the possibility that rsw3 has defective processing of Golgi enzymes required to make the particular non-cellulosic polysaccharides making up the mucilage.

Cell numbers and sizes in stamen filaments indicate that rsw3 affects cell division more strongly than cell expansion. The cell length data for the stem are consistent with this finding. A strong effect of rsw3 on cell division may explain why its phenotype is rather weak in dark grown hypocotyls which lack cell division (Gendreau et al., 1997). In more strongly affecting cell division than cell expansion, rsw3 resembles rsw2-1 (Burn et al, 2002) rather than rsw1-1 (Burn et al., 2002) or plants carrying antisense constructs to RSW1/CesA1 or CesA3 (Burn et al., 2002) which are more severely affected in cell length. (Although CesA1 changes have little impact on division rates, CesA1 is probably expressed in dividing root cells since they show changes in wall ultrastructure (Sugimoto et al. 2001) and swell (Baskin et al., 1992; Beemster and Baskin, 1998) when rsw1-1 is at its restrictive temperature.)

Although it is clear that cellulose biosynthesis is impaired in the rsw3, the mechanism by which rsw3 affects cellulose synthesis is not yet clear. As noted in relation to a glucosidase I mutation (Boisson et al., 2001), the minimal phenotype shown by a mutant which cannot assemble mature N-linked glycans in the Golgi (von Schaewen et al, 1993) indicates that a lack of mature N-linked glycans on critical proteins will not cause the strong phenotype seen with a glycosidase II defect. Reduced rates of production of $Glc_1Man_9GlcNAc_2$ and $Man_9GlcNAc_2$ would probably slow both the formation and dissociation of the glycoprotein/chaperone complex creating a bottleneck that may in time reduce the steady state levels of glycoproteins at sites further along the secretory pathway. Because glycoproteins participate in many plant processes, it is not obvious why cellulose synthesis should be much more sensitive to processing defects in the ER than, for example, synthesis of non-cellulosic polysaccharides.

Gillmor et al. (2002) argued that CesA proteins are not glycosylated when they did not detect a mobility shift on SDS-PAGE in knopf (deficient in glucosidase I) or alter N-glycosidase F treatment and when they did not see in knopf a change in CesA abundance that was visible by unquantified immunostaining. The KOR endo-1,4-β-glucanase is a better candidate. A soluble fragment of the *Brassica napus* ortholog of KOR is heavily N-glycosylated when expressed heterologously in *Pichia pastoris* and the N-glycan is required for in vitro activity (Molhoj et al. 2001). Further evidence consistent with KOR being a target can be drawn from the rsw3 and rsw2-1 phenotypes affecting cell division more than cell expansion whereas the rsw1-1 phenotype shows the reverse.

The rsw1-1 and rsw2-1 mutations affect genes encoding plasma membrane enzymes that are probably directly involved in cellulose synthesis so that changed enzyme performance at the restrictive temperature will rapidly impact on cellulose synthesis. rsw3, in contrast, encodes a processing enzyme in the ER whose changed performance will reduce cellulose synthesis only when it restricts the supply of properly folded glycoproteins to the site of cellulose synthesis.

The different time courses for the onset of a visible phenotype when the three mutants are transferred to the higher temperature plausibly reflect these different modes of action. Radial swelling starts slowly in rsw3 (latency>24 h compared to <12 h in rsw1-1 and rsw2-1) and the high temperature actually accelerates root elongation during the first 12 h, albeit by less than in wild type (Baskin et al., 1992).

Elongation of rsw1-1 or rsw2-1, in contrast, falls during the first 12 h, roots swell strongly and rsw1-1 shows changed wall ultrastructure within 4 h (Sugimoto et al., 2001).

It has been shown that rsw3 is mutated in a gene encoding a putative glycosidase II α-subunit, identified a putative β-subunit encoded by two plant genomes and shown that many aspects of the rsw3 phenotype flow from reduced cellulose synthesis in primary walls. Cell division seems more strongly affected than cell expansion indicating that the KOR endo-1,4-β-glucanase, where mutations also strongly affect cell division, may be the glycoprotein affected by the processing defect. In addition to its role in cellulose synthesis, a temperature-sensitive allele of glucosidase II will contribute to studies of N-glycosylation and quality control in the ER and in establishing its links to other developmental and physiological processes.

EXAMPLE 6

Isolation of a (Partial) cDNA Corresponding to RSW3 From Cotton

A dbEST search using the sequence of RSW3 as query, identified a Gossypium arboreum cDNA with 833 bp of high quality sequence. Primers designed from the EST were used to amplify a 700 bp product form a library of 18 dpa fibers of G. hirsutum cDNA using the following primers:

```
Cot-rsw3f
5'-CGGGATGAAGAGGATGTAGAG 3'     (SEQ ID No. 22)

Cot-rsq3r
5'-GAACCCCTGAGATGATCCCAA 3'     (SEQ ID No. 23)
```

The PCR product was used as a probe to identify longer cDNAs. 5 putative clones were identified and 2 were sequenced. The three clones overlapped and the sequence of cDNA of the cotton RSW3 homolog was assembled (SEQ ID No. 4). The region encoding the N-terminus is missing.

EXAMPLE 7

Expression of RSW2/RSW3 Chimeric Genes in Cotton cDNAs corresponding to RSW2 or RSW3, isolated from Arabidopsis or cotton are operably linked to a promoter such as the expansion promoter and a 3' end region involved in transcription termination and polyadenylation.

Further, about 100 bp long fragments selected from the RSW2 or RSW3 genes isolated from Arabidopsis or cotton are cloned in inverted repeat under the control of a promoter such as the CaMV35S promoter.

The chimeric genes are introduced into a T-DNA vector comprising further a selectable marker gene, and the resulting T-DNA vectors are introduced into *Agrobacterium tumefaciens* strains containing a helper Ti-plasmid. Transgenic cotton plants are obtained using these *Agrobacterium* strains.

Plants expressing copies of the different transgenes are analyzed further for cell wall components, including cellulose, non-crystalline β-1,4 glucan polymer, starch and carbohydrate content as described in WO 98/00549.

TABLE 1

Analysis of the rate of stem elongation in terms of cell length and, where near steady growth rates occurred, cell flux (number of cells $day^{-1}$ leaving the elongation zone).

| | | Growth rate (mm $day_{-1}$) | Cell flux ($day_{-1}$) | Cell length (μm) |
|---|---|---|---|---|
| 21° C. | Columbia | 38.7 ± 1.0 | 101 ± 3.5 | 384 ± 4.0 |
| | rsw3 | 38.4 ± 1.4 | 95.9 ± 4.6 | 402 ± 7.0 |
| | rsw1 | 38.9 ± 1.6 | 102 ± 6.9 | 382 ± 9.8 |
| | rsw1rsw3 | 30.2 ± 1.9** | 100 ± 7.6 | 299 ± 8.4** |
| 30° C. | Columbia | 53.8 ± 1.2 | 133 ± 2.7 | 404 ± 3.2 |
| | rsw3 | 41.8 ± 3.1** | | 378 ± 22 |
| | rsw1 | 15.2 ± 1.4*** | 87.2 ± 7.0** | 174 ± 5.8*** |
| | rsw1rsw3 | 13.6 ± 1.8*** | | 173 ± 15*** |

Results are given as mean + SE for n = 5. Statistically significant differences from wild type using the Student's T-test are indicated (*= $p < 0.05$; = $p < 0.01$; *= $p < 0.001$).

TABLE 2

Cell length and number in mature stamen filaments grown at 30° C.

| | Total length (μm) | Cell number | Cell length (μm) |
|---|---|---|---|
| Columbia | 2407 _ 38 | 17.0 _ 1.0 | 152.7 _ 6.2 |
| rsw3 | 1458 _ 52*** | 11.4 _ 0.3*** | 127.0 _ 0.1** |
| rsw1-1 | 1050 _ 57*** | 15.0 _ 0.4 | 72.7 _ 9.8*** |
| rsw1-1rsw3 | 415 _ 41*** | 12.4 _ 0.5*** | 29.4 _ 2.1*** |

Results are given as mean + SE for n > 7. Statistically significant differences from wild type using the Student's T-test are indicated (*= $p < 0.05$; = $p < 0.01$; *$p = <0.001$).

REFERENCES

Arioli et al. (1998) *Science* 279: 717-720.
Arendt et al. (2000) *Glycobiology* 10: 487-492.
Baskin et al. *Aust. J. Plant Phys.* 19: 427-437.
Beemster et al. (1998) *Plant Physiol*, 116: 1515-1526.
Berger et al. (1995) *Proc. Nat Acad. Sci. USA* 92: 8259-8263.
Boisson et al. (2001) *EMBO J.*, 20: 1010-1019.
Brad aetal. (1984) *Eur. J. Biochem.*, 141: 149-156.
Brummell et al. *Proc. Nat. Acad. Sci. USA* 94: 4794-4799.
Burn et al (2002a) *Plant Physiol.* 129: 797-807.
Clough et al. (1998) *Plant J.* 16: 735-743.
D'Alessio et al. (1999) *J. Biol. Chem.*, 274: 25899-25905.
Desprez, et al. (2002) *Plant Physiol.* 128: 482-490.
Fagard et al. (2000) *Plant Cell* 12: 2409-2424.

Frandsen et al. (1998) *Plant Mol. Biol.* 37: 1-13
Fukaki et al. (1996) *Plant Physiol.* 110, 933-943.
Gendreau et al. (1997) *Plant Physiol.*, 114: 295-305.
Gillmor et al. (2002) *J Cell Biol.* 156: 1003-1013.
Gleave, A. P. (1992) *Plant Mol. Biol.* 20: 1203-1207.
Helenius et al. (2001) *Science* 291: 2364-2369.
Henrissat (1991) *Biochem. J.* 280: 309-316
Henrissat and Bairoch (1993) *Biochem. J.* 293: 781-788.
Hino and Rothman (1985) *Biochemistry* 24: 800-805.
Kimura et al. (1999) *Plant Cell* 11: 2075-2085.
Lane et al. (2001) *Plant Physiol.* 126: 278-288.
Lukowitz et al. (2001) *Proc. Nat. Acad. Sci. USA* 98: 2262-2267.
Lupas et al. (2001) *Plant Physiol.* 127: 674-684.
Mølhøj et al. (2001) *Plant Physiol.* 127: 674-684.
Monroe et al. (1999) *Plant Physiol.* 119: 385-397.
Munro (2001) *Curr. Biol.* 11: R499-501.
Murashige and Skoog (1962) *Phys. Plant* 15: 473-497.
Nicol et al. (1998) *EMBO J.* 17: 5563-5576.
Pagant et al. (2002) *Plant Cell* 14: 2001-2013.
Parcy et al. (1994) *Plant Cell* 6: 1567-1582
Parinov et al. (1999) *Plant Cell* 11: 2263-2270.
Pelletier et al. (2000) *Glycobiology* 10: 815-827.
Peng et al. (2000) *Planta* 211: 406-414.
Peng et al. (2002) *Science* 295: 147-150.
Peng et al. (2001) *Plant Physiol.* 126: 981-992.
Roberts et al. (1998) *Cell* 93: 639-648.
Sato et al. (2001) *Plant Cell Physiol* 42: 251-263.
Scheible et al. (2001) *Proc. Nat. Acad. Sci. USA* 98: 10079-10084.
Silk et al. (1989) *Plant Physiol.* 90: 708-713.
Sugimoto et al. (2001) *Protoplasma* 215: 172-183.
Taylor et al. (2000a) *Plant J.* 24: 305-316
Taylor et al. (2000) *Plant Cell* 12: 2529-2539.
Taylor et al. (1999) *Plant Cell* 11: 769-780.
Treml et al. (2000) *Glycobiology* 10: 493-502.
Trombetta et al. (2001) *Biochemistry* 40: 10717-10722.
Trombetta et al. (1996) *J. Biol. Chem.* 271: 27509-27516.
Vitale (2001) *Plant Cell* 13: 1260-1262
von Schaewen et al. (1993) *Plant Physiol* 102: 1109-1118.
Western et al. (2001) *Plant Physiol* 127: 998-1011.
Western et al. (2000) *Plant Physiol* 122: 345-355.
Williamson et al. (2001a) *Protoplasma* 215: 116-127.
Williamson et al. (2001) *Cell. Molec. Life Sci.* 58: 1475-1490.
Zuo et al. (2000) *Plant Cell* 12: 1137-1152.

We claim:

1. A method for increasing cellulose biosynthesis in cotton plants, comprising the step of:
   providing cells of said cotton plant with a chimeric gene comprising the following operably linked DNA fragments
   i) a promoter expressible in said cell of said plant;
   ii) a DNA region coding for the protein comprising the amino acid sequence of SEQ ID No. 8 or an amino acid sequence having at least 95% amino acid sequence identity to the amino acid sequence of SEQ ID No. 8 and having the same enzymatic activity;
   iii) a 3' region involved in transcription termination and polyadenylation; thereby increasing cellulose biosynthesis in said plant.

2. The method of claim 1, wherein said DNA region comprises the nucleotide sequence of SEQ ID No. 4 from the nucleotide at position 2 to the nucleotide at position 1576.

3. The method of claim 1, wherein said promoter is a constitutive promoter.

4. The method of claim 1, wherein said promoter is a fiber-specific promoter.

5. The method of claim 1, wherein said promoter is an expansin promoter.

6. The method of claim 1, wherein said cellulose biosynthesis is increased in lint fibers.

7. A method for decreasing cellulose biosynthesis in cotton plants comprising the step of: providing cells of said cotton plant with a chimeric gene capable of reducing the expression of a gene endogenous to said cotton plant, wherein said endogenous gene codes for a protein comprising the amino acid sequence of SEQ ID No. 8 thereby decreasing cellulose biosynthesis.

8. The method of claim 7, wherein said chimeric gene comprises at least 21 contiguous nucleotides selected from a nucleotide sequence which codes for a protein comprising the amino acid sequence of SEQ ID No. 8, operably linked to a plant expressible promoter and a 3' region involved in transcription termination and polyadenylation.

9. The method of claim 8, wherein said at least 21 contiguous nucleotides are selected from the nucleotide sequence of SEQ ID No. 4.

10. The method of claim 7, wherein said chimeric gene comprises at least 21 contiguous nucleotides selected from the complement of a nucleotide sequence which codes for a protein comprising the amino acid sequence of SEQ ID No. 8, operably linked to a plant expressible promoter and a 3' region involved in transcription termination and polyadenylation.

11. The method of claim 10, wherein said at least 21 contiguous nucleotides are selected from the complement of the nucleotide sequence of SEQ ID No. 4.

12. The method of claim 7, wherein said chimeric gene comprises a first nucleotide sequence of at least 21 contiguous nucleotides selected from a nucleotide sequence which codes for a protein comprising the amino acid sequence of SEQ ID No. 8, and a second nucleotide sequence complementary to said first nucleotide sequence, operably linked to a plant-expressible promoter and a 3' region involved in transcription termination and polyadenylation such that upon transcription of said chimeric gene, an RNA is formed which can form a double stranded RNA region between said first and said second nucleotide sequence.

13. The method of claim 12, wherein said at least 21 contiguous nucleotides are selected from the nucleotide sequence of SEQ ID No. 4.

14. The method of claim 7, wherein said plant expressible promoter is a constitutive promoter.

15. The method of claim 7, wherein said plant expressible promoter is a fuzz fiber specific promoter.

16. The method of claim 7, wherein said cellulose biosynthesis is decreased in fuzz fiber production.

17. A chimeric gene comprising the following operably linked DNA fragments:
   i) a promoter expressible in plant cells;
   ii) a DNA region coding for a protein comprising the amino acid sequence of SEQ ID No. 8 or an amino acid sequence haiving at least 95% amino acid sequence identity to the amino acid sequence of SEQ ID No. 8 and having the sameenzymatic activity; and
   iii) a 3'end region involved in transcription termination and polyadenylation.

18. The chimeric gene of claim 17, wherein said DNA region comprises the nucleotide sequence of SEQ ID No. 4 from the nucleotide at position 2 to the nucleotide at position 1576.

19. The chimeric gene of claim 17, wherein said promoter is a constitutive promoter.

20. The chimeric gene of claim 17, wherein said promoter is a fiber-specific promoter.

21. The chimeric gene of claim 17, wherein said promoter is an expansin promoter.

22. A plant cell comprising the chimeric gene of claim 17.

23. A plant comprising a plant cell according to claim 22.

24. A seed of the plant of claim 23.

25. A chimeric gene comprising a first nucleotide sequence of at least 21 contiguous nucleotides selected from a nucleotide sequence which codes for a protein comprising the amino acid sequence of SEQ ID No. 8, operably linked to a plant expressible promoter and a 3' region involved in transcription termination and polyadenylation.

26. A chimeric gene according to claim 25, further comprising a second nucleotide sequence complementary to said first nucleotide sequence, operably linked to said first nucleotide sequence such that upon transcription of said chimeric gene, an RNA is formed which can form a double stranded RNA region between said first and said second nucleotide sequence.

27. A chimeric gene according to claim 25, wherein said first sequence of at least 21 contiguous nucleotides is selected from the nucleotide sequence of SEQ ID No. 4.

28. A chimeric gene according to claim 27, further comprising a second nucleotide sequence complementary to said first nucleotide sequence, operably linked to said first nucleotide sequence such that upon transcription of said chimeric gene, an RNA is formed which can form a double stranded RNA region between said first and said second nucleotide sequence.

29. A plant cell comprising the chimeric gene of claim 25.

30. A plant comprising a plant cell according to claim 29.

31. A seed of the plant of claim 30.

32. A chimeric gene comprising a first nucleotide sequence of at least 21 contiguous nucleotides selected from the complement of a nucleotide sequence which codes for a protein comprising the amino acid sequence of SEQ ID No. 8 operably linked to a plant expressible promoter and a 3' region involved in transcription termination and polyadenylation.

33. A chimeric gene according to claim 32, wherein said first nucleotide sequence of 21 contiguous nucleotides is selected from the complement of the nucleotide sequence of SEQ ID No. 4.

34. A chimeric gene according to claim 32, wherein said plant expressible promoter is a constitutive promoter.

35. A chimeric gene according to claim 32, wherein said plant expressible promoter is a fuzz fiber specific promoter.

36. A plant cell comprising the chimeric gene of claim 32.

37. A plant comprising a plant cell according to claim 36.

38. A seed of the plant of claim 37.

39. A method for identifying allelic variations of the genes encoding proteins involved in cellulose biosynthesis in a population of different genotypes or varieties of a fiber producing plant species, which are correlated either alone or in combination with the quantity and/or quality of cellulose production, and fiber production comprising the steps of:
- a) providing a population of different varieties or genotypes of a particular plant species or interbreeding plant species comprising different allelic forms of the nucleotide sequences encoding proteins comprising the amino acid sequences of SEQ ID No. 8;
- b) determining parameters related to fiber production and/or cellulose biosynthesis or each individual of the population;
- c) determining the presence of a particular allelic form of the nucleotide sequences encoding proteins comprising the amino acid sequences of SEQ ID No. 8 for each individual of the population; and
- d) correlating the occurrence of particular fiber or cellulose parameters with the presence of a particular allelic form of the mentioned nucleotide sequence or a particular combination of such allelic forms; and thereby identifying said allelic variations.

\* \* \* \* \*